US012402855B2

(12) United States Patent
Xu et al.

(10) Patent No.: US 12,402,855 B2
(45) Date of Patent: Sep. 2, 2025

(54) SYSTEM AND METHOD FOR CONTINUOUS NON-INVASIVE ULTRASONIC MONITORING OF BLOOD VESSELS AND CENTRAL ORGANS

(71) Applicant: THE REGENTS OF THE UNIVERSITY OF CALIFORNIA, Oakland, CA (US)

(72) Inventors: Sheng Xu, La Jolla, CA (US); Chonghe Wang, La Jolla, CA (US); Zhuorui Zhang, La Jolla, CA (US); Baiyan Qi, La Jolla, CA (US); Muyang Lin, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 106 days.

(21) Appl. No.: 17/604,616

(22) PCT Filed: Apr. 20, 2020

(86) PCT No.: PCT/US2020/028983
§ 371 (c)(1),
(2) Date: Oct. 18, 2021

(87) PCT Pub. No.: WO2020/215075
PCT Pub. Date: Oct. 22, 2020

(65) Prior Publication Data
US 2022/0175340 A1  Jun. 9, 2022

Related U.S. Application Data

(60) Provisional application No. 62/972,358, filed on Feb. 10, 2020, provisional application No. 62/835,857, filed on Apr. 18, 2019.

(51) Int. Cl.
*A61B 8/06*   (2006.01)
*A61B 8/00*   (2006.01)
(Continued)

(52) U.S. Cl.
CPC ............. *A61B 8/06* (2013.01); *A61B 8/4236* (2013.01); *A61B 8/4263* (2013.01);
(Continued)

(58) Field of Classification Search
CPC ....... A61B 8/06; A61B 8/4236; A61B 8/4263; A61B 8/4444; A61B 8/4488; A61B 8/461;
(Continued)

(56) References Cited

U.S. PATENT DOCUMENTS 8,852,103 B2 * 10/2014 Rothberg ................ A61N 7/02
600/459
2006/0241459 A1  10/2006 Tai
(Continued)

FOREIGN PATENT DOCUMENTS

CN  102358335 A   2/2012
RU  2675217 C1   12/2018
(Continued)

OTHER PUBLICATIONS

Hongjie HU et al. Stretchable ultrasonic transducer arrays for three-dimensional imaging on complex surfaces, Science Advances, vol. 4, No. 4, Mar. 23, 2018.

*Primary Examiner* — Alexei Bykhovski
(74) *Attorney, Agent, or Firm* — Stuart Mayer; Kaplan Breyer Schwarz LLP

(57) ABSTRACT

A method for monitoring a patient using an ultrasonic probe includes attaching a conformable two-dimensional piezoelectric transducer array having a plurality of phased array piezoelectric transducer elements on an epidermal surface of
(Continued)

a patient so that the conformable two-dimensional piezoelectric transducer array conforms to a shape of the epidermal surface. The conformable two-dimensional piezoelectric transducer array is attachable to the epidermal surface by van der Waals forces alone. The plurality of phased array piezoelectric transducer elements is operated as a phased array to transmit a focused ultrasonic beam to a specified location in the patient to be monitored. Ultrasound waves are received from the patient using the array. An indication of the received ultrasound waves is displayed.

17 Claims, 57 Drawing Sheets

(51) Int. Cl.
*A61B 8/08* (2006.01)
*B06B 1/06* (2006.01)
(52) U.S. Cl.
CPC .......... *A61B 8/4444* (2013.01); *A61B 8/4488* (2013.01); *A61B 8/461* (2013.01); *A61B 8/488* (2013.01); *A61B 8/54* (2013.01); *B06B 1/0629* (2013.01); *B06B 1/0681* (2013.01); *B06B 2201/76* (2013.01)
(58) Field of Classification Search
CPC .. A61B 8/488; A61B 8/54; A61B 8/42; A61B 8/0891; B06B 1/0629; B06B 1/0681; B06B 2201/76
See application file for complete search history.

(56) References Cited

U.S. PATENT DOCUMENTS

| | | | |
|---|---|---|---|
| 2009/0163816 A1* | 6/2009 | Azuma | A61B 8/06 600/454 |
| 2012/0271294 A1 | 10/2012 | Barthe | |
| 2014/0228688 A1* | 8/2014 | Gupta | A61B 8/488 600/454 |
| 2017/0100092 A1* | 4/2017 | Kruse | G01S 15/8997 |
| 2017/0100585 A1 | 4/2017 | Hall et al. | |
| 2017/0311924 A1* | 11/2017 | Sudol | A61B 8/4254 |
| 2018/0014734 A1 | 1/2018 | Rogers et al. | |
| 2019/0184206 A1 | 6/2019 | Nazer et al. | |
| 2019/0216438 A1* | 7/2019 | Song | A61B 8/4455 |
| 2019/0298309 A1* | 10/2019 | Owen | A61B 8/467 |
| 2021/0196242 A1* | 7/2021 | Perez | A61B 8/5269 |
| 2021/0282748 A1* | 9/2021 | Stehle | A61B 8/4494 |

FOREIGN PATENT DOCUMENTS

| | | |
|---|---|---|
| WO | 2008137030 A1 | 11/2008 |
| WO | 2017096487 A1 | 6/2017 |
| WO | 2017216084 A1 | 12/2017 |
| WO | 2018071908 A1 | 4/2018 |
| WO | 2018/132443 A1 | 7/2018 |
| WO | WO2018132443 * | 7/2018 |
| WO | 2020176830 A1 | 9/2020 |

* cited by examiner

On non-developable surface

Device property demonstration

Arterial stiffness evaluation-ECG correlation

Video: Hemodynamics monitoring-flow velocity profile

TESTING SITUATION

*PRESSURE INCREASE FROM 0 mmHg~180 mmHg

Accurate compared to gold standard

Testing on the radial artery of same subject

Advantage: *EZ U/S* accuracy comparable to commercial probes without need for operator expertise Device robustness Advantages:
• Our device has supreme testing durability and reproducibility.

FIG. 21A
FIG. 21B
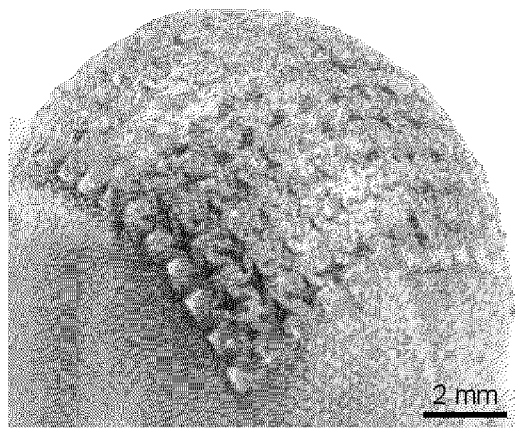
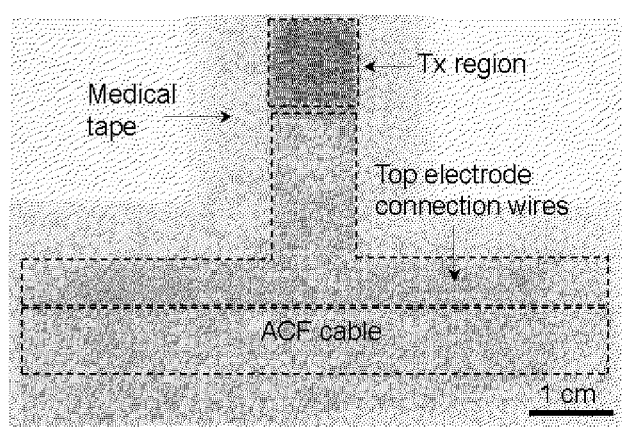
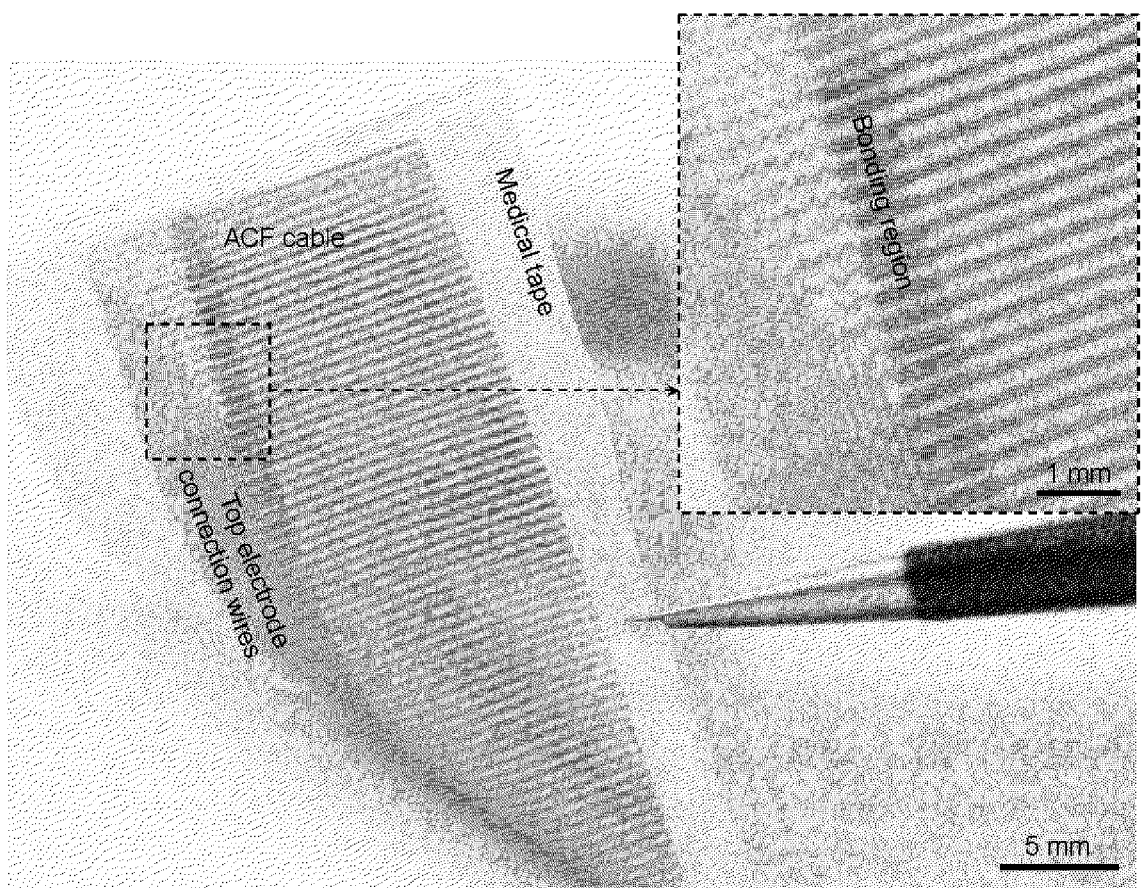
FIG. 21C

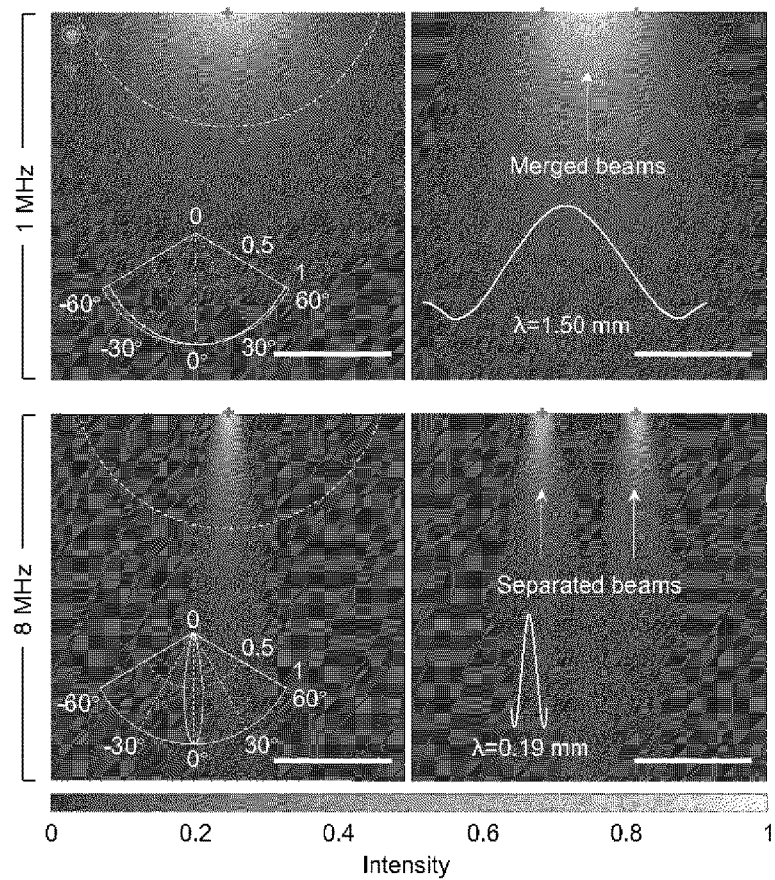
FIG. 24A
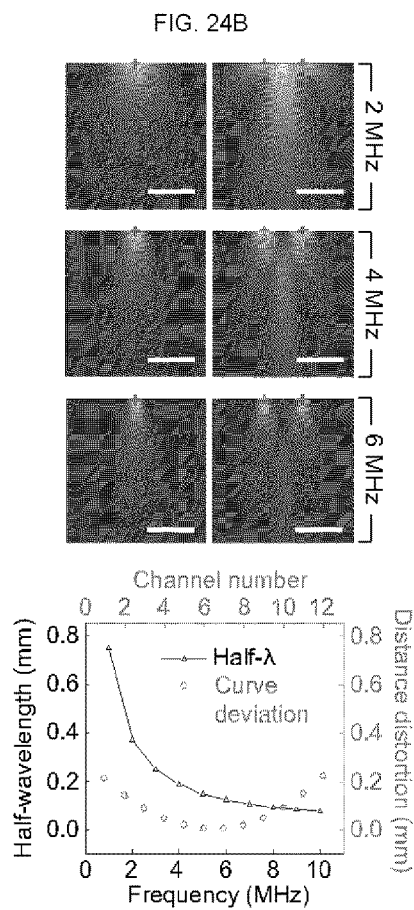
FIG. 24B
FIG. 24C

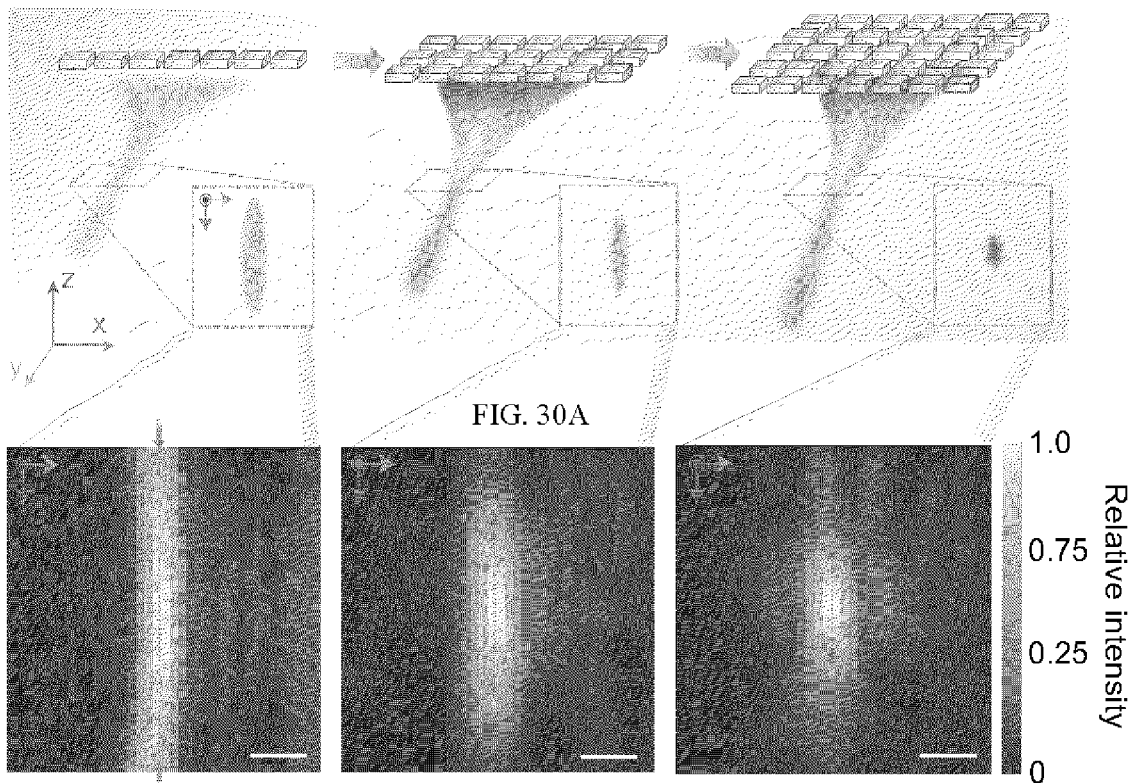
FIG. 30A
FIG. 30B
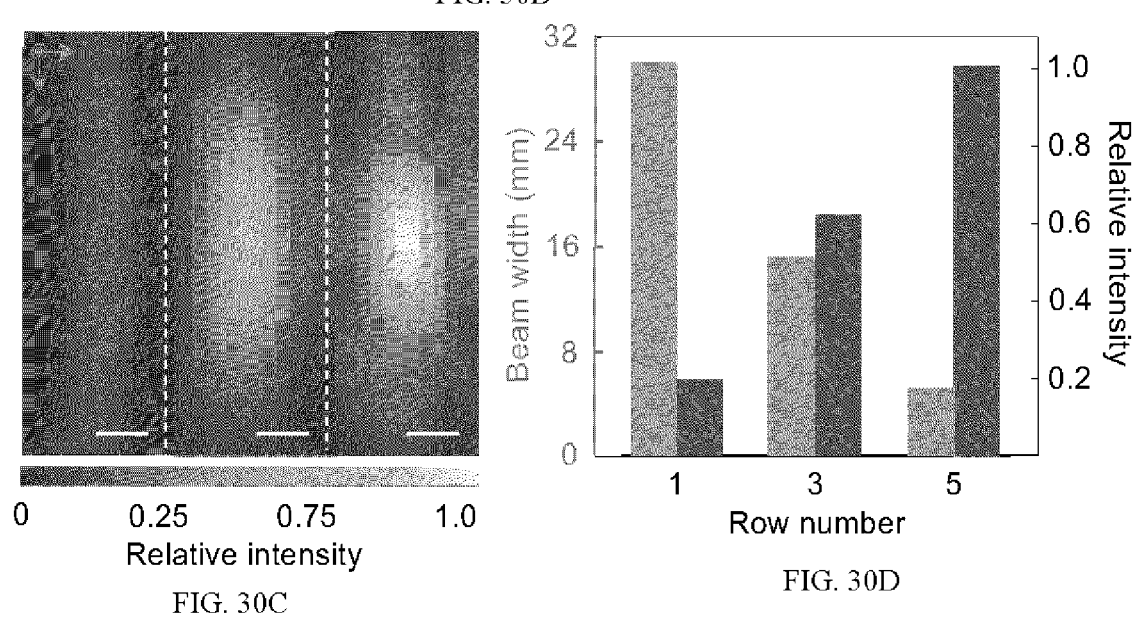
FIG. 30C
FIG. 30D

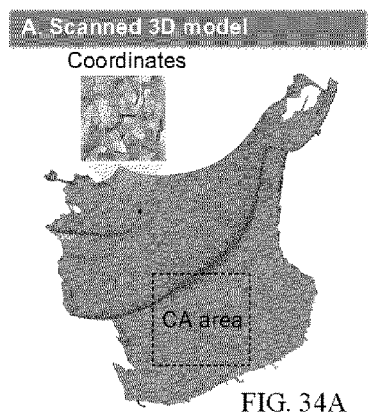 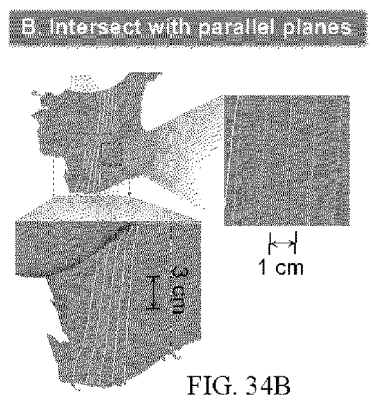 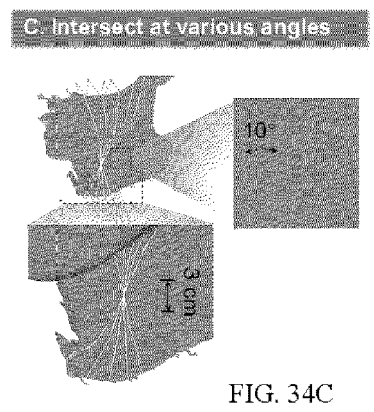
FIG. 34A  FIG. 34B  FIG. 34C
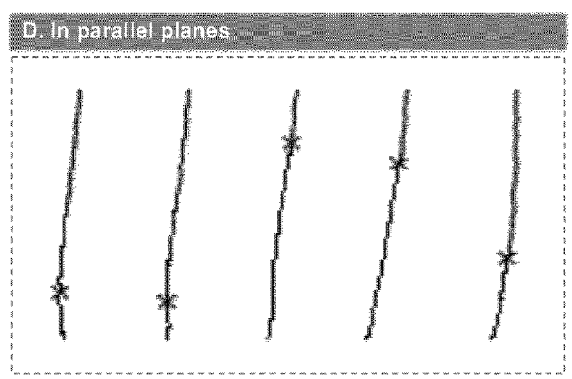 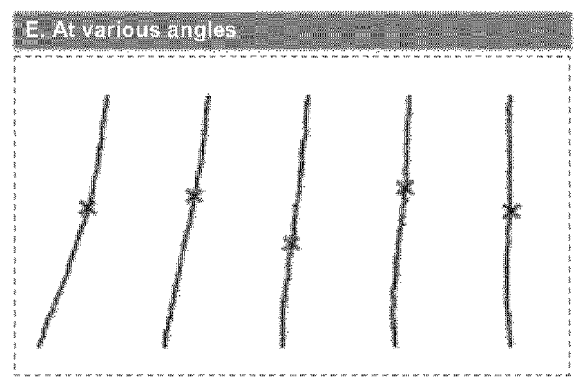
FIG. 34D  FIG. 34E FIG. 41A
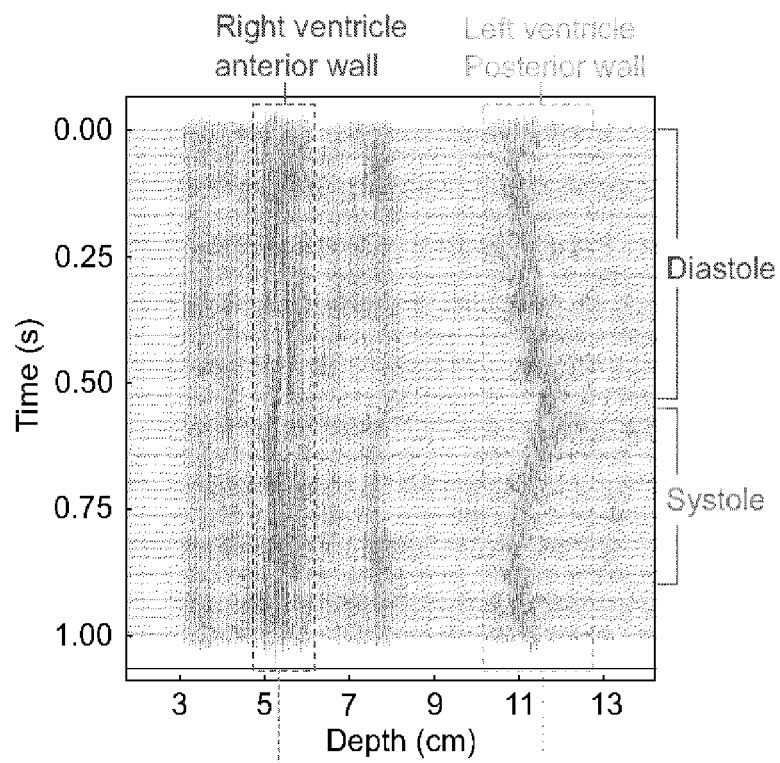
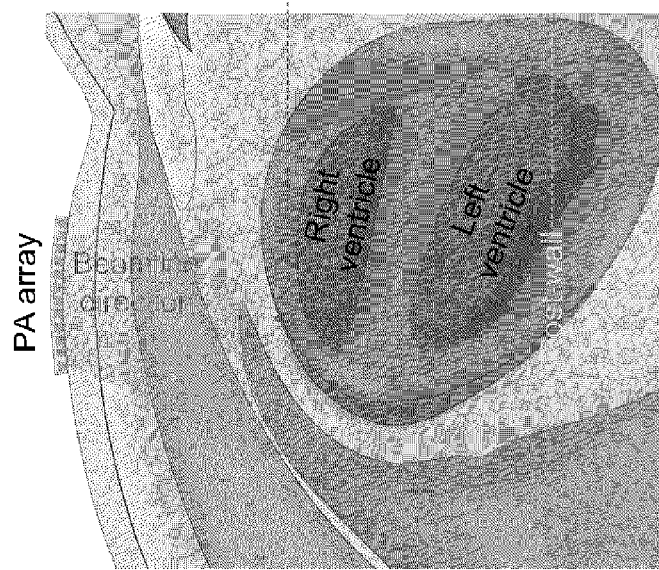
FIG. 41B

SYSTEM AND METHOD FOR CONTINUOUS NON-INVASIVE ULTRASONIC MONITORING OF BLOOD VESSELS AND CENTRAL ORGANS

BACKGROUND

Peripheral vascular disease (PVD), characterized by reduced vascular perfusion, particularly in the lower extremities, affects eight million persons in the US alone, at an estimated cost of $21 billion annually. Procedures are many, e.g., 500,000 per year, and result in over 100,000 amputations per year. Treatments include lytic therapy and surgery.

PVD patients require frequent vascular checks, and such are labor intensive and dependent on the skill of the operator. In some cases an ICU stay is required. Patients undergoing revascularization of the lower extremities often have long and morbid hospital stays, in part due to underlying comorbidities as well as the procedures themselves.

One challenge for the successful revascularization of patients with PVD is the monitoring of the extent and success of the revascularization. Post-procedurally patients often require intensive vascular monitoring to ensure vessel patency. This requires significant resources such as every-hour pulse checks and frequent physical exams. Presently, flow to the lower extremity arteries is typically assessed using Doppler or other ultrasound modalities. This approach has several limitations, including the need for highly trained personnel continuously available and capable of detecting and interpreting vascular Doppler signals, cost of the machines themselves, and the restrictions that point-in-time measurements intrinsically possess. Patients undergoing vascular procedures may also necessitate repeated interventions over several days, and serial measurements of flow pose significant manpower and logistical difficulties. In addition, intermittent point-in-time hand-held ultrasounds and larger ultrasound machines only provide quantitative information with fairly laborious and technically demanding measurements.

In addition to performing vascular monitoring to facilitate treatment of PVD, there are circumstances in which continuous and non-invasive monitoring of biological signals in central organs is of paramount importance for optimal patient care. This is because they play important roles in the whole-body system. The central organs have present challenges to continuous and non-invasive signal acquisition because they are buried under strongly attenuating tissue layers and because the object dimension ranges from several centimeters to several micrometers. Therefore, to capture biological parameters in central organs of interest, measurement strategies must possess both sufficient penetration depth and high spatial resolution. Presently available imaging techniques that achieve both, including radiographic imaging (e.g., X-ray computerized tomography), magnetic resonance imaging, and positron emission tomography, are widely used by trained practitioners to examine anatomy and function deep beneath the skin surface. However, due in part to their large footprint and high cost, these modalities are generally only accessible at a tertiary hospital or clinic.

There is thus a need for continuous and non-invasive hemodynamic and central organ monitoring capabilities accessible in both in-patient and out-patient environments.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

In one aspect, systems and methods according to present principles meet the needs of the above in several ways. In more detail, systems and methods according to present principles perform ultrasonic monitoring of blood vessels and central organs of a patient in a way that, according to one implementation, may be noninvasive, continuous, and accurate.

In further detail, disclosed are methods and devices according to present principles that pertain to a soft wearable transducer array for continuous, accurate, and noninvasive measurement of blood flow velocity waveforms, which can provide critical information about major organ activities and psychiatric state changes. The wearable ultrasonic device enables continuous measurement of the blood flow velocity waveform without constricting the natural movement of the subject. The device has similar mechanical properties to human skin and therefore can achieve a conformal and intimate contact with the skin, allowing accurate and stable measurements. Further, a phased array control mechanism facilitates focusing and steering the ultrasonic beam to any location with predefined incident angles, enhancing the signal-to-noise-ratio and removing user errors.

The disclosed systems and methods provide a radically different wearable ultrasonic device that is ultrathin and stretchable, which is made by combining soft electronic fabrication and advanced ultrasonic technologies. Many benefits may insure, according to implementation. First, this class of device allows an intimate and conformal contact at the device/skin interface, without external squeezing. Second, because of its lightweight and mechanical compliance, it can naturally adapt to human motion without noticeable mechanical loading. The ultrasonic array will therefore remain optimally aligned as desired. Third, using the phased array technique, the ultrasonic beam can be tilted with well-controlled incident angles at any location, obviating the need for exact placement of the device. In one illustrative application, this device can provide a new non-invasive technology for measuring blood flow velocity waveforms in patients with PVD requiring long-term, continuous waveform monitoring of lower extremity circulation. In other illustrative applications, this device can provide a new non-invasive technology for monitoring central organs, including, by way of example, tissues of the liver, lung and gastrointestinal tract, for perfusion monitoring and continuous surveillance or organs-at-risk for the patient.

Other advantages of implementations of the invention are described below, and others will be understood from the description that follows, including the figures and claims.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

FIGS. 21A, 21B and 21C show optical images of the wearable monitoring device.

FIGS. 24A, 24B and 24C show field II simulations of the beam convergence and deformation tolerance of phased array beamforming at various frequencies.

FIGS. 30A, 30B, 30C and 30D shows an enhancement of the orthogonal beam convergence in the x-y plane by increasing the number of rows of transducer elements in the phased array.

FIGS. 33A, 33B, 33C, 33D, 33E and 33F characterize the skin curvature on the human neck in typical postures.

FIGS. 34A, 34B, 34C, 34D and 34E show detailed skin curvature calculation protocols.

FIGS. 41A and 41B show raw RF signals of the tissue Doppler in the time domain and the corresponding human anatomy.

DETAILED DESCRIPTION

Figure 1A:
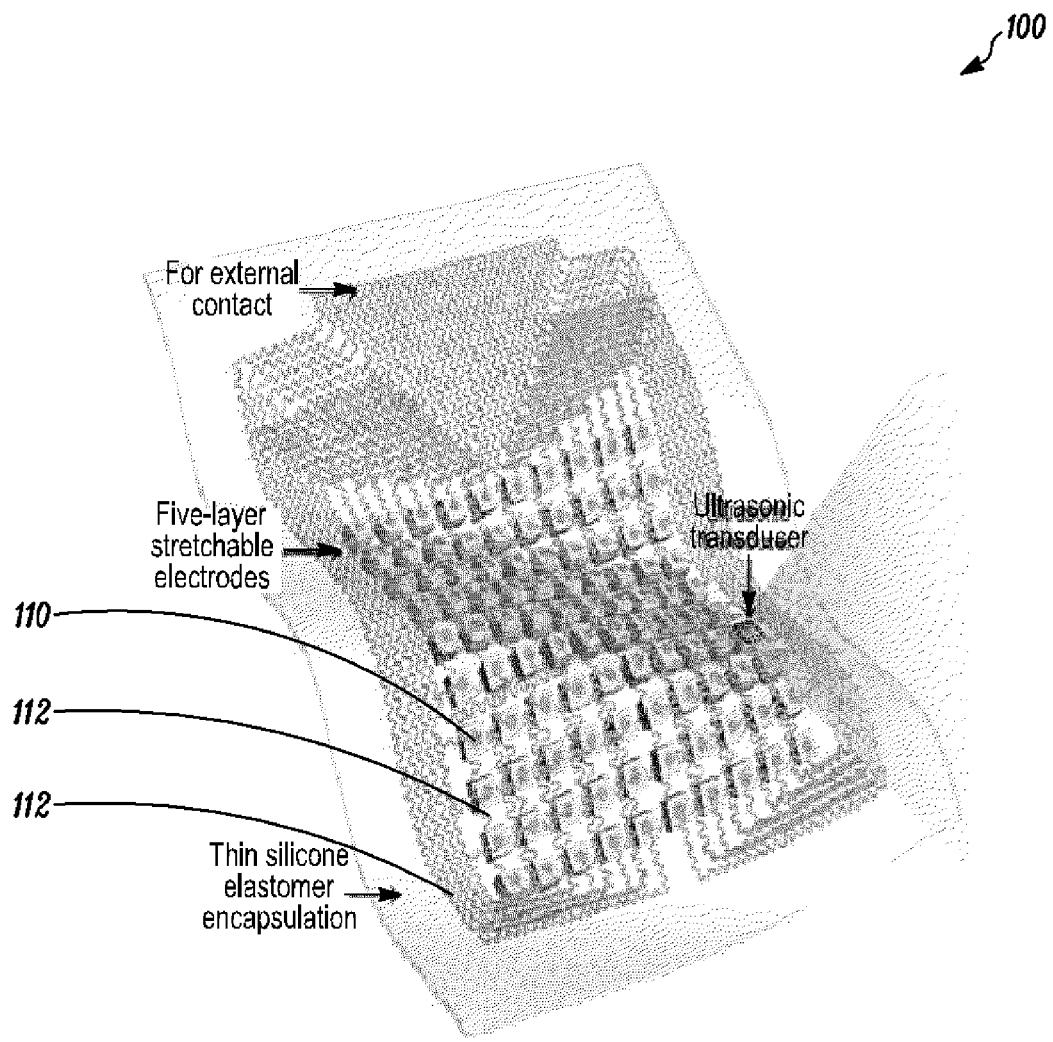
FIGS. 1A-1H schematically illustrate the design of one example of a stretchable ultrasonic transducer array that may be used as a wearable monitoring device.

Noninvasive monitoring devices that mount on the human skin are of great interest to modern health care, and a variety of wearable sensors have been demonstrated, such as temperature, pH, hydration, glucose/lactate, local field potentials, as well as the more common non- and minimally-invasive cardiac output monitors. Recently, novel approaches for ultrasonic diagnosis have been explored, either by integration with a specific geometry tailored to the detection surface, or by direct fabrication of a flexible ultrasonic transducer. The former requires an individualized design process for each workpiece; the latter usually involves interfacing of a bulk ceramic material with a soft medium, as seen in commercial ultrasound probes. Three significant limitations lie in these current flexible probes. First, the probes are flexible but not stretchable, which allows them to be in good contact with developable surfaces, such as cylindrical surfaces, but not on non-developable surfaces, such as spherical surfaces and the curvilinear human body. Second, due to their limited flexibility, they require constant pressure to be applied to the probes to maintain good contact. Therefore, they are usually connected with cumbersome holder assemblies during operation, which not only compresses the blood vessels but also compromises device wearability. Third, on nonplanar surfaces, frequent changes in the evaluation location and orientation are required, potentially resulting in beam distortion, making the technique highly operator-dependent.

Present systems and methods, in some cases implemented as a patch, may solve one or more of these difficulties.

As explained in more detail below, systems and methods disclosed according to present principles provide a soft wearable transducer array for continuous, accurate, and non-invasive measurement of blood flow velocity waveforms. The blood flow velocity waveform can provide critical information about the major organ activities and psychiatric state changes, which helps raise patient awareness, assists preventive care, and serves as the basis for personalized medicine. Conventional measurement protocols include catheter implants, which is invasive and risky, and Doppler ultrasonography, which is heavily user-dependent and often has errors and artifacts. Systems and methods according to present principles are distinct from the existing methods, because they offer several unique features. First, due to its low-profile form factors, the wearable ultrasonic device enables continuous measurement of the blood flow velocity waveform without constricting the natural movement of the subject. Second, this device has similar mechanical properties to the human skin and therefore can achieve a conformal and intimate contact with the skin, which allows accurate and stable measurements. Third, the phased array control mechanism facilitates focusing and steering the ultrasonic beam at any locations with predefined incident angles, which enhances the signal-to-noise-ratio and removes user errors for manual operations.

The stretchable transducer array is integrated with the phased array control circuit to achieve continuous and accurate recording of blood flow velocity waveforms. In this way the systems and methods according to present principles are advantageously able to use a soft, stretchable system to diagnose and monitor deep tissues under the skin. The availability of a comfortable, non-invasive blood flow monitoring device can make a fundamental difference in how related diseases are diagnosed and treated, which will have a direct impact on clinical practice. This wearable monitoring device may also shift the public perception of blood flow monitoring, promote preventive care, and provide unprecedented data streams for medical professionals, which will translate into significant reductions in associated mortality and healthcare costs.

Stretchable Ultrasonic Array Overview

One example of a stretchable ultrasonic transducer array 100 that can serve as a wearable monitoring device is shown in FIG. 1A. The piezoelectric transducers are arranged in a 10×10 array, connected by an "island-bridge" structured matrix. Each island hosts a rigid transducer element 110. The wavy bridges 112 can unfold to accommodate the externally applied strain, with limited strain on the components themselves. Therefore, the matrix is rigid locally but soft globally. Each transducer element in the array is individually addressable. The soft probe can consequently reconstruct the target morphology in multi-section images.

Figure 1B:
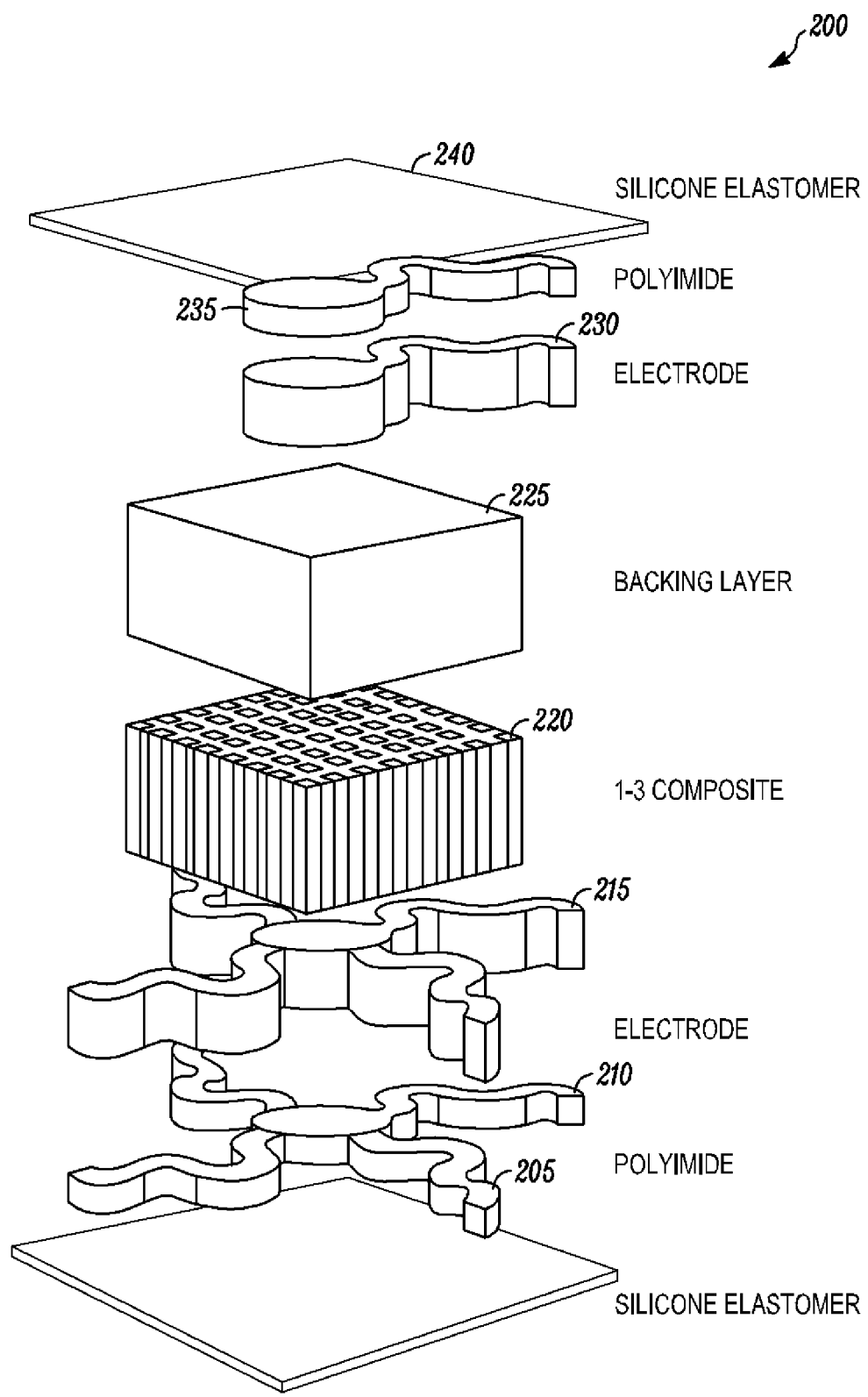
Figure 8:
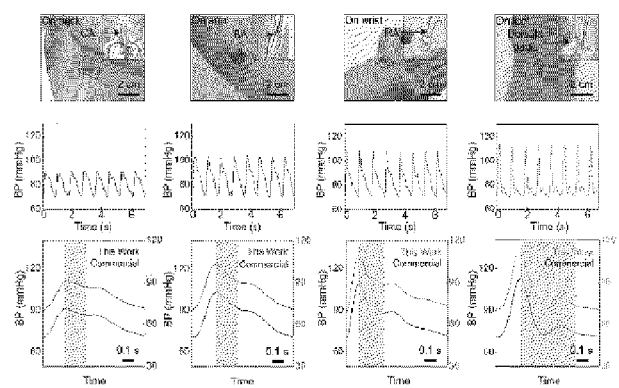
FIG. 8 illustrates a blood pressure waveform, from central to peripheral, that may be obtained using the wearable monitoring device described herein.
Figure 9:
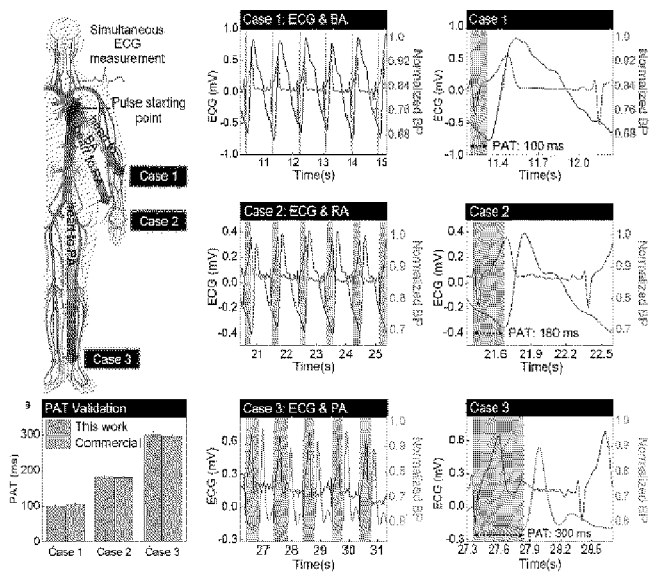
FIG. 9 shows the correlation between arterial stiffness and ECG.

FIG. 1B shows the exploded view of one transducer element 200. In this example both the substrate and superstrate are silicone elastomer thin films, whose low modulus (~70 kPa) and large stretchability (~900%) offer an extremely compliant platform to accommodate a diverse class of building blocks, such as piezoelectric elements, metal interconnects, backing layers, and solder paste. More specifically, in this example the transducer element 200 includes a substrate 205, a first patterned bilayer that includes a polymide layer 210 and an electrode 215, a piezoelectric electric 220, a backing layer 225, a second patterned bilayer that includes a polymide layer 235 and an electrode 230, and a superstrate 240. The elastomer substrate and superstrate thickness are 15 µm to provide both high acoustic performance and mechanical robustness of the device (FIGS. 8 and 9). As noted above, the islands and bridges are formed from patterned bilayers of Cu (20 µm)/polyimide (PI, 2 µm). The PI layer greatly enhances the bonding strength between the Cu and elastomer.

Figure 1C:
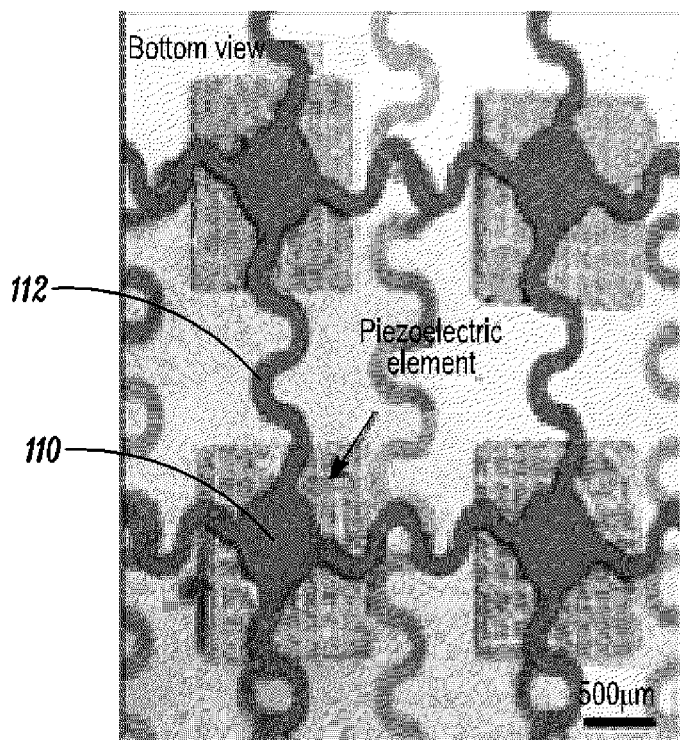
Figure 1D:
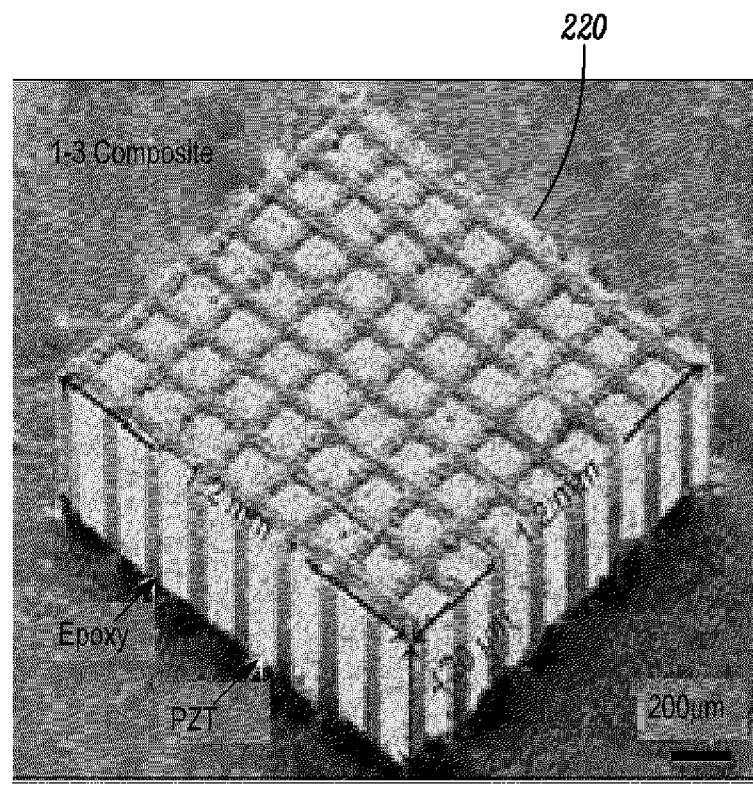
Figure 1E:
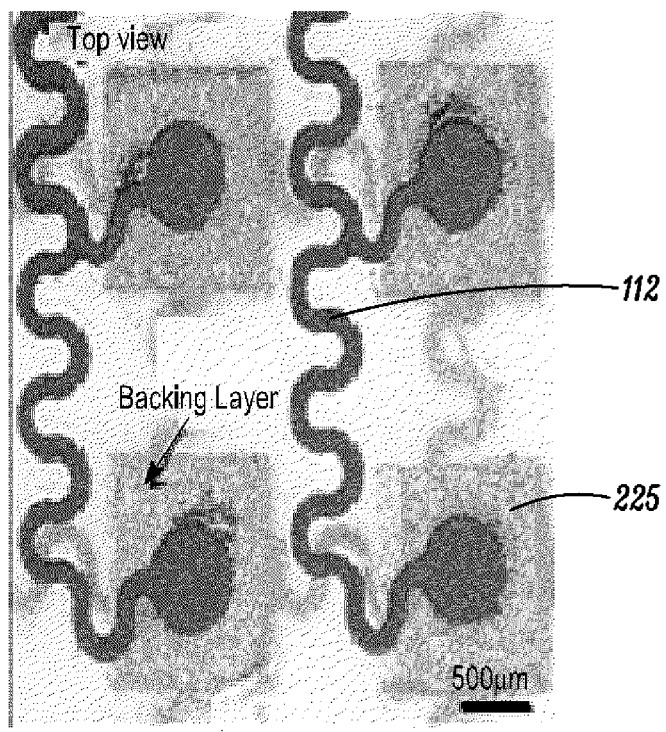

In one embodiment, piezoelectric 1-3 composites are chosen as the active material of the transducers. FIG. 1C shows an optical image of a bottom view four transducer elements 110 and FIG. 1D an SEM image of a piezoelectric 1-3 composite. Compared with an isotropic PZT, the anisotropic 1-3 composites have superior electromechanical coupling coefficients (thickness mode) that convert the majority of electric energy to vibration energy. In addition, the surrounding epoxy filler effectively suppresses transverse vibrations of PZT pillars, leading to enhanced longitudinal waves that go into the targeted objects. As seen in the optical image of FIG. 1E, the backing layer 225 effectively dampens ringing effects (excessive vibrations) of the piezoelectrics, which shortens spatial pulse lengths, and broadens the bandwidth and thus improves the image axial resolution. Silver epoxy and solder paste are used to build robust and electrically conductive interfaces of 1-3 composite/backing layer and 1-3 composite/metal electrode, respectively. Because of the close acoustic impedances of 1-3 composite (~20 Mrayl) and the targets to be tested (Al, ~18 Mrayl), the matching layer is not necessary in this study.

On the one hand, the pitch between adjacent transducer elements should be small to reduce side lobe and grating lobe artifacts in the acquired images. On the other hand, sufficient space between elements should be allocated to the serpentine interconnects for sufficient stretchability. In one embodiment, a pitch of 2.0 mm (1.2 mm×1.2 mm element footprint with a spacing of 0.8 mm between each column) is employed, which can achieve over 30% reversible stretchability. The high spatial resolution (~610 µm), negligible cross-talk level between adjacent elements (~−70 dB), and artifact-free images validates this pitch design. Within such limited footprints, the "island-bridge" electrode layout design is critical considering the large number of electrical connections needed for wiring the 10×10 array. An active multiplexing matrix under the ultrasound transducers could be a potential solution. However, the structural support materials introduced by the multiplexing matrix will negatively impact the device stretchability. Multilayered electrodes have been demonstrated, but the electrode design, passive dielectrics, and the substrate make the devices only flexible but not stretchable. To individually address the 100 transducer elements, a minimum of 101 electrodes with a common ground electrode is needed. It is very challenging to place this large number of electrodes within limited footprints using conventional single layer designs.

Thus, a multilayered electrode design has been developed based on the "transfer printing" method, which greatly enhanced the level of device integration compared to single layer designs. In one embodiment, this design includes five layers of "horse-shoe" configured serpentine electrodes. One electrode lies at the bottom of the transducers as a common ground layer. The other 100 electrodes are well aligned and distributed into four layers on top of the transducers as stimulating electrodes.

Thin films of silicone elastomer (35 µm thick) provide insulation and adhesion between adjacent layers. The central area of each layer is selectively protected using customized masks during fabrication to allow the islands (bonding pads) to be exposed to the array elements. Laser ablation is used to quickly pattern serpentine structures. Wires with widths of 150 µm to 40 µm remain intact and discontinuities start to arise when the wire width is 30 µm.

Figure 1F:
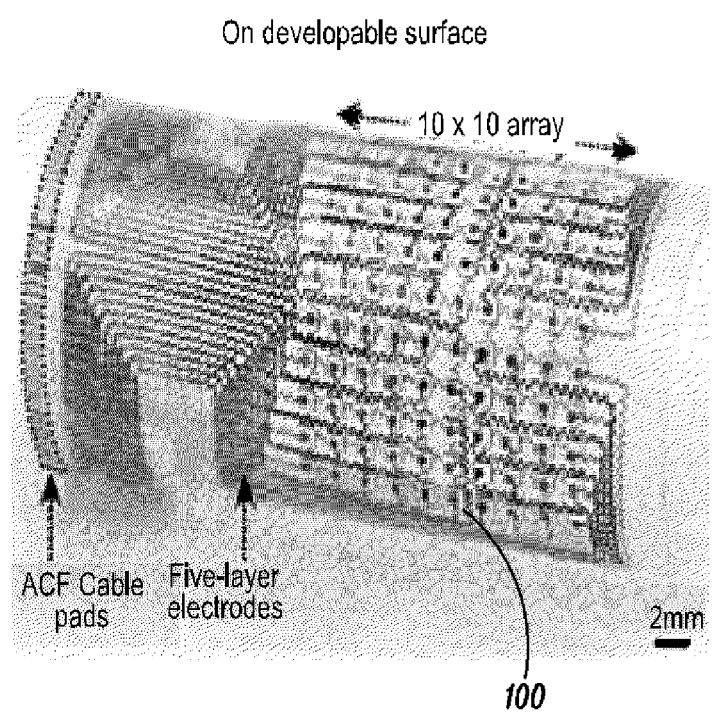
Figure 1G:
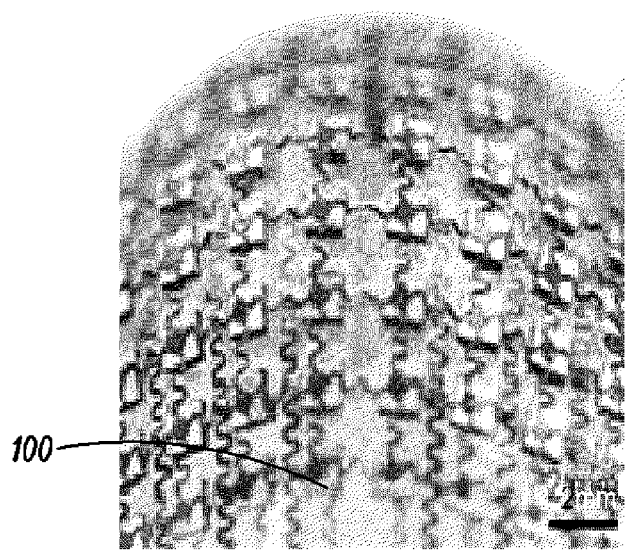
Figure 1H:
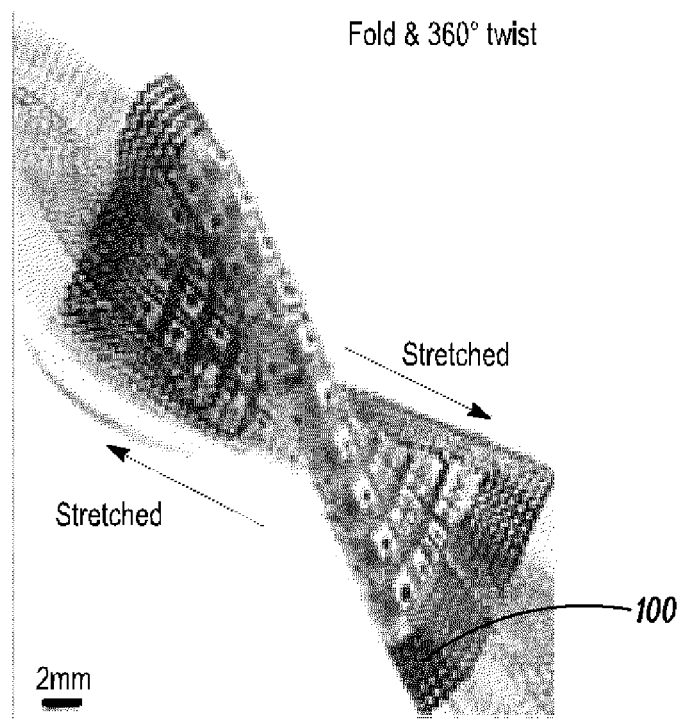

Compared with microfabrication methods by lithography and etching, which requires sophisticated fabrication processes, chemicals, shadow masks, and a cleanroom environment, laser ablation is time efficient, low cost, and offers high throughput. The as-fabricated final device is seen in FIGS. 1F to 1H, which highlight its excellent mechanical properties when conforming to developable (cylindrical) and non-developable (spherical) surfaces, and under mixed modes of folding, stretching and twisting. In particular, FIGS. 1F-1H respectively show optical images of the stretchable device when bent around a developable surface, wrapped on a non-developable surface, and in a mixed mode of folding, stretching, and twisting, showing its mechanical robustness.

The wearable monitoring described above device can easily achieve conformal contact to various nonplanar surfaces of real components, such as pipeline elbows, wheel edges, and rail tracks, as well as human skin. Due to its excellent mechanical compliance and lightweight (e.g., 0.15 g), the device described herein can maintain intimate and stable contact with the human skin both mechanically and acoustically in different body postures with pure van der Waals force.

By balancing geometrical and electrical designs, the wearable monitoring device or patch may have an ultrathin thickness (~500 two orders of magnitude thinner than existing medical ultrasonic probes). The ultrasonic transducer material to be used may be 1-3 piezoelectric composite, composed of periodic piezoelectric microrods embedded in a passive polymer. This substantially increases the longitudinal coupling coefficient k33 by suppressing the shear vibrating k31 modes. To accommodate the rigid components, an "island-bridge" structure may be used. Specifically, the rigid components are integrated with the islands, and the wavy serpentine metal interconnects serve as the bridges. The bridge can bend and twist to absorb the externally applied strain. Therefore the entire structure is rigid locally in the islands (with a footprint of 1.2×1.2 mm2), but stretchable globally by adjusting the spacing between the rigid islands during the bending, stretching, and twisting processes. The result is a natural interface that is capable of accommodating skin motion with minimal mechanical constraints, thereby establishing a robust, non-irritating device/skin contact that bridges the gap between rigid planar traditional electronics and the soft curvilinear biological objects.

Figure 2:
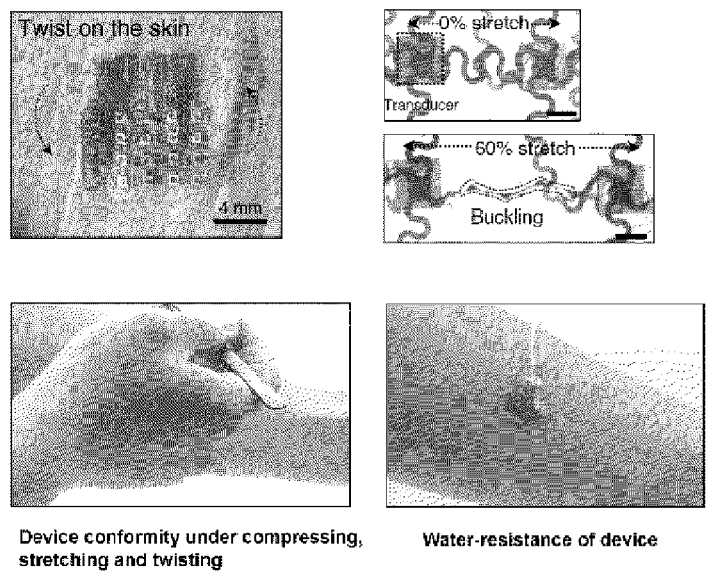
FIG. 2 illustrates the conformity of the wearable monitoring device under compressing, stretching and twisting, as well as its water-resistance.

FIG. 2 illustrates the conformity of the wearable monitoring device under compressing, stretching and twisting, as well as its water-resistance.

Additional details concerning the aforementioned example of the wearable monitoring device that is formed from the stretchable ultrasonic transducer array described above may be found in U.S. application Ser. No. 16/477,060, which is incorporated by reference herein in its entirety.

Continuous Blood Flow Velocity Monitoring

Figures 3A, 3B:
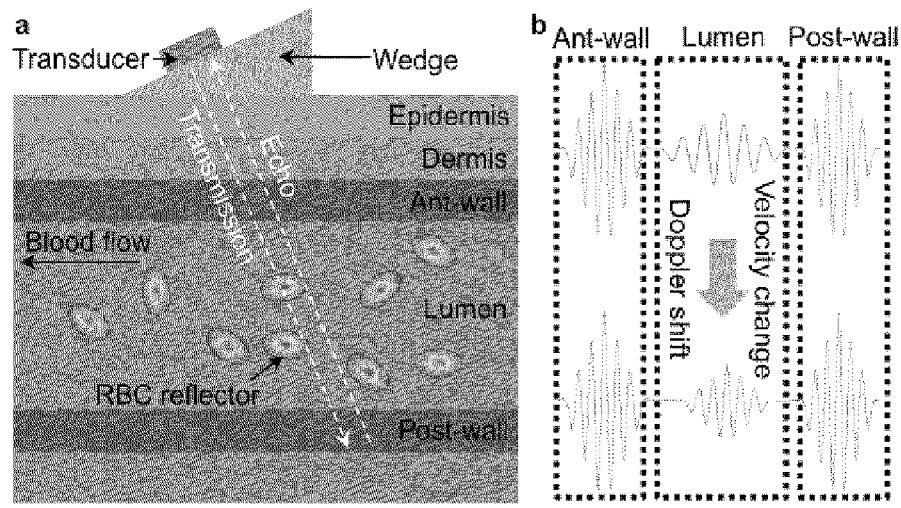
FIG. 3a schematically illustrates a single transducer element oriented at an incident angle for detecting blood flow by the Doppler shift.
FIG. 3b is a schematic diagram showing the echo signals from the lumen in FIG. 3a FIG. 4a schematically illustrates the working principle of a phased array with a parabolic time delay profile and the feedback mode to the operator.

In one implementation, the conformable piezoelectric transducer array described above may be used as a wearable monitoring device to monitor the blood flow rate in the artery by the Doppler effect. FIG. 3a schematically illustrates a single transducer element oriented at an incident angle for detecting blood flow by the Doppler shift. FIG. 3b is a schematic diagram showing the echo signals from the lumen in FIG. 3a, as represented by the reduced spatial pulse rate (SPL) when the blood flow increases.

Two parameters that are closely related to the transducer performance are the piezoelectric composite resonance frequency and the acoustic impedance of the substrate. Independently, a higher resonance frequency is expected to minimize the signal's SPL, which is the parameter characterizing the duration of the signal pulses in the time domain, thereby improving the axial resolution of the blood vessel diameter measurement. The resonance frequency can be tuned by controlling the thickness of the 1-3 piezoelectric composite. For instance, a thickness of 420 µm yields a resonance frequency of 3.5 MHz. The optimal acoustic impedance of the substrate layer minimizes acoustic wave reflection at the device/skin interface, and can be tuned by the composition of the substrate material. performance with a systematic design of experiment approach, to eventually optimize the single element performance.

As shown in FIG. 3a, an incident angle can be created with a wedge to obtain the Doppler shift caused by blood flow. In use, the transducer emits ultrasound and penetrates through epidermis and dermis layers and then reaches the vessel lumen. The signal will gain Doppler shift by interacting with the flowing red blood cell (RBC) reflectors. The shifted signals can be decoded to obtain blood flow velocity waveform by three steps. The first step is to demodulate the signals by Hilbert transform, which is to extract Doppler-shifted frequencies from the carrier frequency. The second step is to eliminate the noise introduced by instrument and vessel movement with high-pass and low-pass filters[32]. The third step is to extract the sampling point sequentially by a window function, complex fast Fourier transform (CFFT), and envelope detection. Then, the flow velocity can be calculated as:

$$v = \frac{c}{2w_0 T} w$$

in which, c is the ultrasound velocity in blood, $w_0$ is the carrier frequency, w is the Doppler shift of the signal, and T is pulse repetition period.

After obtaining the blood flow velocity waveforms, key parameters of interest, including the mean flow velocity and waveform morphology that corresponds to cardiac events such as systolic peak and dicrotic notch, can be compared to the commercial Doppler vascular imaging equipment used in clinics. The comparison results will be used as guidelines for optimizing the performance of the single transducer element in subsequent cycles of the design of experiment.

In some embodiments the conformable piezoelectric transducer array may be used as a wearable phased array ultrasonic probe. The terms "wearable monitoring device" and "wearable phased array ultrasonic probe" will be used interchangeable herein. Phased array ultrasonic transduction by a two-dimensional (2D) array of individually controllable transducers can result in better focusing and higher quality signals. In comparison with single element transducers and conventional ultrasonic probes, the wearable monitoring device with phased array control according to present principles has two major benefits. First, unlike single element transducers that incorporate noise generated at all complex interfaces and barriers in the tissues, phased array ultrasonic probes focus the ultrasonic beam to increase the signal-to-noise ratio. Second, conventional ultrasonic probes require experienced clinicians to locate the target vasculature. The present wearable monitoring device with phased array control, in some implementations, can electronically steer the beam to the desired vessels automatically without changing the physical positions of the transducer, allowing beam alignment with the vessel. An optical fiber may be employed to precisely map the three-dimensional coordinates of each transducer in the array. The transducer coordinates may be then be used to design the time delay profile for the phased array.

Figure 4:
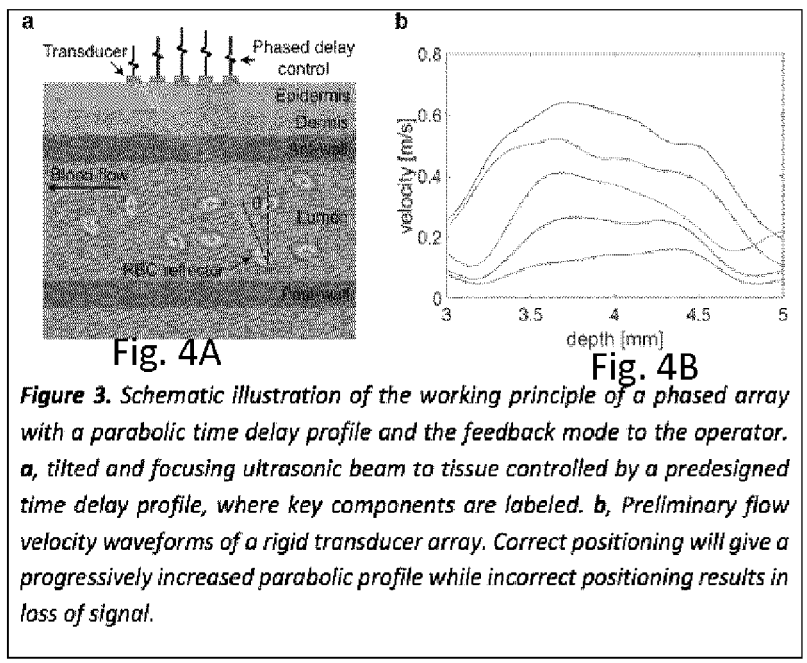
FIG. 4b shows the preliminary flow velocity waveforms of a rigid transducer array.

FIG. 4a schematically illustrates the working principle of a phased array with a parabolic time delay profile and the feedback mode to the operator. As shown, the tilted and focusing ultrasonic beam is directed to tissue controlled by a predesigned time delay profile, where the key components are labeled in the figure. FIG. 4b shows the preliminary flow velocity waveforms of a rigid transducer array. Correct positioning provides a progressively increased parabolic profile while incorrect positioning results in loss of signal.

Figure 5:
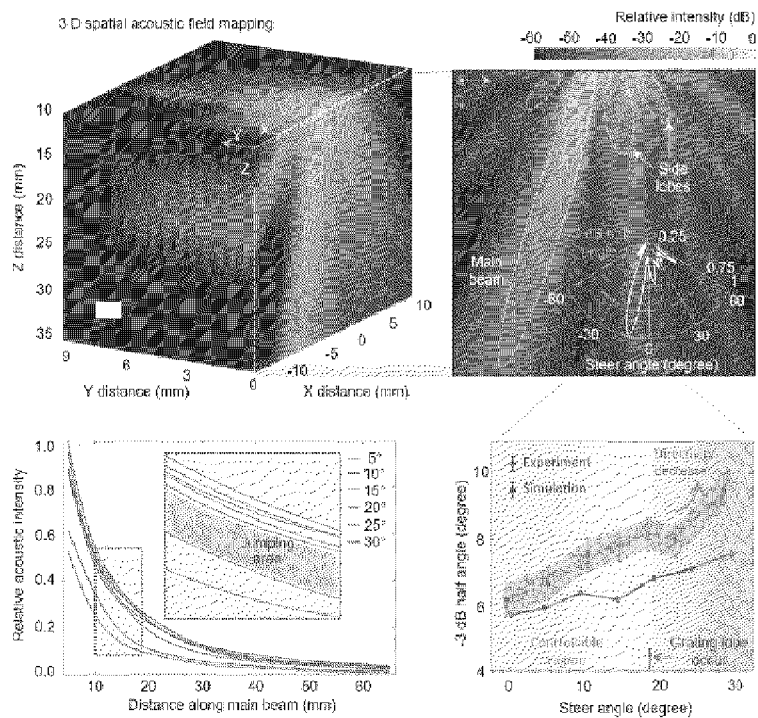
FIG. 5 illustrates the described beam tilting and focusing of the wearable monitoring device.

Phased array ultrasonic transduction by a two-dimensional (2D) array of individually controllable transducers can result in better focusing and higher quality signals. Successful prototypes based on single transducers have already been successfully tested on other vessels of similar depth and orientations (e.g., radial and carotid arteries) in human subjects with comparable accuracy to results achieved by professional sonographers. FIG. 5 illustrates the described beam tilting and focusing of the wearable monitoring device.

In comparison with single element transducers and conventional ultrasonic probes, the wearable monitoring device with phased array control according to present principles has two major benefits. First, unlike single element transducers that incorporate noise generated at all complex interfaces and barriers in the tissues, phased array ultrasonic probes focus the ultrasonic beam to increase the signal-to-noise ratio. Second, conventional ultrasonic probes require experienced clinicians to locate the target vasculature. The present wearable monitoring device with phased array control, in some implementations, can electronically steer the beam to the desired vessels automatically without changing the physical positions of the transducer, allowing beam alignment with the vessel. An optical fiber may be employed to precisely map the three-dimensional coordinates of each transducer in the array. The transducer coordinates may be then be used to design the time delay profile for the phased array.

One illustrative control algorithm for achieving automatic beam alignment with the phased array controls each ultrasonic transducer element independently. By adjusting the time-delay of activating each element or pixel in the array, constructive ultrasonic interference patterns can be achieved with presumably any location and tilting angles. To achieve the maximum response, vessel depth and its orientation relative to the transducers can be determined by an algorithm rather than a brute-force search. Vessel depth can be identified by the time of flight measurement in the perpendicular direction of each sensor. The orientation alignment can be achieved by comparing the maximum position in one direction with different columns. The beam steering and alignment procedure using calculated parameters requires highly accurate time domain measurement and control. The time-digital-conversion technique using Field Programmable Gate Array (FPGA) or high-speed strobe sampling with programmable delay line can be used to realize the best accuracy in peak detection and frequency analysis for Doppler shift measurements.

A high voltage (e.g., about 100 V) and programmable pulse-delay circuit may be used to activate each transducer element. In some embodiments commercially-off-the-shelf (COTS) integrated circuit chips may be used as building blocks. Overall, the complexity of the circuit can be reduced in some implementations by utilizing analog chips or deploying System on Chip integrated circuit components to improve the system efficiency and minimize the cost. A micro power DC-DC converter can be used to generate high voltage (>100 V) from low voltage sources such as a small battery or inductive power transmission. In the phased array method, the high voltage needs to be delivered individually to each transducer element with well-controlled time delay profile. In some implementations a general microcontroller with non-volatile memory can be used to generate the voltage pulses with a pre-defined time delay profile.

The accurate representation of the distribution and relative position of each transducer element in the array is important for the beamforming process. Without location mapping of the elements on curved surfaces, a reduction of detection accuracy and an increased chance of false focusing can occur. A shape sensing fiber may be used to map the location of each element using optical frequency domain reflectometry. When transmitting in the fiber, the light will be reflected by an optical grating, and the reflected light wavelength is determined by the periodicity of the grating. The change in fiber geometry will result in a change of periodicity of the grating. Therefore, the reflected light wavelength will be changed. During the mapping process, the sensing fiber will be attached to the soft ultrasound transducer array. The measured positions along the fiber can be computed by the associated sensing system. Elements in the 2D array of transducer elements can be measured row by row. Finally, the positional data can be resampled to 4×5 points to compute the coordinates of each element.

Figure 6:
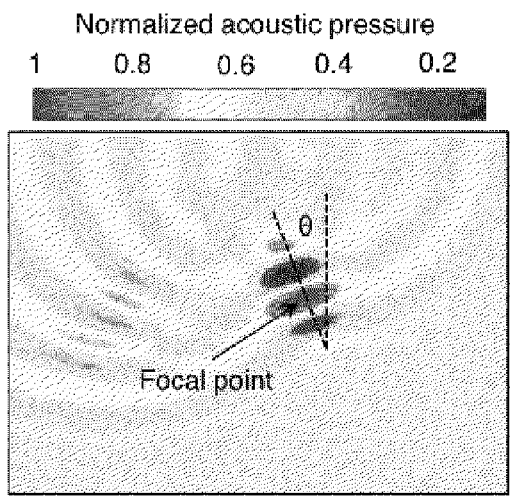
FIG. 6 shows simulation results by COMSOL Multiphysics to demonstrate beam focusing with titling angle θ without a wedge as seen in the single element measurement.

Once the phased array is enabled time-delayed control the ultrasound beam can focus at a predefined depth with a stable Doppler incident angle, yielding an optimum signal-to-noise-ratio and reduced user dependency. The phased array performance has been simulated by considering a particular piezoelectric material type (1-3 composite material), a particular size (1.2×1.2 mm$^2$ in footprint), and a particular pitch (2.2×2.2 mm$^2$). A parabolic electric signal time delay profile was used to construct a focused 30° tilting angle. The result is seen in FIG. 6, which shows simulation results by COMSOL Multiphysics to demonstrate beam focusing with titling angle θ without a wedge as seen in the single element measurement.

Figure 7:
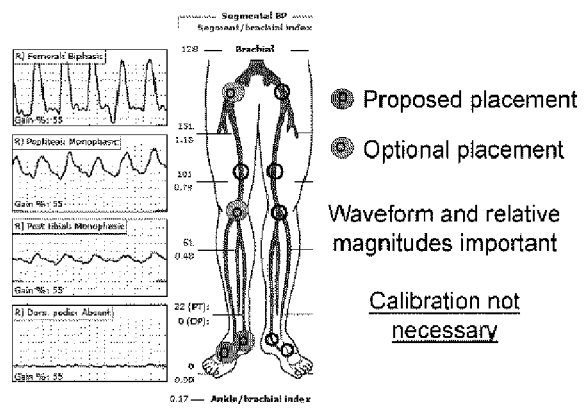
FIG. 7 shows some illustrative places where the wearable monitoring device patches or sensors may be located on a patient.

The wearable monitoring devices described herein may be advantageously used in a wide variety of different applications. For example, they may be deployed for patients with PVD who require monitoring of lower extremity perfusion. The measurement of pulse pressure in key lower extremity arteries may be targeted as is typically measured for patency in patients with PVD, including branches of the femoral, popliteal, dorsalis pedis (DP), and posterior (PT) and anterior tibialis (AT). FIG. 7 shows some illustrative places where the wearable monitoring device patches or sensors may be located on a patient. Because the cost of fabrication is low and the addition of multiple sensors is trivial, the number of sensors used per patient per extremity can be selected as needed; for instance, in many cases three sensors per extremity may be suitable—a larger proximal artery and more distal arteries (e.g., DP, PT) that are usually targets of vascular intervention. Although the proposed device is capable of measuring flow (and thus cardiac output) in addition to waveform analysis, because the measurement of flow to the distal extremities does not typically require the reporting of exact hemodynamic parameters (e.g., systolic and diastolic pressures), this obviates the issue of device calibration and accuracy that hampers universal adoption of other minimally invasive cardiovascular monitors.

Figure 10:
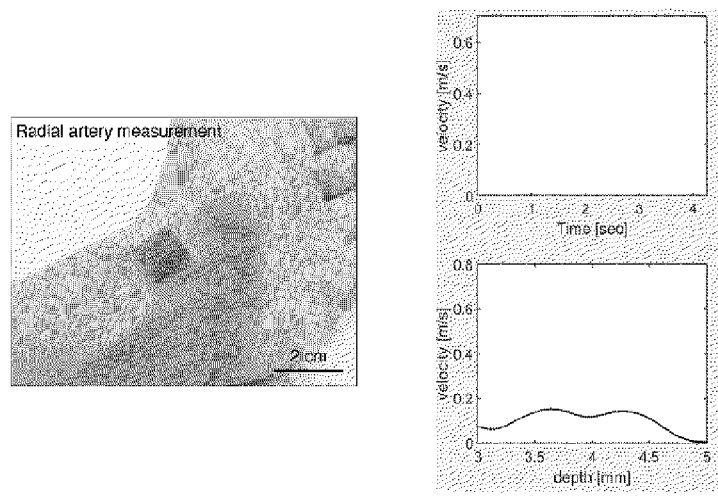
FIG. 10 shows the use of the wearable monitoring device described herein for hemodynamic monitoring to obtain a blood-flow profile.
Figure 11A:
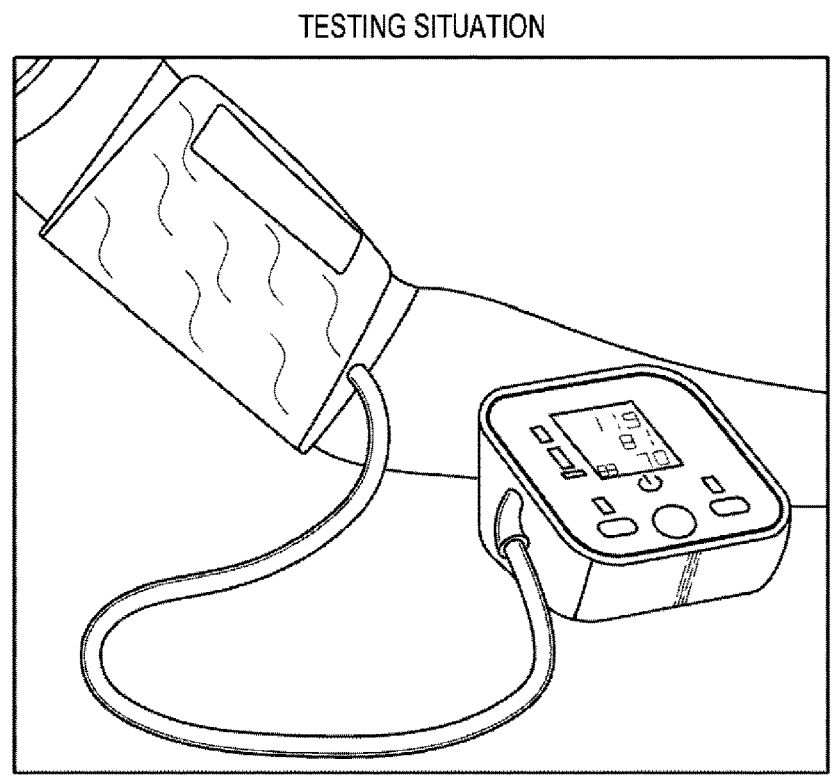
FIG. 11 shows the use of the wearable monitoring device described herein for blood occlusion monitoring.
Figure 11B:
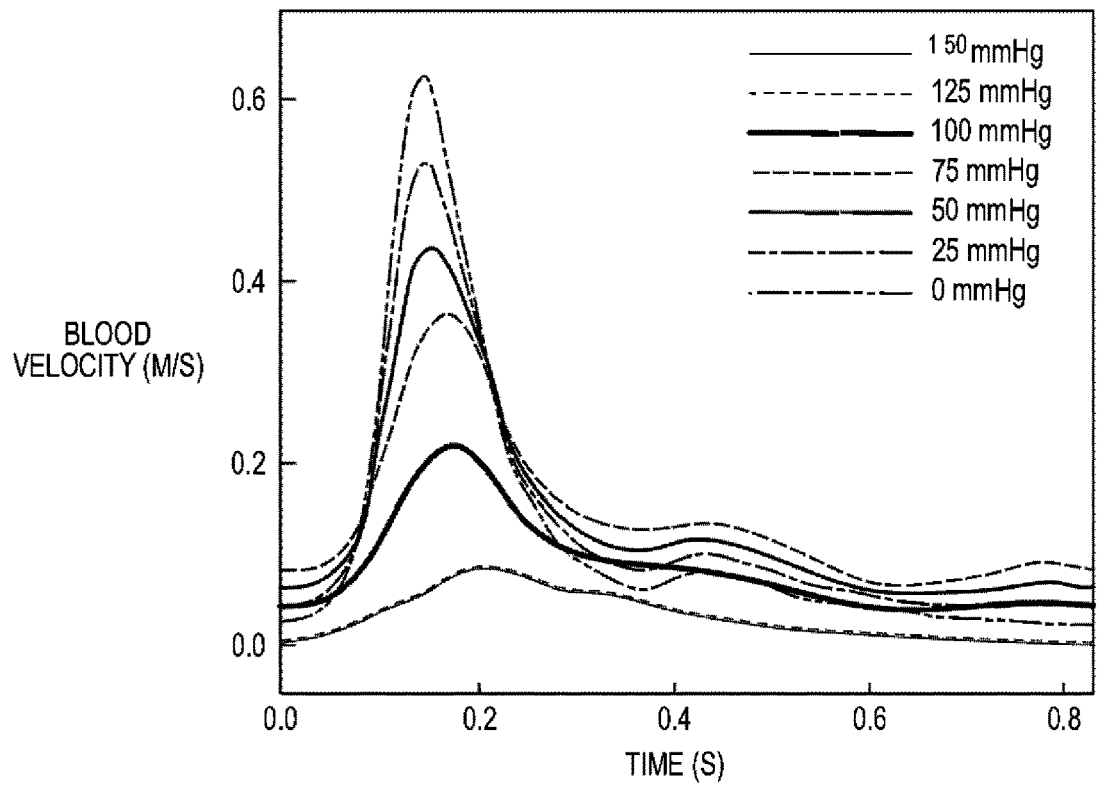
Figure 12:
FIG. 12 illustrates a blood flow spectrum.
Figure 12:
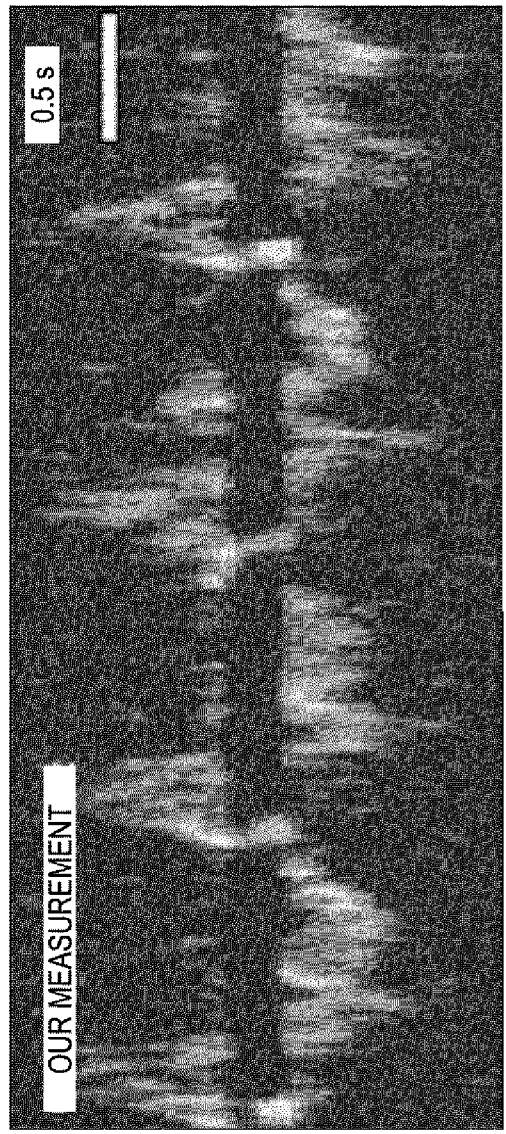
Figure 12:
Figure 12:
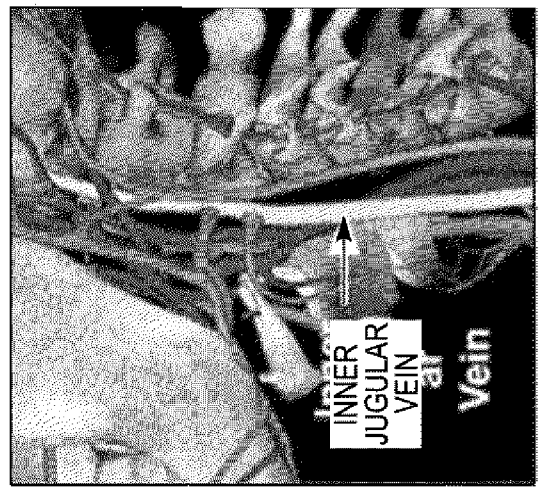

FIG. 8 illustrates a blood pressure waveform, from central to peripheral, that may be obtained using the wearable monitoring device described herein. FIG. 9 shows the correlation between arterial stiffness and ECG. FIG. 10 shows the use of the wearable monitoring device described herein for hemodynamic monitoring to obtain a blood flow profile. Likewise, FIG. 11 shows the use of the wearable monitoring device described herein for blood occlusion monitoring. FIG. 12 illustrates a blood flow spectrum.

Figure 13:
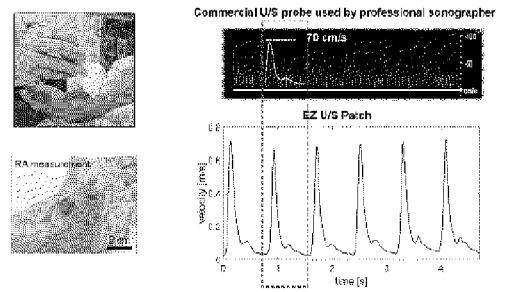
FIG. 13 compares the test results on the radial artery of a patient using a conventional ultrasound probe as obtained by a professional sonographer and as obtained using the wearable monitoring device described herein.
Figure 14:
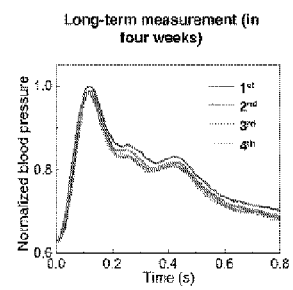
FIG. 14 illustrates the durability and reproducibility of the measurements obtained by the wearable monitoring device over a period of four weeks.

The wearable monitoring device described herein provides a wide variety of advantages. For instance, in some embodiments the controller may be configured to be operator independent with autonomous focusing and the automatic location of target vessels. FIG. 13 compares the test results on the radial artery of a patient using a conventional ultrasound probe as obtained by a professional sonographer and as obtained using the wearable monitoring device described herein. The figure illustrates that the wearable monitoring device with phased array control provides a comparable level of accuracy without the need for operator expertise. FIG. 14 illustrates the durability and reproducibility of the measurements obtained by the wearable monitoring device over a period of four weeks. Other general advantages include that the wearable monitoring device is non-invasive, continuous, versatile, easy-to-use, safe, accurate, affordable, water resistant, not an infection risk, and well tolerated.

It is noted that intimate interfacial contact is a key to efficient ultrasound wave propagation. Phased array ultrasonic transduction, enabled by a two-dimensional (2D) array of individually controllable transducers, can result in better focusing and higher quality signals. From mechanical simulations in our previous published results (Xu, S et al., Science 344, 70 2014), dividing a rigid bulk material into islands reduces strain localization and enables biaxial stretchability. The convergence of these three rationales leads to the current technical approach—using a 2D array of soft piezoelectric transducers that adapts to the natural human movements for accurate blood flow velocity measurement.

The phased array transducer array described herein has mechanical properties similar to the human skin and can acquire signals with much better signal-to-noise-ratio than can a single transducer element. As previously mentioned, due to its excellent mechanical compliance and lightweight (e.g., 0.15 g), the device described herein can maintain intimate and stable contact with the human skin both mechanically and acoustically in different body postures with pure van der Waals force. The measurement results can be very accurate, showing minimal user-dependency. In some cases, however, some arteries may be too shallow for ultrasonic focus. For example, the depth of the radial artery is only about 5 mm under the skin, which means the deflection angle could be too big for a small array, especially when the directivity of each transducer is high due to the high resonance frequency. Due to the existence of side lobes of the periodically structured 1-3 composite ultrasonic transducers, one possible solution would be to use the side lobes if the vessel is very shallow. Alternatively, each transducer element may be designed with a smaller footprint for better beamforming performance.

Systems and methods according to present provides provide new stretchable systems to continuously and accurately monitor blood flow velocity waveforms in patients with PVD. The systems and methods limit the need for highly-trained personnel while at the same time greatly improve patient safety and most importantly, outcomes. The systems and methods can be greatly expanded to other areas of cardiovascular hemodynamic monitoring that may benefit from inexpensive, non-invasive, small foot-print, accurate devices capable of continuous, long-term, real-time monitoring of hemodynamic performance. Other markets, some of which are described below, may include non-invasive cardiac output monitoring and consumer health monitoring.

Central Organ Monitoring

Figure 15A:
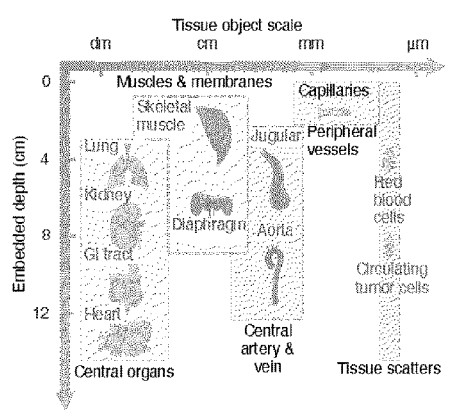
FIG. 15A is a graph illustrating the depths underneath the skin (vertical axis) and the dimensions (horizontal axis) of representative human tissues or organs of interest.

As previously mentioned, the central organs have two major characteristics that present challenges to continuous and non-invasive signal acquisition. First, they are buried under strongly attenuating tissue layers. FIG. 15A is a graph illustrating the depths underneath the skin (vertical axis) and the dimensions (horizontal axis) of representative human tissues or organs of interest. The wearable sensor needs to have long penetration depths and resolve structures at multiple scales. Second, the object dimension ranges from several centimeters to several micrometers. or clinic.

Ultrasound is particularly suitable as the sensing modality to target hemodynamic signals in central organs because of its remarkable penetration depth in tissues and the ability to resolve micrometer-scale red blood cells (RBCs). A single wearable ultrasonic transducer (with a footprint of e.g., 0.9 mm×0.9 mm×0.4 mm in l×w×t) can only achieve a ~3-4 cm penetration depth and sense a region directly beneath it (i.e., line of sight detection). Considering the non-linearity of human anatomy, it is very challenging to target specific regions with a single-transducer configuration.

When the wearable monitoring device is configured as a phased array ultrasonic probe as described herein, it can detect multiscale biological objects (from centimeter to micrometer) with a penetration depth of up to about 17 cm in the human body. By controlling the time-delay profile of each ultrasonic transducer in the array, the device uses phased array transmit beamforming to produce a focused ultrasonic beam. The resulting beam can be as much as 267 times higher in intensity compared to the beam produced by the synthetic aperture technique based on a single-transducer configuration, which significantly enhanced the signal-to-noise-ratio (SNR) of the acquired reflection signals. With phased array receive beamforming, the high-quality reflection signals received by each transducer channel can be aligned and added up to further enhance the signal-to-noise (SNR) ratio. With dynamic control of the pulse time profile of the transducer array, the focal length and steer the direction of the ultrasonic beam can be controlled within a wide range of incidence angles (from e.g., −20° to 20°), allowing active targeting of specific organs/tissues of interest in the human body.

To demonstrate the use of the wearable monitoring device to monitor central organs, the results of detecting left and right human heart ventricular Doppler signals approximately 4-14 cm beneath the skin will be presented. The ultrasonic beam can be steered to intercept the blood flow at a sufficient Doppler angle, which allows for accurate flow spectrum recording. Combining the blood flow and vessel dimension measurements allows the estimation of the cerebral blood flow in real-time.

Figure 15B:
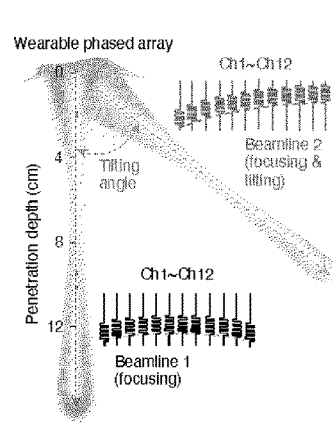
FIG. 15B, schematically illustrates the working principle of phased array ultrasonic beamforming.
Figure 15C:
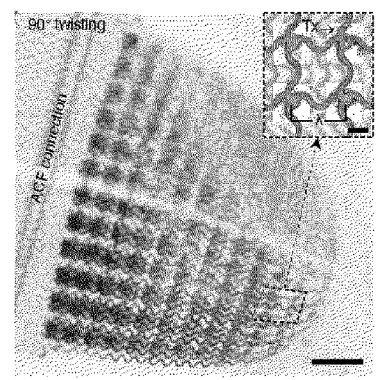
FIG. 15C shows an optical image of this wearable phased array ultrasonic probe twisted 90° laterally.

The particular configuration of the wearable phased array ultrasonic probe that is employed for the continuous and non-invasive hemodynamic monitoring of human central organs is determined by the required beam penetration depth and spatial resolution (see FIG. 15A), and the need to steer the beam to actively target a tissue, as schematically illustrated in FIG. 15B, which shows the working principle of phased array ultrasonic beamforming. With a pre-designed pulse time profile, the transducer array is able to focus and steer the ultrasonic beam to target biological structures of interest. Beamline 1 illustrates the exceptional penetration depth of a focused ultrasonic beam (up to 14 cm in human tissue). Beamline 2 illustrates the focusing and steering of the ultrasonic beam by adjusting the pulse time delay profile of the transducer array. As explained below, this consideration leads to a configuration, in one particular illustrative embodiment, of a 2 MHz wearable phased array ultrasonic probe with a 0.8 mm transducer element pitch and an array size of 12 by 12 to focus and steer the ultrasonic beam. FIG. 15C shows an optical image of this wearable phased array ultrasonic probe twisted 90° laterally, with the stretching of the interconnects clearly visible, demonstrating the ability to conform to the skin surface of the soft device. The inset shows a zoomed-in image of four transducer elements in the array, with an island-bridge design and a pitch of approximately one ultrasound wavelength according to the Huygens' principle. The scale bars in FIG. 15C and the inset are 2 mm and 300 µm, respectively.

Based on Huygens' principle, the pitch of the phased array elements needs to be about the same as the wavelength of the ultrasound wave to allow for high-quality beam convergence. The requirements on penetration and resolution places competing requirements for the frequency of the ultrasound: higher frequency ultrasound waves have a better resolution but lower penetration, and vice versa. A frequency of 2 MHz may be chosen as the center frequency to reduce the frequency-dependent linear attenuation while maintaining sufficient resolution. For sensing tissue structures about 10-17 cm beneath the skin, a center frequency of around 2 MHz with a corresponding wavelength of 770 µm in soft tissues is preferably used. The pitch of the device is therefore designed to be 800 µm. In addition, a relatively low frequency reduces the sensitivity to device curvature changes when integrated on the human body.

The array size is determined by the penetration requirement. A larger array size allows higher ultrasonic power output and therefore higher penetration depth. As explained above in connection with FIG. 1, each transducer element in the device was connected with serpentine wires to achieve system-level stretchability. With a total thickness of 650 µm, the device has a low form factor and can be twisted or stretched. The wearable phased array ultrasonic probe can easily conform to non-developable surfaces. This particular device can be reversibly stretched equal-biaxially up to 16%, beyond which plastic deformations in the interconnects are observed.

Figure 16A:
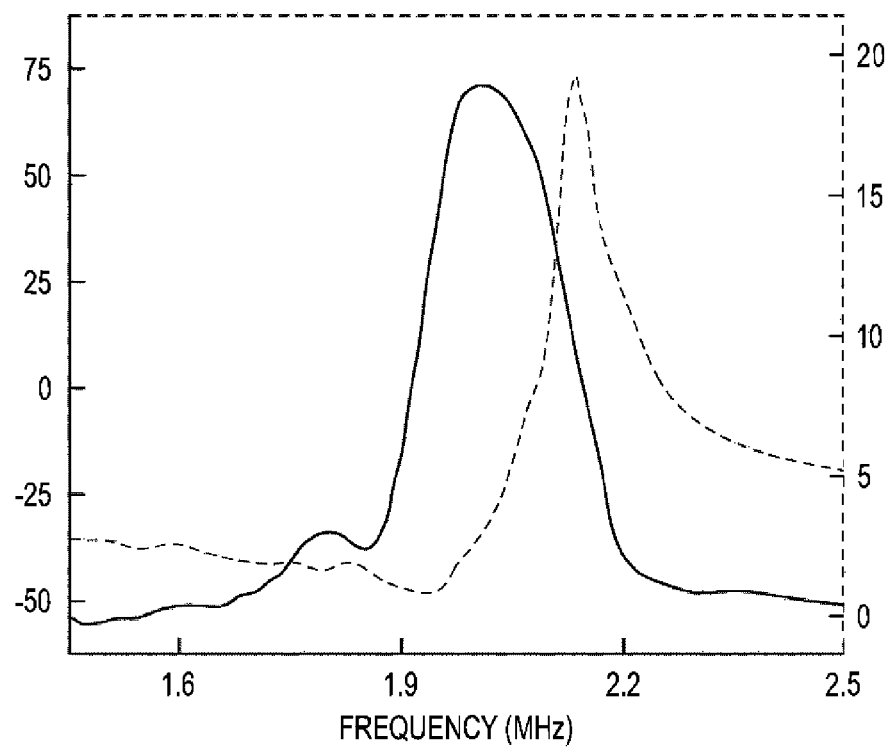
FIG. 16A shows the impedance and phase angle spectra of a single transducer element.
Figure 16B:
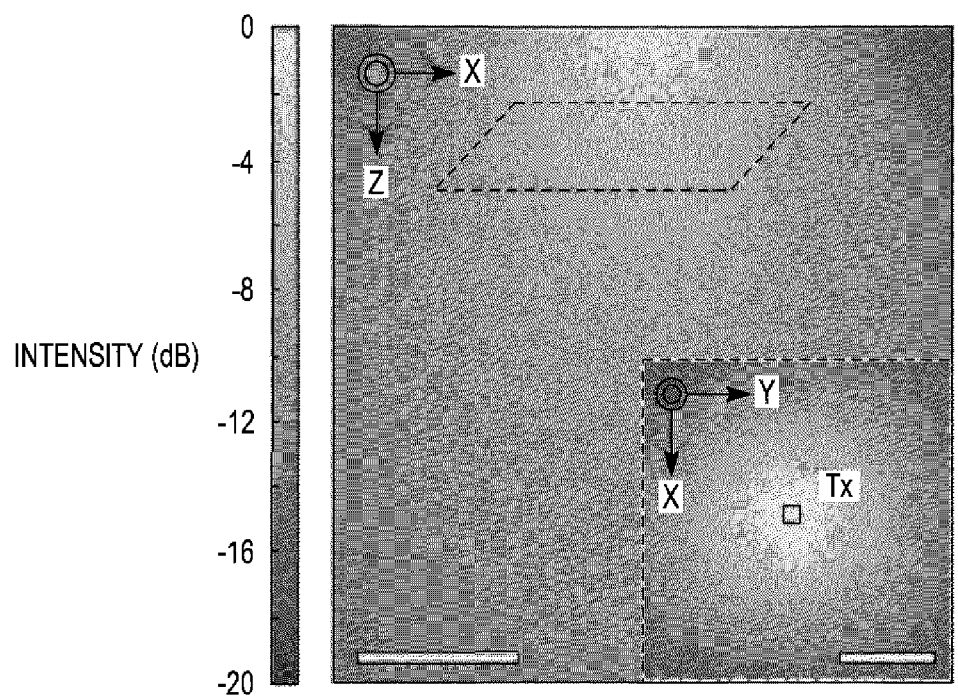
FIG. 16B shows a mapped ultrasonic field of a single transducer element.

FIG. 16A shows the impedance and phase angle spectra of a single transducer, which indicates high electromechanical coupling comparable to commercially available ultrasonic devices. The center frequency and electromechanical coupling coefficient of the transducer elements across the entire array are highly consistent. FIG. 16B shows a mapped ultrasonic field of a single transducer (2 MHz, 0.55 mm×0.55 mm×0.6 mm in l×w×t). The inset is the cross-section of the insonation region in the x-y plane, with the position and size of the transducer (Tx) marked by a square. Scale bars in the image and the inset are 5 mm and 3 mm, respectively. The ultrasonic field mapping of the single transducer clearly shows the beam spreading in the x-z plane. When more than one transducer is excited, ultrasonic waves from adjacent transducers interfere to create a converged beam. A lower transducer frequency has been found to lead to a larger insonation area and better convergence.

Phased array ultrasonic beamforming allows for control of the focal length and direction of the ultrasonic beam. Each transducer element is excited by predesigned electric pulses, and control of the pulse time profile tunes the ultrasonic wave interference, and therefore the focal length of the produced ultrasonic beam (beamline 1 in FIG. 15B). At the focal point, the beam intensity is 89 times higher at 2 MHz, and 267 times higher at 7.5 MHz compared to the beam from a single transducer, which significantly enhances its penetration depth. Similarly, the pulse time profile can also be designed to steer the beam direction to a desired incidence angle from −20° to 20° (beamline 2 in FIG. 15B). The ability to focus on a selected spot in the three-dimensional (3D) space enables the targeting of a particular tissue in the sensing range.

Figure 16C:
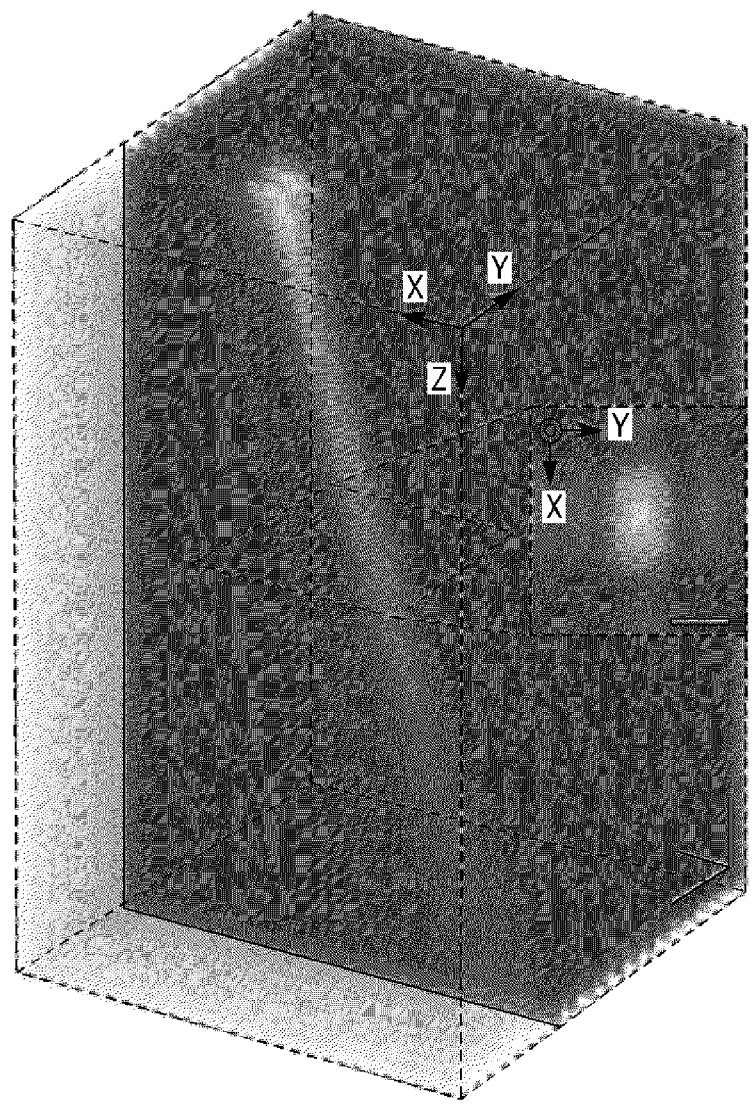
FIG. 16C shows the mapped ultrasonic field of the wearable phased array probe in 3D.

FIG. 16C shows the mapped ultrasonic field of the wearable phased array probe in 3D. The scale bars in all directions are 1 cm. The inset shows the zoomed-in cross-section of the ultrasonic field at the focal point, demonstrating good beam convergence in the x-y plane. The scale bar is 1 cm. The three-dimensional mapping of the ultrasonic beam in FIG. 16C shows the high penetration depth and excellent beam convergence of the device. The designed array allows for 167 mW/cm$^2$ ultrasonic energy density to be delivered to the central organs, which is within the FDA-defined safe range (720 mW/cm$^2$ for vascular and 430 mW/cm$^2$ for cardiac applications). The beam directivity, which determines the energy density in the main beam direction, can be controlled by tuning the focal length. A long focal length can narrow the beam and improve the beam directivity in the deep tissue region, leading to a better resolution in targeting and sensing. Compared to a commercially available rigid phased array ultrasonic probe (i.e., Verasonics P4-2v), the beam from the wearable monitoring device described herein has a similar directivity in large working range.

Figure 16D:
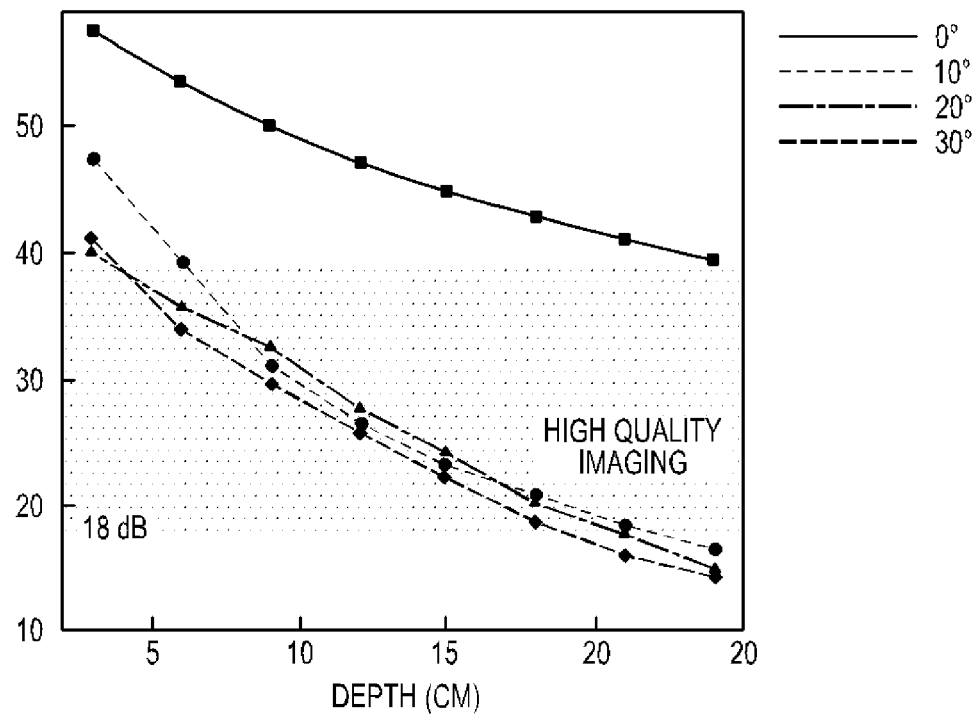
FIG. 16D shows the signal-to-noise ratio as a function of depth when each transducer element is excited with multiple lines/rows and multiple pulses.

The axial resolution of the device can be increased by improving the focus and increasing the number of transducers in the array, such as from 12 in this particular example to 128 as in the case of commercial devices. To further enhance the directivity and intensity of the beam, and therefore the lateral resolution and SNR of the acquired data, each transducer can be excited with multiple lines/rows and multiple pulses. The associated benefits are threefold. First, multi-line/rows excitation generates more focused ultrasonic beams, which not only provide a higher lateral solution but also carry more intense energy, and thus produce a stronger scattered intensity from small tissues, leading to a higher SNR. As indicated in FIG. 16D, the SNR can be characterized along the main beam with different incidence angles of the device in a water tank. For high-quality imaging, the SNR should be over 18 dB. The results demonstrate the excellent performance of the phased array, with an SNR over 18 dB even at 20 cm deep for all incidence angles in this example. Second, multi-pulse has a much smaller bandwidth (e.g., 15 pulses has a bandwidth of 5.72% compared to 24.58% for a single pulse), which leads to higher sensitivity to the Doppler shift from small reflectors. Third, multi-pulse enhance the tolerance of the beamforming output to device deformation.

Conventional phased array ultrasonic beamforming has only been implemented in rigid and bulky probes because the phase aberration induced by array deformation in a soft device remains a great challenge. When a soft device deforms with human movements, each transducer element will shift from their standard locations, causing deviations in the ultrasonic interference and thus the beam output. Although advanced auto-correction methods can measure the location of each element and minimize the phase aberration, the dynamic movement of the human skin poses significant challenges for accurate real-time tracking of transducer coordinates. In this illustrative example in which a relatively low frequency of 2 MHz is chosen, the array element shifts are negligible compared to the long wavelength, which minimizes the sensitivity of the beam output to device deformation in any direction. Note that lower frequencies will decrease the reflection from small tissues due to frequency-dependent Rayleigh scattering. With multipulse excitation, this problem can be overcome. Moreover, the longer ultrasonic pulse length enables a higher probability of interference, and therefore beamforming is enhanced, which further minimizes the sensitivity of the beamforming to device deformation.

Figure 16E:
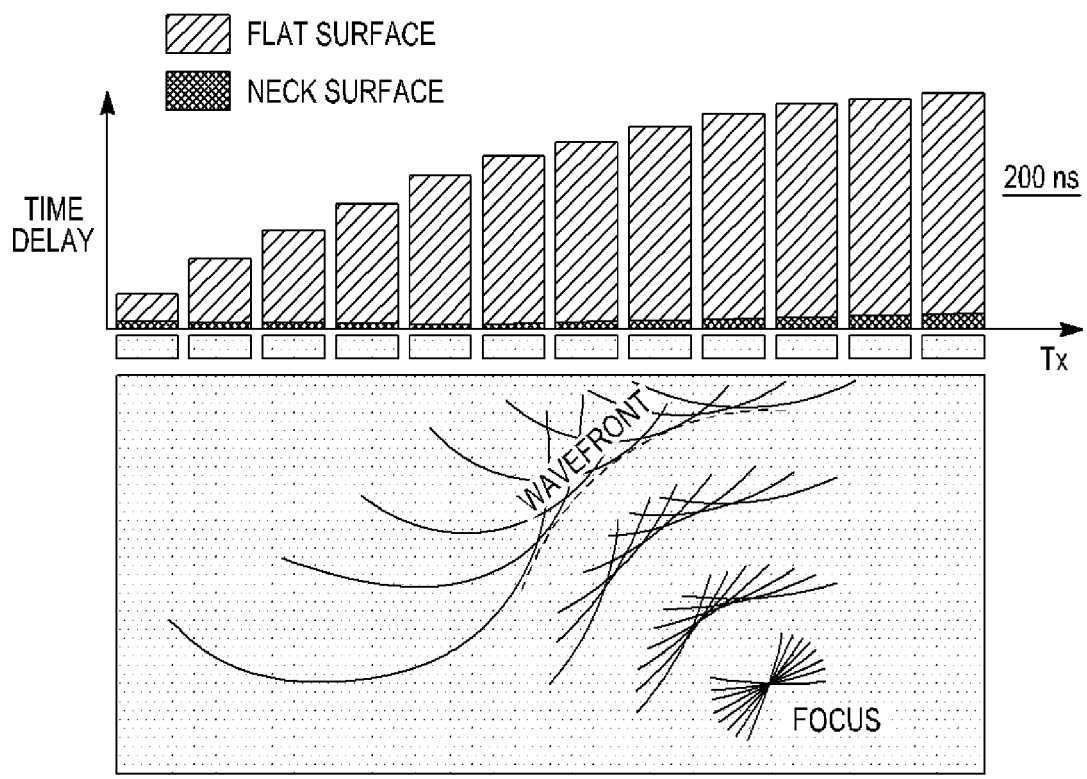
FIG. 16E illustrates how the use of a low frequency compensates for the phase aberration induced by deformation of the wearable monitoring device.

To determine how the low frequency compensates for the phase aberration induced by device deformation, the phase error created by the curvature of the human skin was investigated First, with a 3D scanner, the minimum radius of curvature of a human neck surface in different postures, about 4.2 cm, was recorded. As shown by the bars in FIG. 16E, the required pulse time profile for a linear transducer array was calculated to create a synthetic wave-front in a certain focal area with no array deformation. Next, the required pulse time profile is calculated to create the same wavefront with the array deformed to a radius of curvature of about 4.2 cm. The deviations from the former profile are also marked by the bars in FIG. 16E. The largest deviation is 14.2 ns, corresponding to a phase aberration of 4.26%, which occurs for the transducer element on the edge of the array. The deviation is only 1.13 ns for the transducer in the center, corresponding to a phase aberration of 0.06%. Therefore at 2 MHz, the phase aberration from typical neck skin curvature is relatively small, and therefore has minimal effect on the phased array beamforming.

Figure 16F:
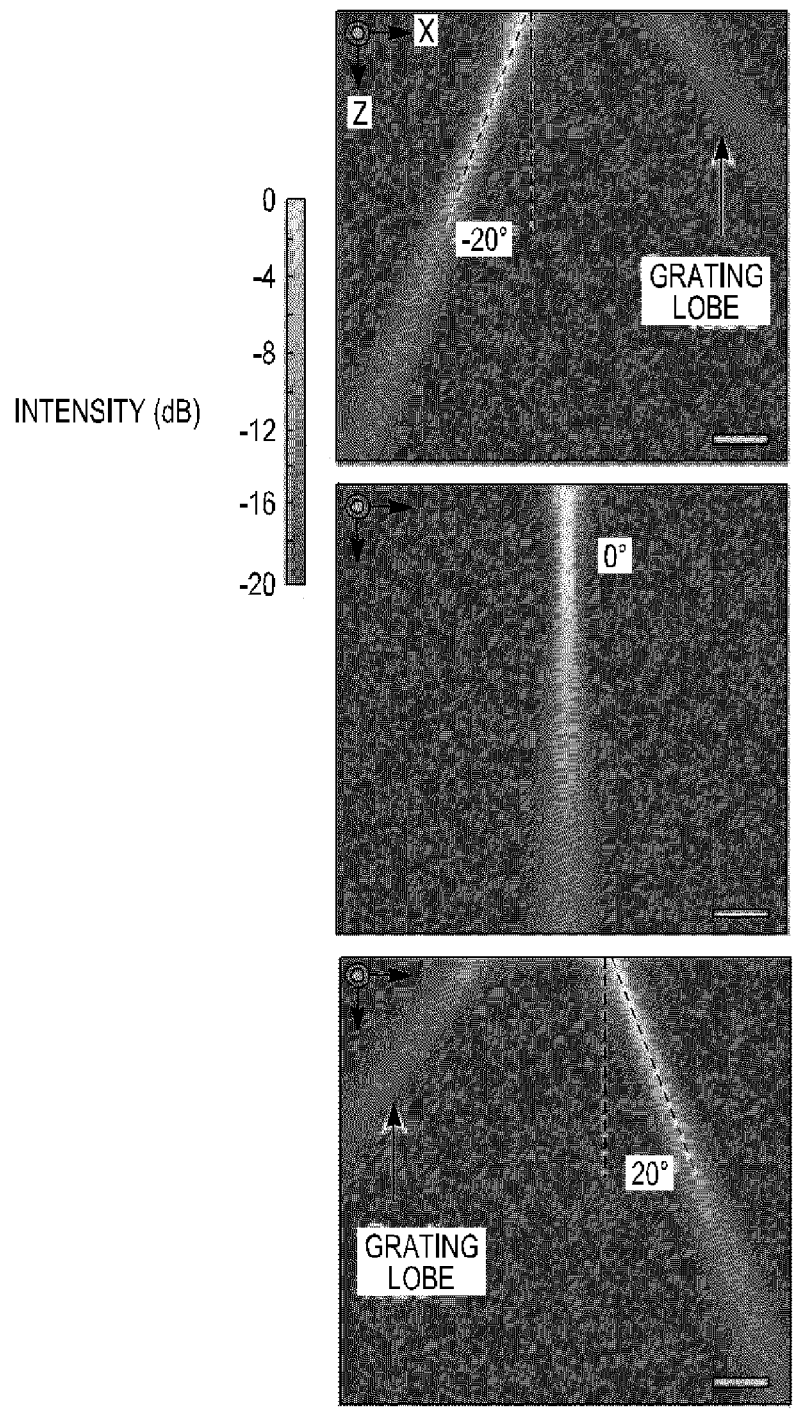
FIG. 16F show the experimental results obtained when the wearable phased array ultrasonic probe is placed on a skin-mimicking phantom replicated from the human neck.

To further investigate the beamforming of the wearable phased array ultrasonic probe on a complex surface of an in vitro model, the device is laminated on a skin-mimicking phantom replicated from the human neck. Experimental results show that on both planar and neck surfaces, the ultrasonic beam can be steered in a wide range of incidence angles. As FIG. 16F indicates, a grating lobe appears as the incidence angle is increased. The working range of an ultrasonic device for high-accuracy sensing is defined as the range in which the intensity of the grating lobe is at least −15 dB weaker than the main beam. When the device follows the contours of the phantom with about a 4.2 cm minimum radius of curvature, the working range is from −20° to 20°, with a 0.1° accuracy of the testing system (Verasonics). Besides bending, the probe performance is also characterized against in-plane deformation. The results show that the beamforming performance is excellent under 20% tensile or compressive strain, which is the maximum strain of the skin on the human neck in a natural posture.

With strong penetration and well-controlled beam focusing and steering characteristics even on curved surfaces, the wearable phased array ultrasonic probe has broad applications for targeted central organ monitoring. Here two illustrative applications of the wearable monitoring device in hemodynamics monitoring are demonstrated: (1) cardiac tissue Doppler imaging (TDI) 4 to 14 cm beneath the skin, and (2) blood flow spectrum recording (with RBCs several micrometers in size) for quantitative analysis of central cardiovascular dynamics.

The wearable phased array ultrasonic probe described herein may also be used to monitor cardiac function continuously and noninvasively. The conventional approach to the non-invasive direct measurement of cardiac function is echocardiography, which has become the gold standard. However, echocardiography is mostly conducted in clinics only, which means only data at the point of care are captured. Typical echocardiographic probes are rigid and bulky, which are impractical for chronic patient monitoring. Moreover, obtaining high-quality data from these probes requires extensive training of the operator. Long-term echocardiographic measurement of cardiac functions has therefore not been available, and cardiac monitoring relies on probes that are either more invasive (e.g., pulmonary artery catheter) or probes that provide indirect estimates of cardiac functions based on relevant parameters (e.g., arterial waveform analysis, impedance changes, and aortic Doppler). These problems can be addressed by the wearable phased array ultrasonic probe.

Since ventricular structures are located about 3-14 cm beneath the human skin, ventricular signals experience significant attenuation in both the transmitting and receiving process. The quality of the received signal depends not only on the transmitting beam intensity, but also on the receiving performance of the transducer array. To enhance the SNR of the received signal, phased array receive beamforming is used, a reverse process of the transmit beamforming.

Figure 17A:
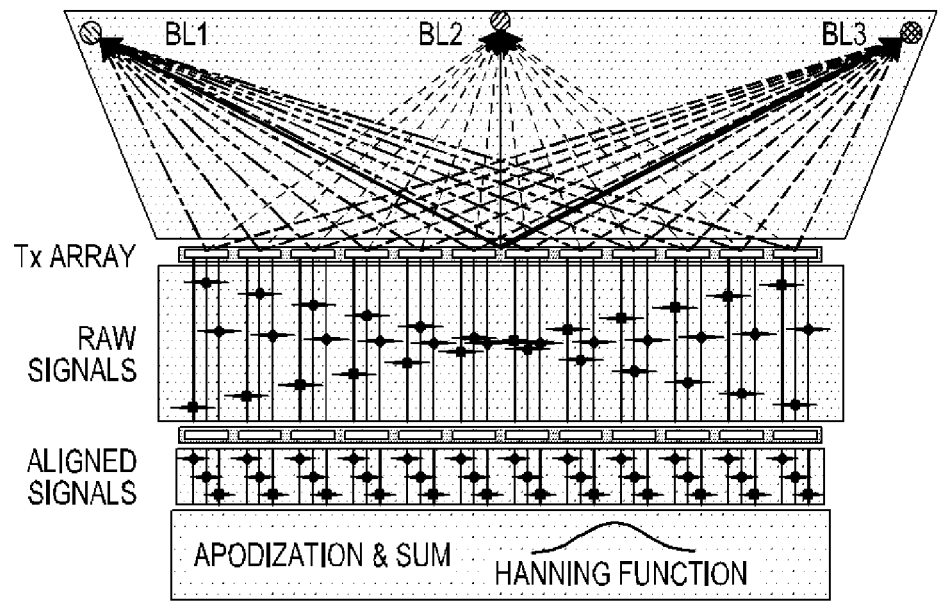
FIG. 17A illustrates the working principle of phased array receives beamforming.

FIG. 17A illustrates the working principle of phased array receives beamforming. The SNR of the signal can be enhanced by aligning and adding up the raw signals received by each transducer channel. The signal can be a weighted sum with the choice of proper window functions (e.g., the Hanning function) to further enhance the contrast. That is, phased array receive beamforming takes into account the signals received by all transducers in the array and their phase differences, and then adds up the signals to reconstruct a stronger echo with a higher SNR. With phased array transmit and receive beamforming, the wearable monitoring device can be used to detect objects placed with various orientations up to 17 cm deep in water and tissue-mimicking phantoms. The results are comparable with the outcome of a commercial probe.

Figure 17B:
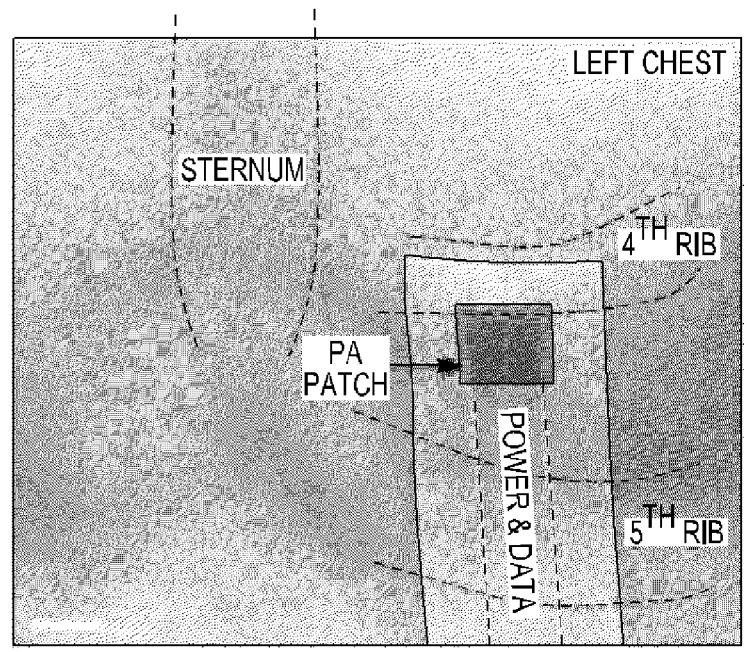
FIG. 17B is an optical image of the wearable monitoring device on the human chest with key components labeled in the image.
Figure 17C:
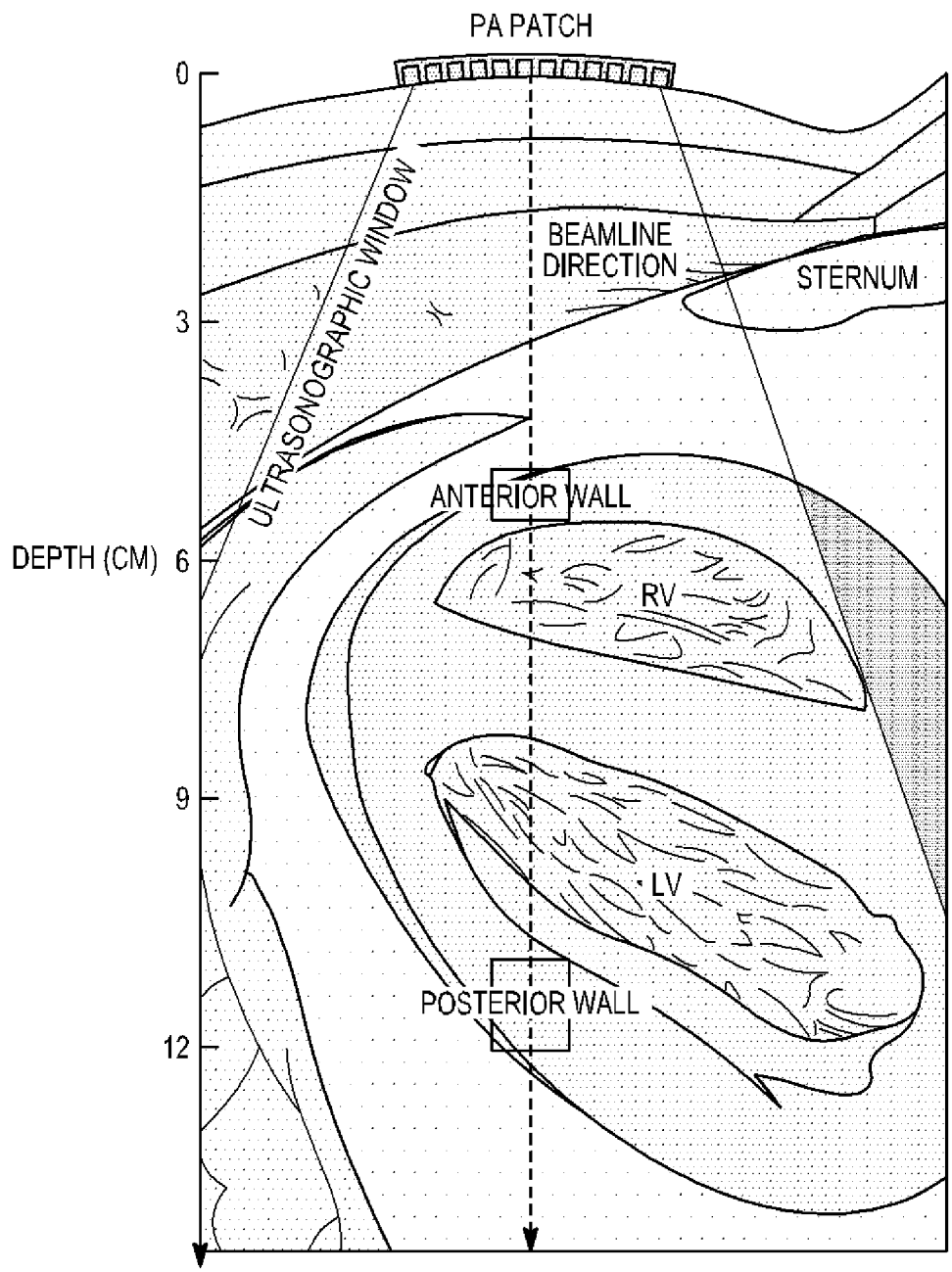
FIG. 17C is a schematic illustration of the ultrasonographic window used in cardiac activities monitoring.

FIG. 17B is an optical image of the wearable monitoring device on the human chest with key components labeled in the image. The scale bar is 1 cm. FIG. 17C is a schematic illustration of the ultrasonographic window used in cardiac activities monitoring, with the 0° beamline labeled. The anterior wall of the right ventricle and the posterior wall of the left ventricle are labeled. In FIGS. 17B and 17C the wearable phased array ultrasonic probe is placed between the $4^{th}$ and $5^{th}$ ribs for cardiac monitoring.

Figure 17D:
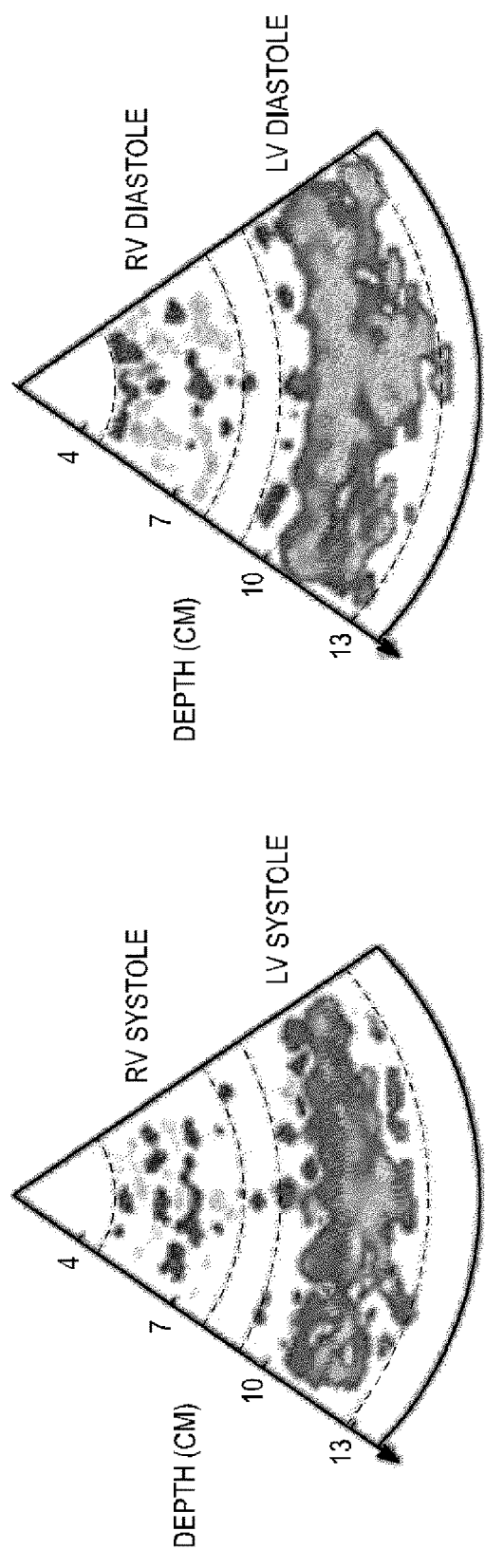
FIG. 17D is a Doppler spectrum showing the ventricles (left panel) and the relaxation of the two ventricular walls in the diastole phase (right panel)
Figure 17E:
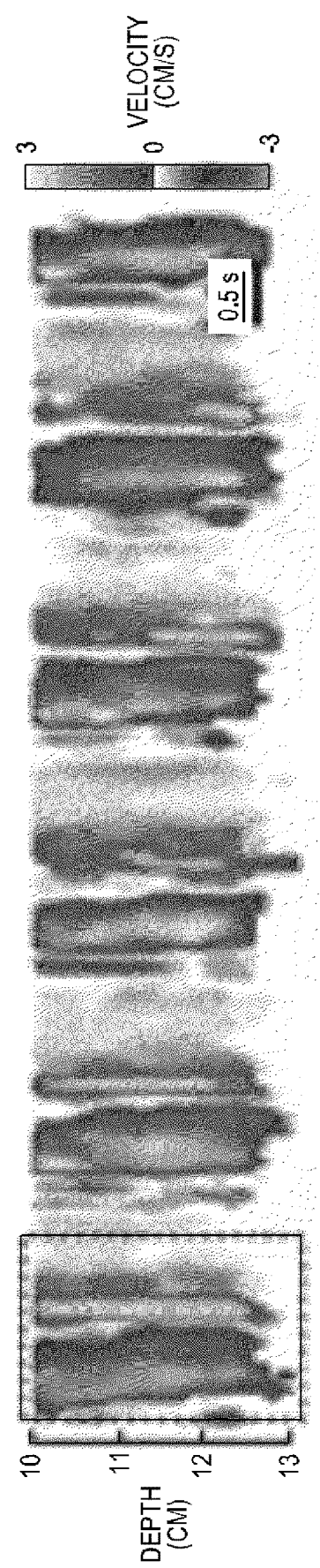
FIG. 17E shows a detailed Doppler spectrum analysis of the left ventricular (LV) posterior wall.
Figure 17F:
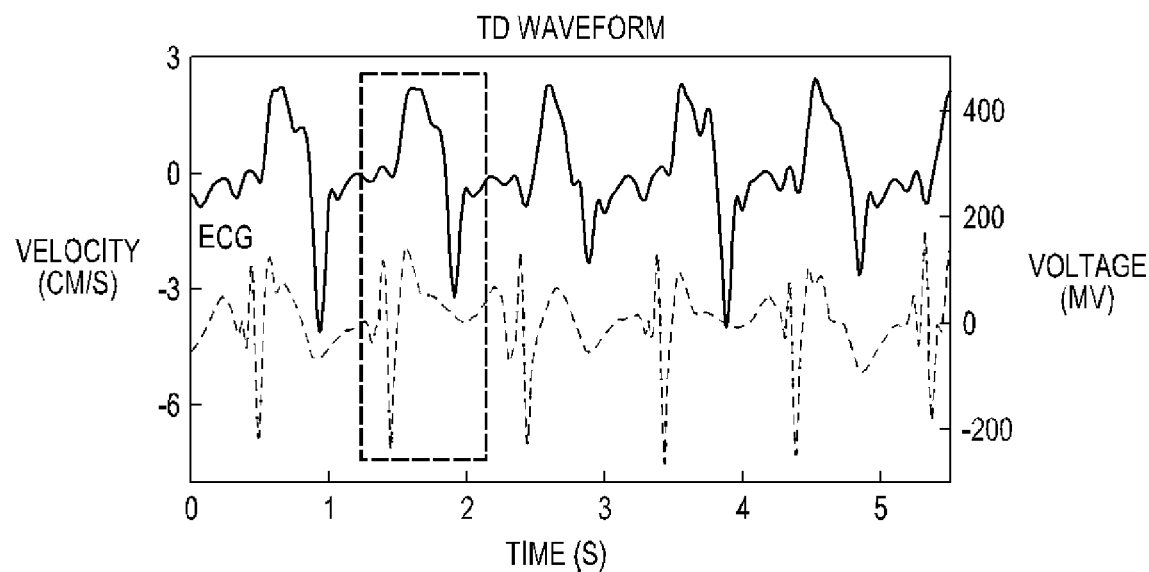
FIG. 17F shows a Tissue Doppler (TD) waveform of the LV posterior wall and an ECG waveform measured simultaneously.
Figure 17G:
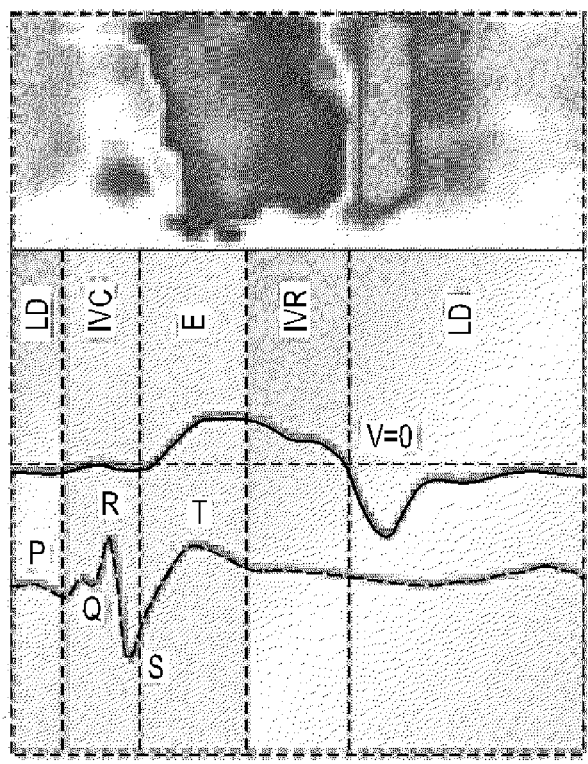
FIG. 17G shows the tissue Doppler spectrum (top), tissue Doppler waveform, and ECG recorded simultaneously.

By decoding the Doppler shift in the entire ultrasonographic window, tissue Doppler image can be reconstructed to show the real-time ventricular wall motions. The left panel in FIG. 17D is a Doppler spectrum of the ventricles, showing the simultaneous contractions of the right ventricular (RV) and the left ventricular (LV) walls in the systole phase. The right panel in FIG. 17D shows the relaxation of the two ventricular walls in the diastole phase. An analysis of the LV velocity profile appears in FIG. 17E, which shows a detailed Doppler spectrum analysis of the LV posterior wall, clearly demonstrating systolic and diastolic phases during a cardiac cycle. In FIG. 17E the periodic systolic and diastolic pattern of the LV wall is observed at a depth of about 9-12 cm. FIG. 17F shows a Tissue Doppler (TD) waveform of the LV posterior wall, showing the systolic and diastolic velocities, and an ECG waveform measured simultaneously. The correlation between the tissue Doppler waveform and the ECG waveform is evident. FIG. 17G shows the tissue Doppler spectrum (top), tissue Doppler waveform, and ECG recorded simultaneously. The two phases of systole can be clearly identified. In the iso-volumetric contraction (IVC) phase, when the atrioventricular (AV) valves close. This is then followed by the ejection (E) period, during which blood is discharged into the pulmonary artery and aorta, and the ventricular ejection reaches its highest velocity. Diastole consists of two phases. The early phase of diastole is the iso-volumetric relaxation (IVR) phase, represented by a decrease in the ventricular velocity curve. Then the aortic valve closes after the IVR phase, in which the atria and then the ventricles begin to fill. This corresponds to the late-diastole (LD) phase, which is the end of the cardiac cycle.

The cardiac phase acquired with the wearable monitoring device matches well with the cardiac cycle traced by ECG. Additionally, the tissue doppler measured by the wearable phased array ultrasonic probe provides a quantitative assessment directly from specific myocardium. That information can provide unique insight on anatomical and velocity of cardiac tissue activities, which are impossible for the ECG electrode and stethoscope to measure.

The wearable phased array ultrasonic probe described herein may also be used to monitor continuous blood flow for the long-term evaluation of tissues or organs at risk, such as the blood supply to the cerebrum and lower extremities in patients with vascular disease. Presently, there are several skin- or tissue-integrated devices that show promise for accurate long-term hemodynamic monitoring. However, these devices cannot quantitatively assess the blood flow rate, which is the key to tissue blood perfusion analysis. For instance, Doppler ultrasonography is widely considered the gold standard for blood flow measurements in central blood vessels, but similar to echocardiography, Doppler ultrasonography is generally limited to point-of-care applications for practical reasons. In contrast, as demonstrated below, the wearable phased array ultrasonic probe allows hemodynamics to be continuously monitored in most human vascular beds.

To demonstrate this ability, the blood flow in the carotid artery and the neighboring jugular vein is measured because they are the key pathways for cerebral blood perfusion and drainage. In Doppler ultrasonography, the flowing RBCs (about 8 μm in size) scatter the incident ultrasonic wave, introducing a Doppler shift in the frequency of the scattered wave, which is picked up by the device. Compared to specular reflection signals, e.g., those from cardiac muscle interfaces, signals from RBC scattering have a much lower intensity due to the relatively small size of the RBCs compared to the ultrasound wavelength. As discussed in the previous sections, phased array transmit/receive beamforming allows a high SNR that benefits RBC sensing to further enhance the reflection signal quality.

Figure 18A:
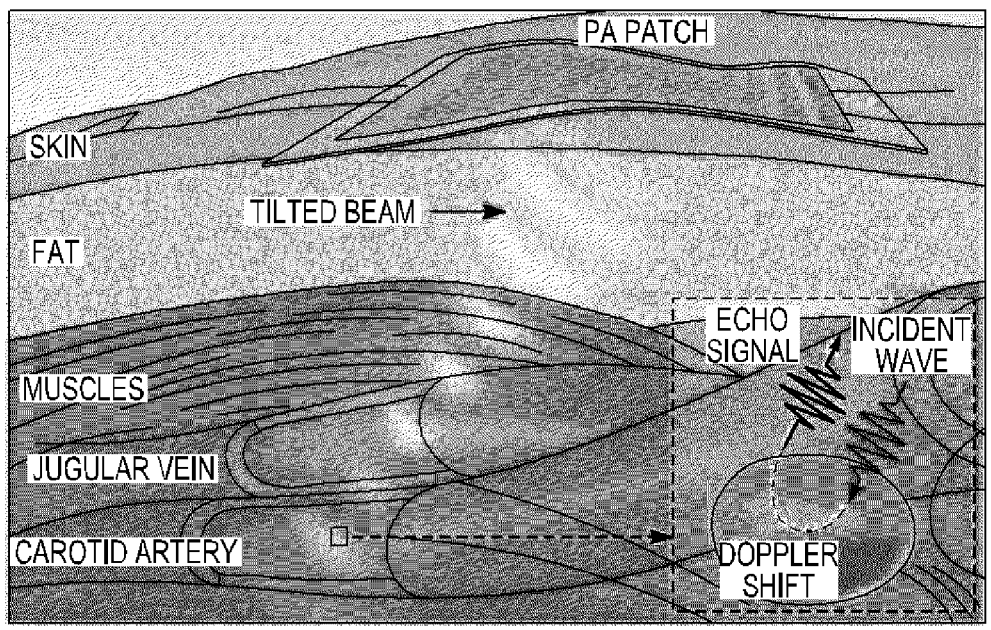
FIG. 18A schematically illustrates the working principle of ultrasonic Doppler sensing.
Figure 18B:
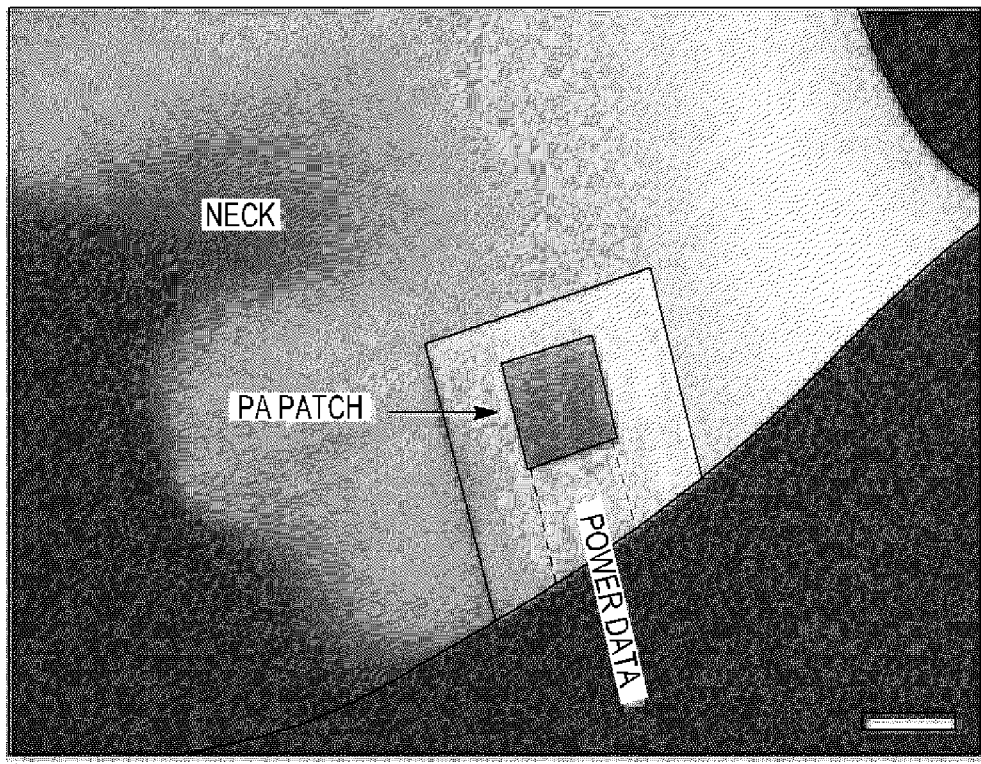
FIG. 18B shows an optical image of the wearable monitoring device when applied to the human neck.
Figure 18C:
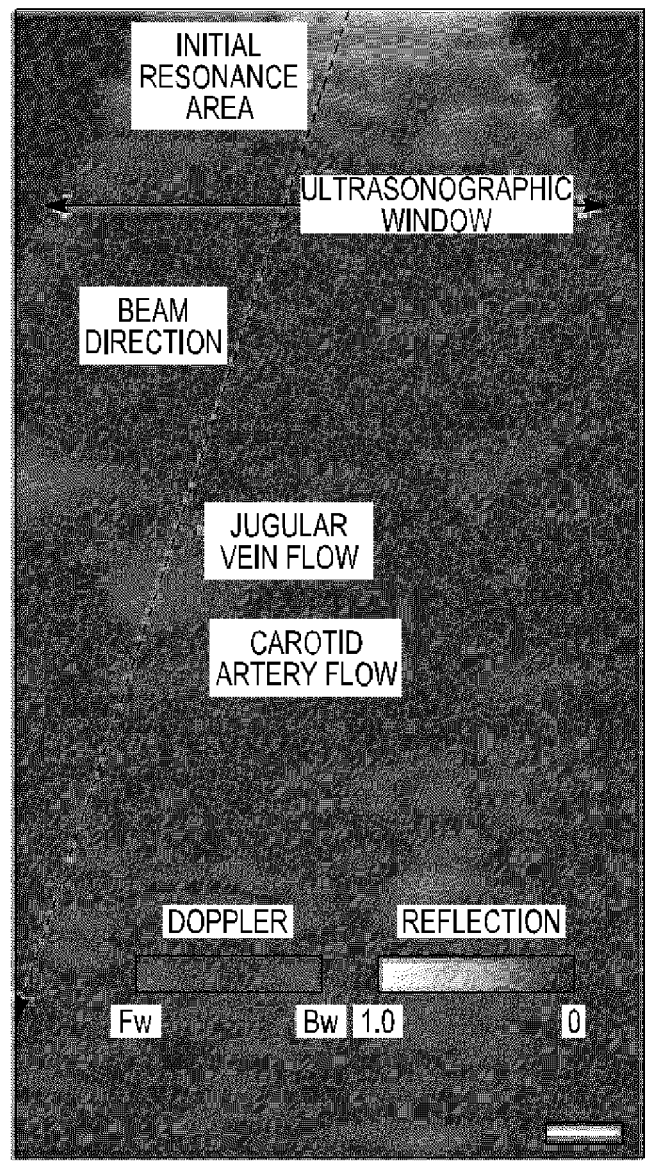
FIG. 18C shows grayscale rendition of a color flow image (CFI) depicting soft tissue structures while blood flow would be illustrated in color scale.
Figure 18D:
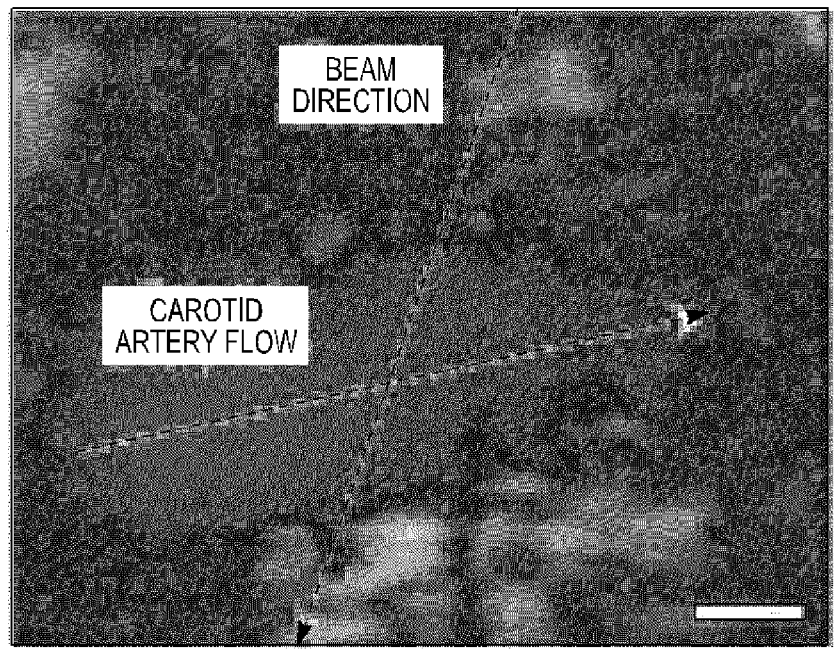
FIG. 18D shows in grayscale a CFI of the carotid arterial flow reconstructed from signals received by the wearable phased array.
Figure 18E:
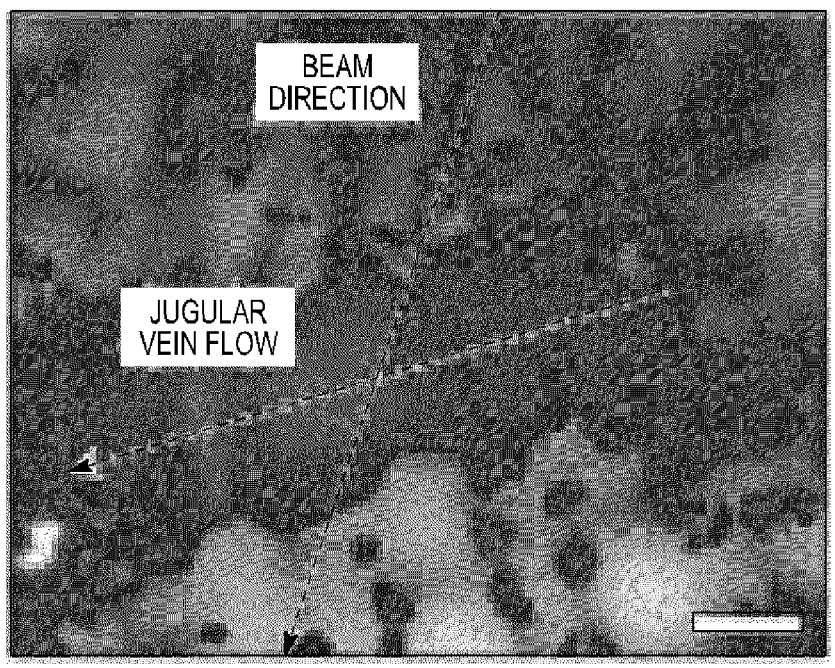
FIG. 18E shows in grayscale a CFI of the jugular venous flow reconstructed from signals received by the wearable phased array.

FIG. 18A schematically illustrates the working principle of ultrasonic Doppler sensing. The device sends a focused ultrasonic beam at ~20° incidence angle to induce Doppler interaction with moving RBCs. The inset shows the interaction between an ultrasound pulse and a moving RBC. FIG. 18B shows an optical image of the wearable monitoring device when applied to the human neck. Key components are labeled in the image. As shown in FIGS. 18A and 18B, the wearable probe is placed on the human neck surface and the ultrasonic beam is focused and steered to achieve optimal insonation of the carotid artery and jugular vein. The resulting ultrasonic energy from the 8 μm-scale RBCs is sufficient to acquire blood flow signals. By extracting the Doppler shift and vessel orientation, the blood flow velocity can be calculated. Moreover, the amplitude and Doppler frequency shift of the received signals can be used to reconstruct a color flow image, which is shown in FIG. 18C in grayscale and depicts soft tissue structures in grayscale while blood flow would be illustrated in color scale. For blood flow velocity recording, the Doppler angle, the angle between the beam and the blood vessel, should not exceed 60°. An excessive Doppler angle will induce errors. FIG. 18D shows in grayscale a CFI of the carotid arterial flow reconstructed from signals received by the wearable phased array, with the directions of the ultrasonic beam and blood flow labeled. FIG. 18E shows in grayscale a CFI of the jugular venous flow reconstructed from signals received by the wearable monitoring device, with the directions of the ultrasonic beam and blood flow labeled. The Doppler angles in FIGS. 4D and 4E are 58° and 54°, respectively.

Figure 18F:
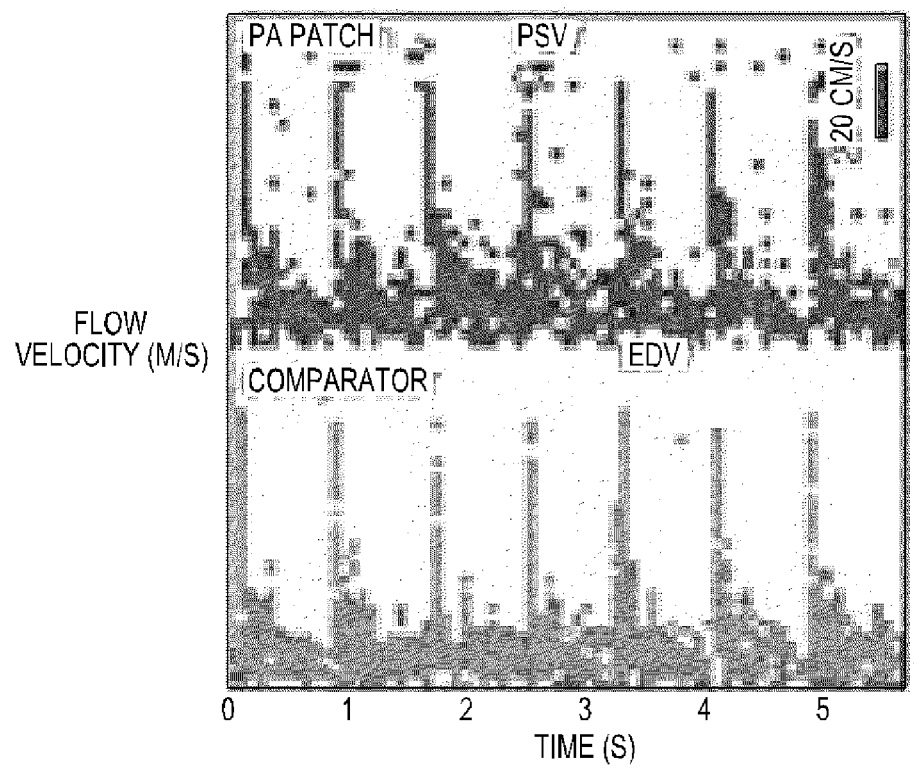
FIG. 18F shows the carotid arterial flow spectrum compared with a commercial ultrasonic probe.
Figure 18G:
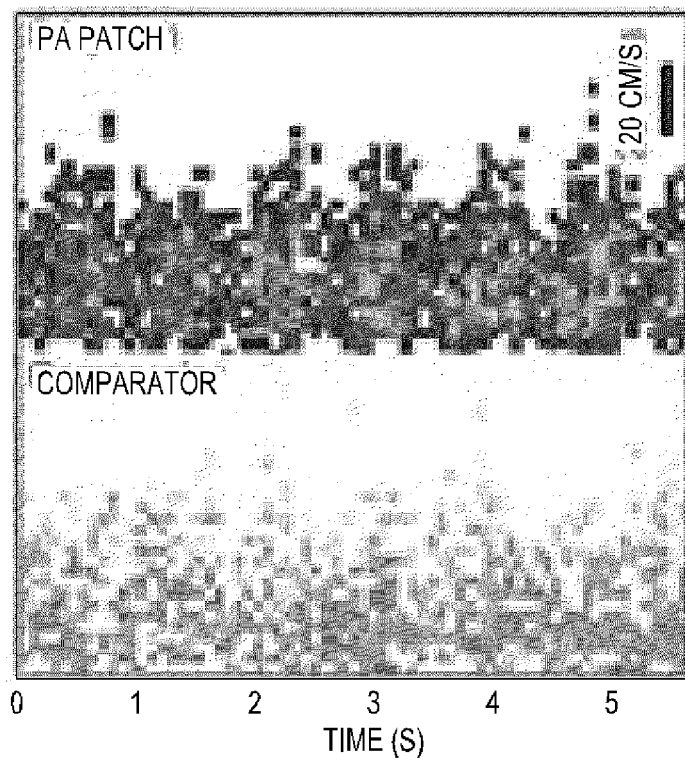
FIG. 18G shows the jugular venous flow spectrum compared with a commercial ultrasonic probe.

FIG. 18F shows the carotid arterial flow spectrum compared with a commercial ultrasonic probe and FIG. 18G shows the jugular venous flow spectrum compared with a commercial ultrasonic probe. The measured spectra of the carotid arterial flow and jugular venous flow show characteristic cardiac pulsation patterns. The peak systolic velocity (PSV) and end-diastolic velocity (EDV), two values of particular interest for hemodynamic analysis, can be directly identified on the spectra.

To validate the measurements, the wearable monitoring device and a commercial phased array ultrasonic probe (Verasonics P4-2v probe) are used for flow velocity measurement simultaneously. The results from the wearable monitoring device (top curves in FIGS. 18F and 18G) and those from the commercial probe (bottom curves in FIGS. 18F and 18G) show a high level of agreement. The measurements are repeated 30 times on three healthy subjects with both probes for PSV and EDV of the carotid arterial flow.

Figure 18H:
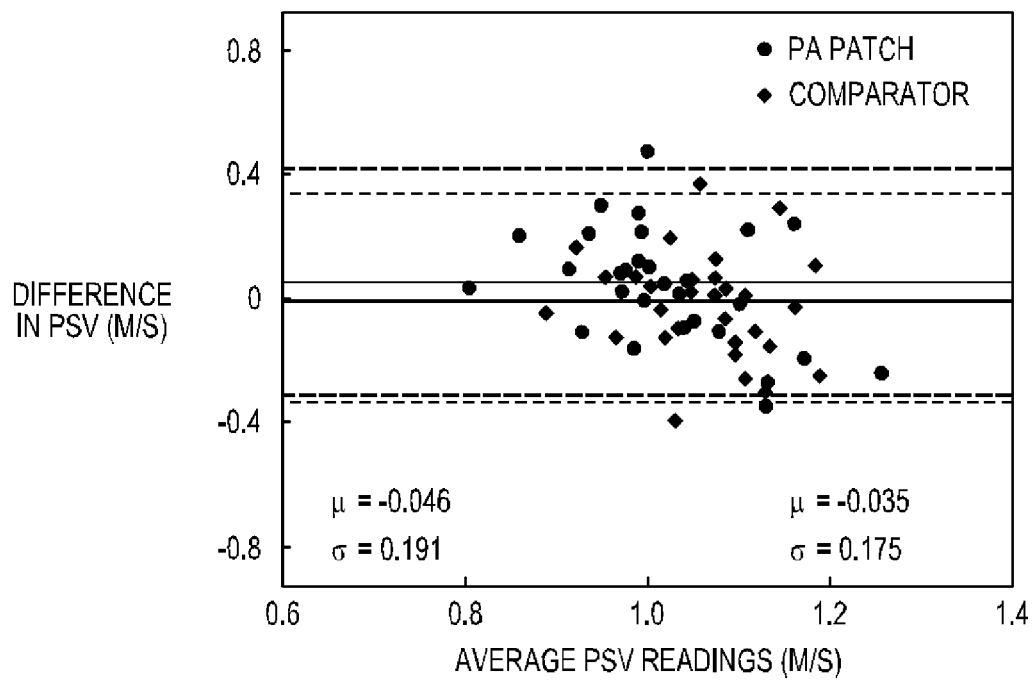
FIG. 18H is a Bland-Altman analysis of the peak systolic velocity (PSV) of carotid arterial flow.
Figure 18I:
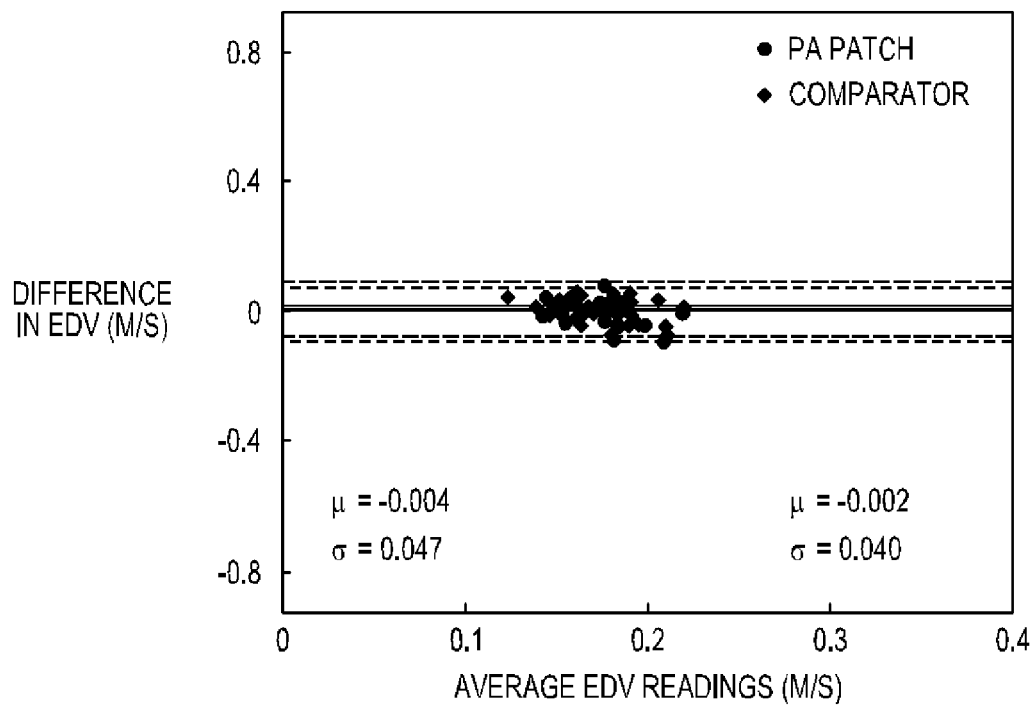
FIG. 18I is a Bland-Altman analysis of the end-diastolic velocity (EDV) of the carotid arterial flow.

FIG. 18H is a Bland-Altman analysis of the PSV of carotid arterial flow, showing an accuracy comparable to the commercial device. The wearable monitoring device yields a biased error (μ) of 0.046 m/s and a precision error (σ) of 0.191 m/s, which are comparable to the commercial device whose μ and σ are −0.035 m/s and 0.175 m/s, respectively. FIG. 18I is a Bland-Altman analysis of the EDV of the carotid arterial flow. The wearable monitoring device yields a biased error μ of 0.004 m/s and a σ of 0.047 m/s, which are comparable to the commercial device whose μ and σ are −0.002 m/s and 0.040 m/s, respectively. Thus, the Bland-Altman analysis of the data shows good agreement, demonstrating that the precision and accuracy of the wearable monitoring device is comparable to commercial probes. The wearable monitoring device is robust with minimal performance degradation after 60 days of repetitive use.

The human cerebral blood circulation is critical for sustaining the central nervous system, and it is easily affected by extreme changes in acceleration, microgravity, as well as vascular diseases such as atherosclerosis. Currently it is difficult to evaluate the cerebral circulation with non-invasive methods, and wearable monitoring devices that can record blood flow volume continuously over the long term thus satisfy a critical need. Because the carotid artery is the key pathway to the brain, the carotid blood flow (CBF) can be correlated with the volume of cerebral blood flow. CBF can be measured by a handheld ultrasonic probe. However, this method requires extensive operator training and the results can be highly operator-dependent.

Figure 18J:
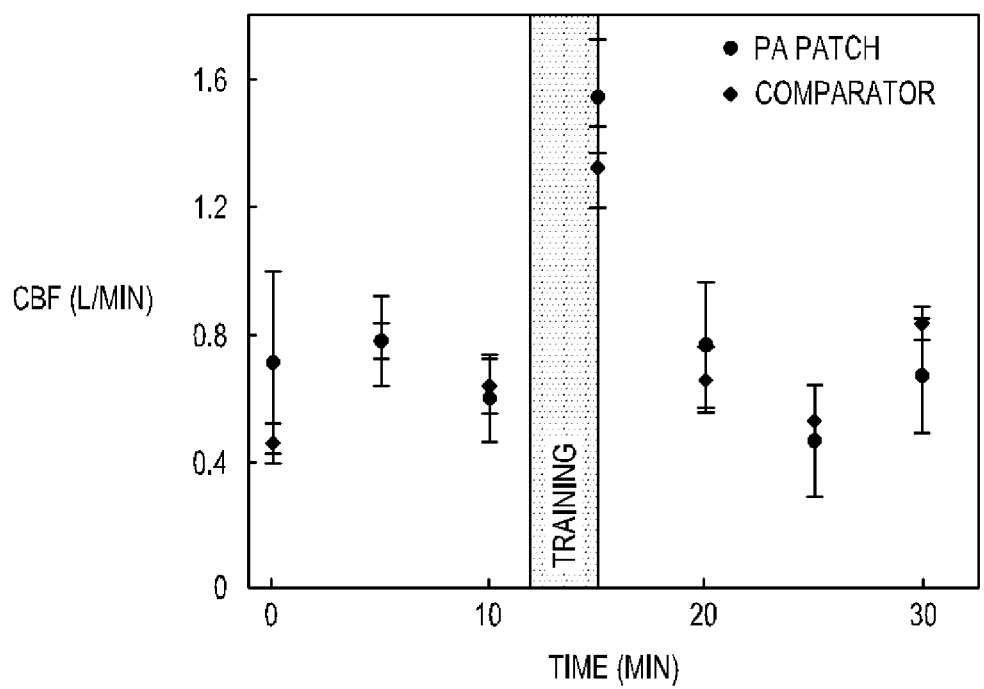
FIG. 18J shows carotid blood flow (CBF) measurements performed on a subject over a period of 30 minutes using the wearable monitoring device described herein.

With the wearable monitoring device ultrasonic probe described herein, the flow velocity inside a blood vessel and positions of the vessel walls (thus the vessel diameter) can be measured. Multiplying the average carotid flow velocity by the vessel cross-sectional area yields the CBF. CBF measurements, shown in FIG. 18J, are performed on a subject over a period of 30 minutes with 5-minute intervals, with the subject resting during the first 12 minutes, then performing the 3-minute burpee test in the $12^{th}$-$15^{th}$ minute, and resting in the last 15 minutes. It is clear from the data that, at the $15^{th}$ minute, the CBF increases from 0.590 L/min to 1.560 L/min, and after the subject rests for 5 minutes, the CBF returns to the baseline. The results show good reproducibility, as evidenced by the small error bars from three consecutive measurements on the same subject. The CBF measurements have been validated against those from a commercial phased array ultrasonic probe (Verasonics P4-2v probe).

In summary, the wearable phased array ultrasonic probe described herein opens up a new sensing dimension for wearable electronics. The sensing range of the wearable phased array is no longer limited to areas directly below the device, but expands to a much wider acoustic window. The high penetration depth in the human tissue makes possible continuous and non-invasive monitoring of central organs, and the ability to steer and focus the ultrasonic beam enables actively targeted sensing. The device maintains a high resolution for sensing microscale objects such as the RBCs, which is enabled by the high SNR as a result of phased array transmit/receive beamforming. The target organ or tissue can be expanded to other central organs, including tissues of the liver, lung, and gastrointestinal tract, for perfusion monitoring and continuous surveillance of organs-at-risk for the patients.

Additional aspects of the present invention are illustrated in FIG. 19-***, which will be described below.

Figure 19A:
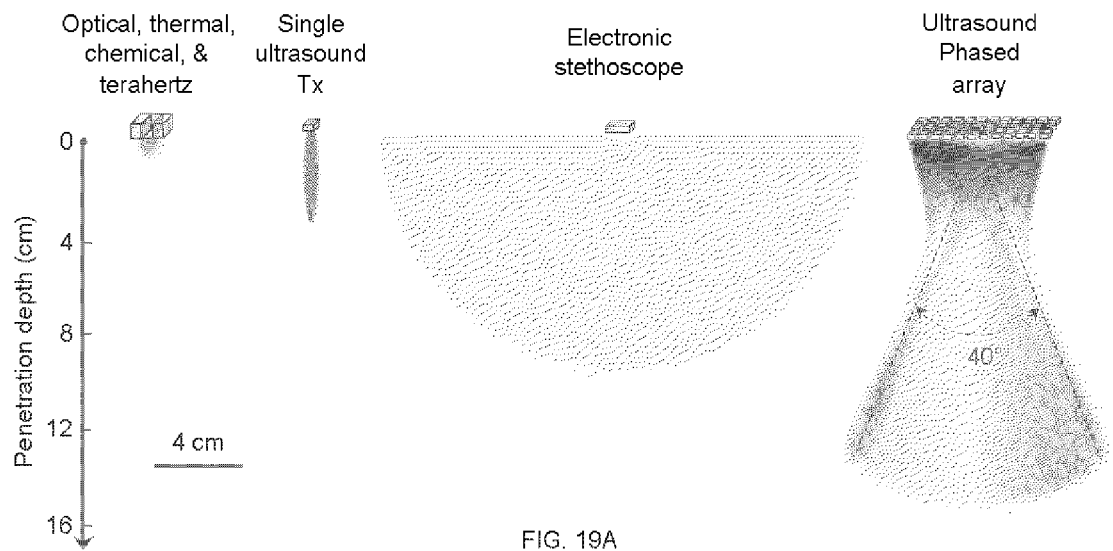
FIGS. 19A and 19B show comparisons between existing flexible/stretchable electronic devices for central organ monitoring.
Figure 19B:
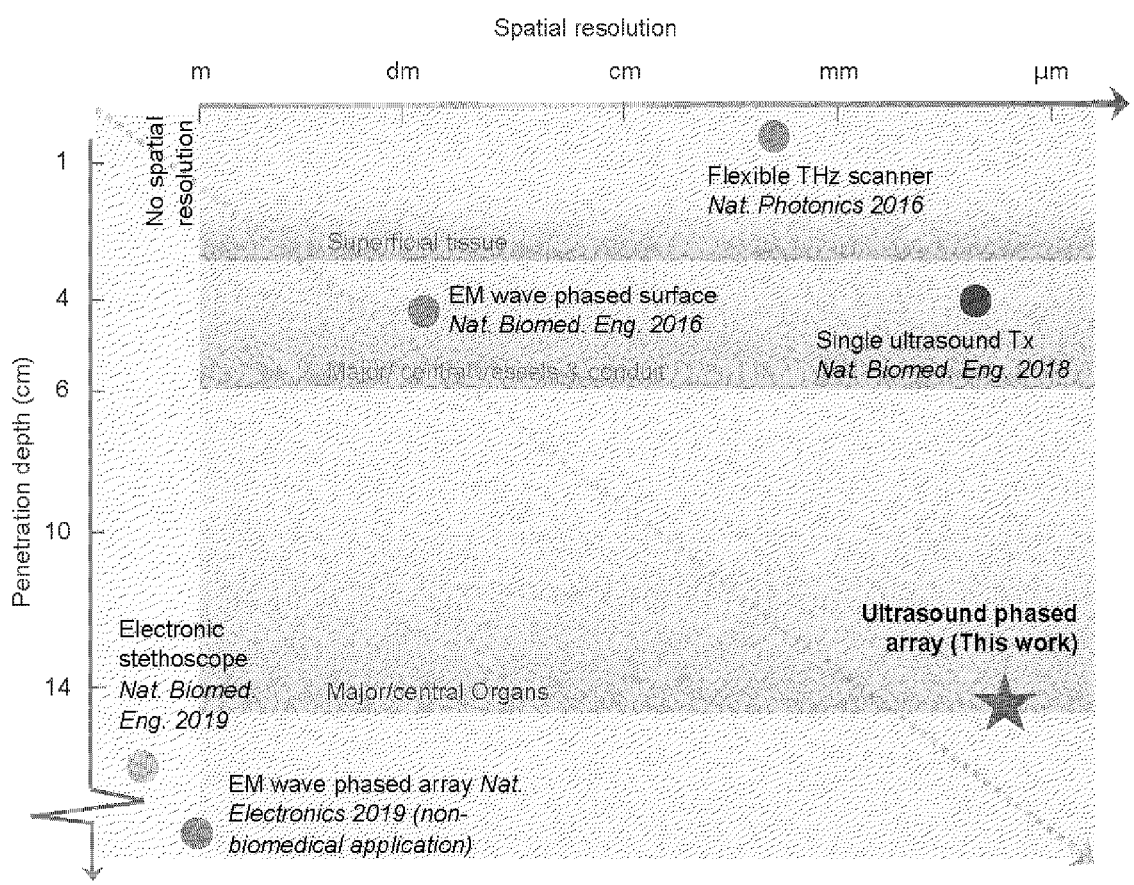

FIGS. 19A and 19B show comparisons between existing flexible/stretchable electronic devices for central organ monitoring. In particular, FIG. 19A is a comparison of the detection range (shaded areas underneath each sensing mode) of the wearable monitoring device with other flexible/stretchable biosensors, including optoelectronics, thermal electronics, iontophoresis based electrochemical sensors, terahertz wave-based sensors, single ultrasound (US) transducers, and electronic stethoscopes. The phased array has distinct advantages compared to the other sensing modalities in both penetration depth and spatial resolution. With phased array beamforming, the wearable ultrasonic probe can focus the beam to achieve longer penetration (up to 14 cm in human tissues) and steer the beam to scan over a 40° range with sufficient spatial resolution and SNR. The insonation area in 2D can reach ~68.41 $cm^2$, 380 times larger than the insonation area of a single transducer, ~0.18 $cm^2$, calculated by Field II, MATLAB, MathWorks, Natick, MA. FIG. 19B is a comparison of the penetration depth and resolution of representative flexible/stretchable biosensors in the literature. The result shows the wearable monitoring device has a long penetration depth with sufficient resolution for central organ monitoring.

Figure 20A:
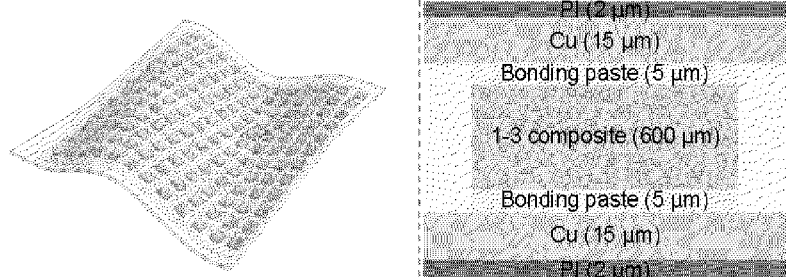
FIGS. 20A, 20B, and 20C show schematic illustrations of portions of the wearable monitoring device.
Figure 20B:
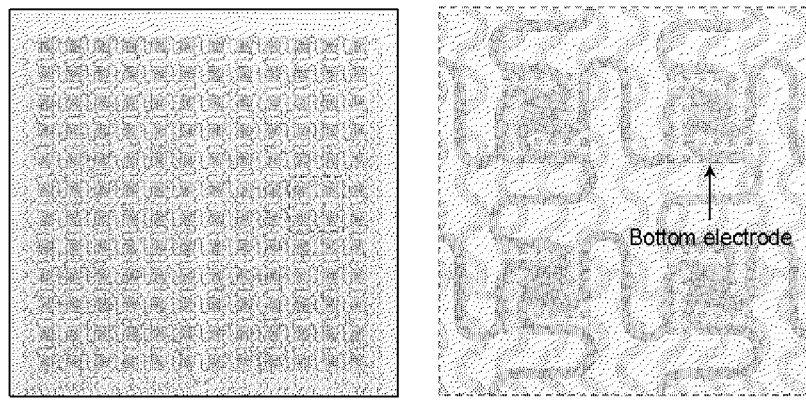
Figure 20C:
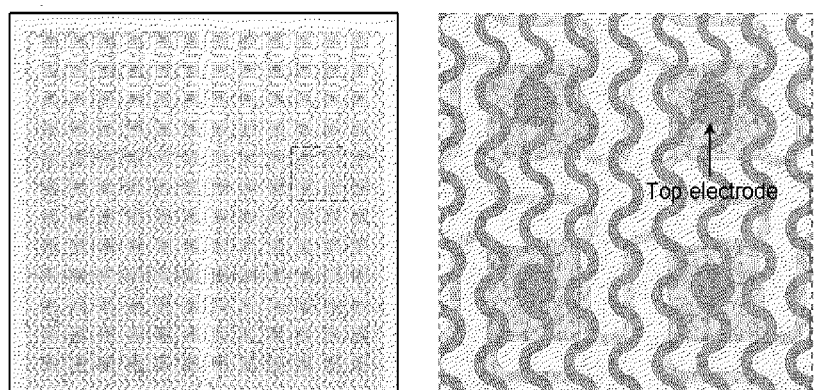

FIGS. 20A, 20B, and 20C show schematic illustrations of portions of the wearable monitoring device. In particular, FIG. 20A is a perspective view of the device. The inset shows the cross-section of a single transducer. The material layers and thicknesses are labeled. FIG. 20B is a bottom view of the device (left panel), and zoomed-in image of a 2 by 2 array highlighting the bottom electrode design (right panel). FIG. 20C is a top view of the device (left panel), and zoomed-in image of a 2 by 2 array highlighting the top electrode design (right panel).

FIGS. 21A, 21B and 21C show optical images of the wearable monitoring device. In particular, FIG. 21A is a perspective image of a wearable monitoring device on a spherical surface, showing its flexibility and stretchability. FIG. 21B is a top view of the entire device, containing the back-end connection with an anisotropic conductive film (ACF) cable, as labeled in the image. The device is covered with a medical tape to facilitate adhesion to the skin. FIG. 21C is a image of the backside of the wearable monitoring device in FIG. 21B showing the connection wires and the ACF cable.

Figure 22A:
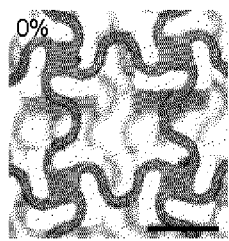
FIGS. 22A, 22B, 22C, 22D, 22E and 22F show optical images of the probe during a stretchability test of the wearable monitoring device.
Figure 22D:
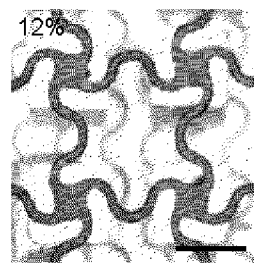
Figure 22D:
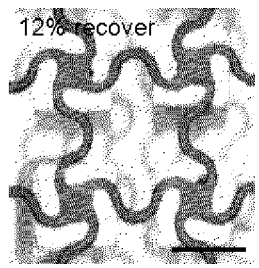
Figure 22B:
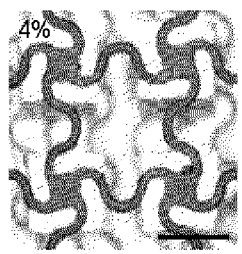
Figure 22B:
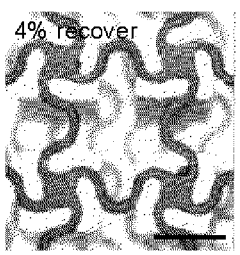
Figure 22E:
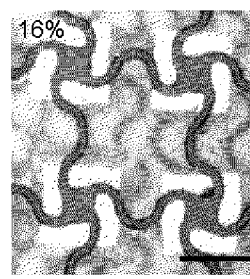
Figure 22E:
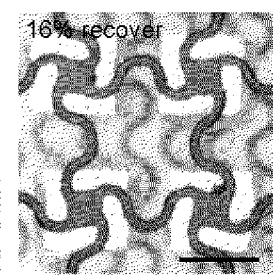
Figure 22C:
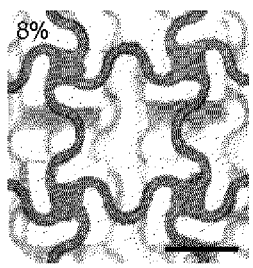
Figure 22C:
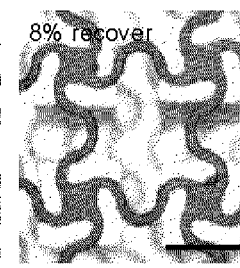
Figure 22F:
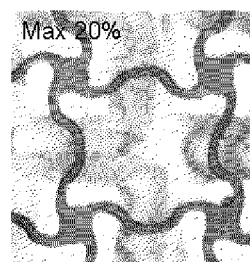
Figure 22F:
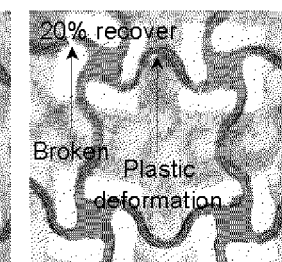

FIGS. 22A-22F show optical images of the probe during a stretchability test of the wearable monitoring device. In particular, FIG. 22A is the device in its original state with 0% strain. FIG. 22B is the device under 4% biaxial tensile strain (left) and after recovery to a strain-free state (right). FIG. 22C is the device under 8% biaxial tensile strain (left) and after recovery to a strain-free state (right). FIG. 22D is the device under 12% biaxial tensile strain (left) and after recovery to a strain-free state (right). FIG. 22E is the device under 16% biaxial tensile strain (left) and after recovery to a strain-free state (right). The results show the device can withstand biaxial strain up to 16% without plastic deformation. FIG. 22F is the device under 20% biaxial tensile strain (left) and after recovery to a strain-free state, where plastic deformation and fracture are identified (right). Scale bars are all 0.5 mm.

Figure 23A:
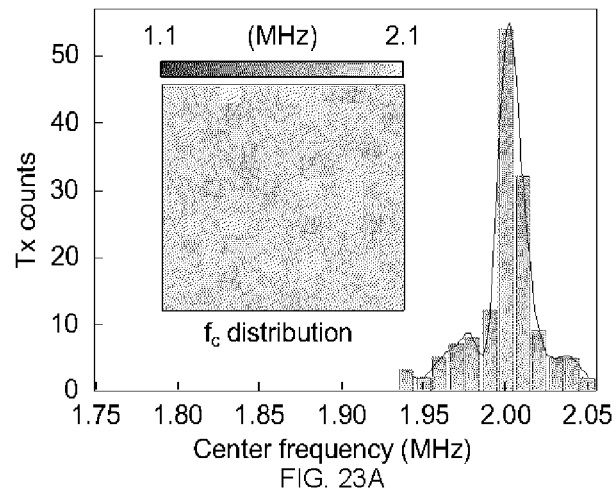
FIGS. 23A and 23B are graphs characterizing transducer element properties through the wearable monitoring device.
Figure 23B:
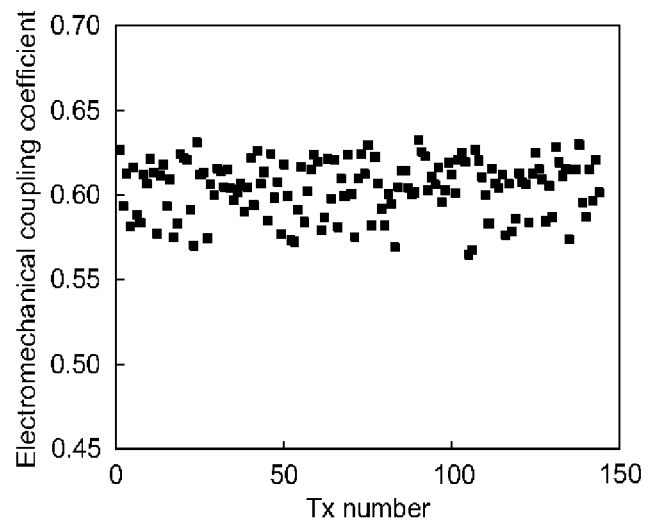

FIGS. 23A and 23B are graphs characterizing transducer element properties through the wearable monitoring device. In particular, FIG. 23A is a center frequency ($f_c$) and FIG. 23B is an electromechanical coupling coefficient ($K_t$) distribution of the 144 elements in the array, showing the consistency of transducer element properties.

FIGS. 24A-24C show field II simulations of the beam convergence and deformation tolerance of phased array beamforming at various frequencies. In particular, FIG. 24A is a comparison between the ultrasonic fields of a single (left) and two (right) transducers in the x-z plane at 1 MHz (top panels) and 8 MHz (bottom panels). Insets in the left panels show the ultrasonic beam patterns extracted along the dashed circle. The left panels show that at 1 MHz, the single transducer has a large beam-spread, and at 8 MHz, the transducer produces a beam with high directivity. The right panels show the interference patterns of the ultrasonic beam generated by two transducers, with a convergent beam at 1 MHz, and two separate beams at 8 MHz. The comparison illustrates that beams with a large spread will have better convergence. Insets in the right panels show the pulse signals of corresponding frequencies. Scale bars, 1 mm in FIG. 24B is an ultrasonic fields of a single (left) and two (right) transducers at 2 MHz, 4 MHz, and 6 MHz. Scale bars, 1 mm. Locations of the transducers in FIG. 24A and FIG. 24B are labeled with the red crosses. FIG. 24C is a phase deviation of each element in a 12 element linear array (numbered 1-12 according to their sequence in the array) upon deformation as compared to the half-wavelength at various frequencies. The black curve shows the half-wavelength at various frequencies. The pink dots show the phase deviation of the transducer array under a 4.2 cm curvature radius. Due to a large wavelength, the low-frequency transducers can tolerate more curved surface-induced distortion. Therefore, it is more suitable for the wearable monitoring device. The data in FIGS. 24A and 24B are derived by simulation. The data in FIG. 24C is derived from FIGS. 24A and B. Field II, MATLAB (MathWorks, Natick, MA).

Figure 25:
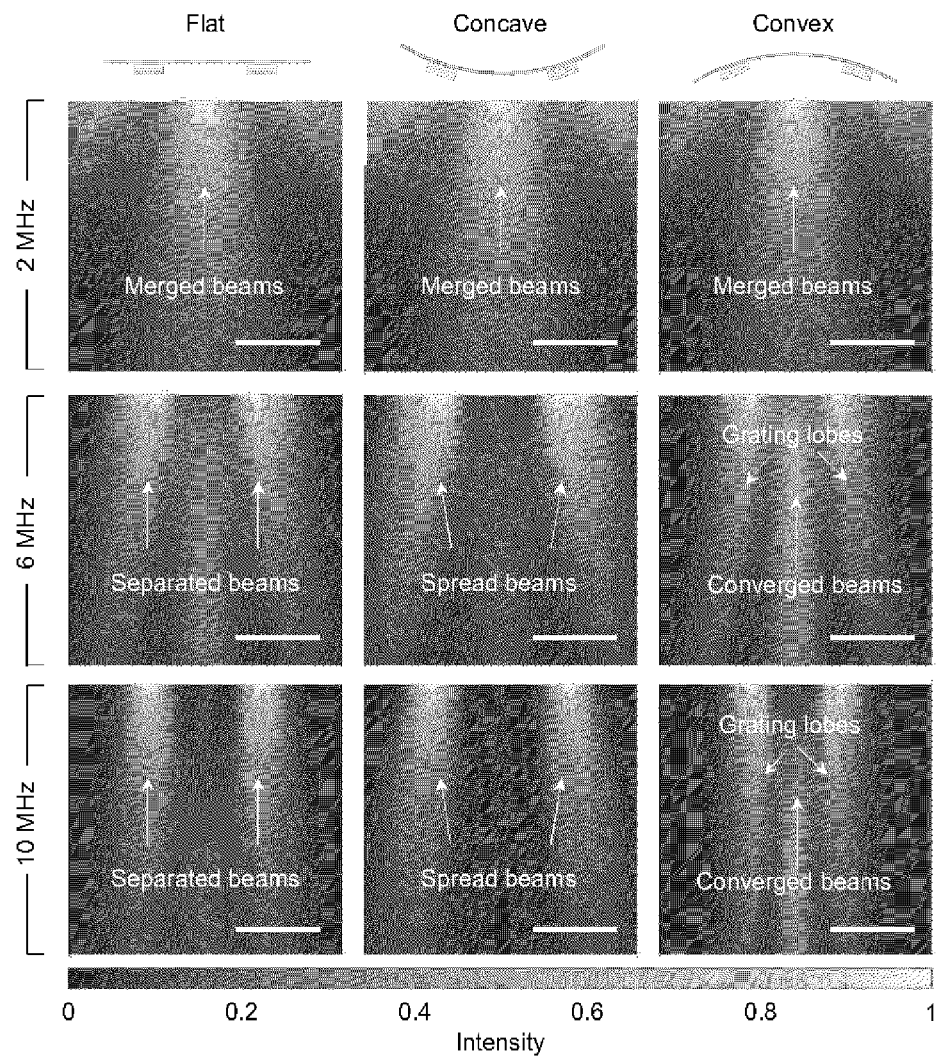
FIG. 25 shows field II simulations of the beam convergence in the x-z plane at different frequencies in various bending scenarios.

FIG. 25 shows field II simulations of the beam convergence in the x-z plane at different frequencies in various bending scenarios. The bending radius of curvature is 4.2 cm. All simulation results in the panels are for beams produced by two transducers with a 0.6*0.6 mm$^2$ footprint and a 1 mm pitch. A comparison of the results in the same bending scenario at different frequencies shows that the beams can easily merge at a low frequency, regardless of surface bending. At higher frequencies, flat and convex surfaces can easily lead to beam spreading. Although the convex surface can lead to beam convergence at higher frequencies to a certain extent, grating lobes will also appear. Therefore, phased array transducer elements with a low frequency such as 2 MHz have a high tolerance for array deformations, which is why low frequencies are preferred for building the wearable monitoring device. Scale bars are 1 mm. All the data are derived by Field II, MATLAB (MathWorks, Natick, MA).

Figure 26A:
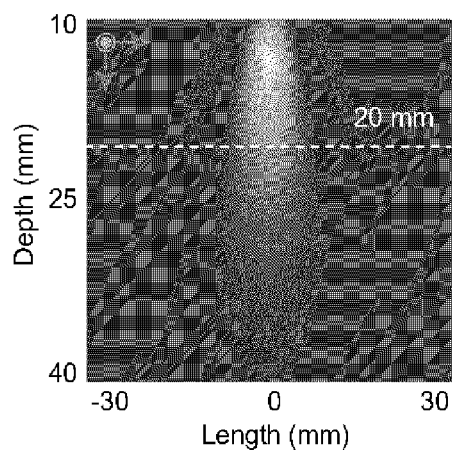
FIGS. 26A, 26B, 26C and 26D show field II simulations of the beam produced by a single transducer in the x-z plane and by phased array transducers
Figure 26B:
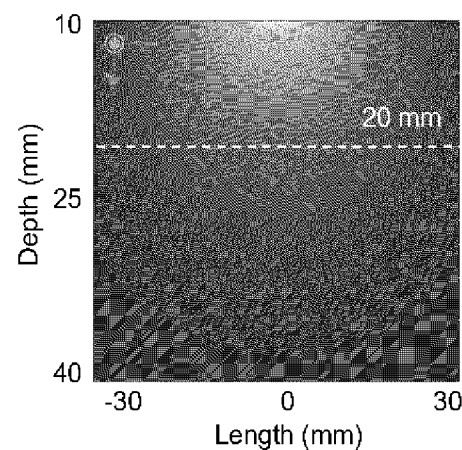
Figure 26C:
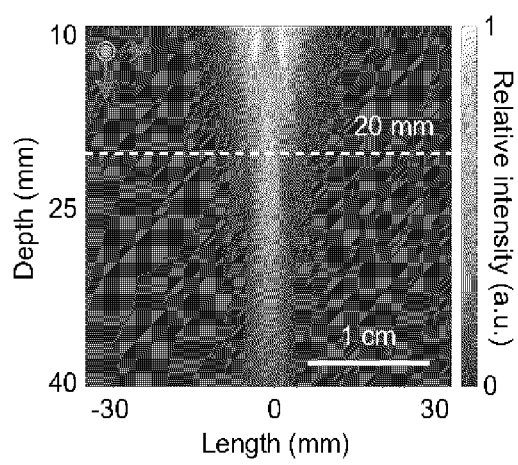
Figure 26D:
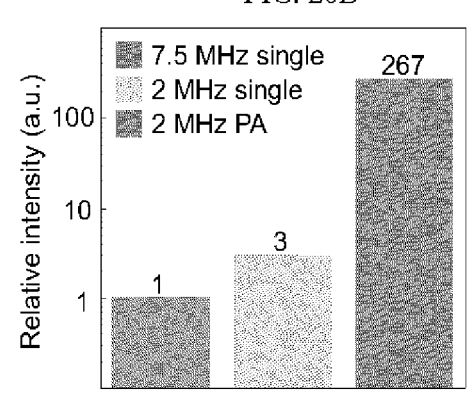

FIGS. 26A-26D show field II simulations of the beam produced by a single transducer in the x-z plane and by phased array transducers. FIG. 26A shows a simulated intensity profile of a 7.5 MHz, 0.9*0.9 mm$^2$ single transducer. FIG. 26B shows a simulated intensity profile of a 2 MHz, 0.6*0.6 mm$^2$ single transducer, and FIG. 26C shows a simulated intensity profile of a 2 MHz, 0.6*0.6 mm$^2$, 1*12 phased array. All intensity profiles are normalized individually and share the same scale bar on relative intensity. FIG. 26D is a normalized intensity comparison at 20 mm depth. All the data are derived by Field II, MATLAB (MathWorks, Natick, MA).

Figure 27A:
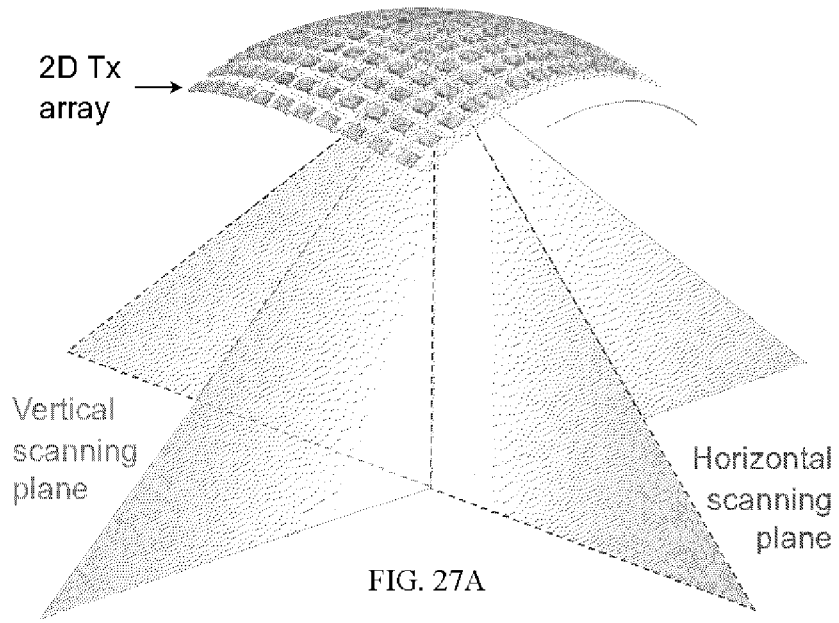
FIGS. 27A and 27B illustrate a scheme for activating the 2D phased array transducer elements.
Figure 27B:
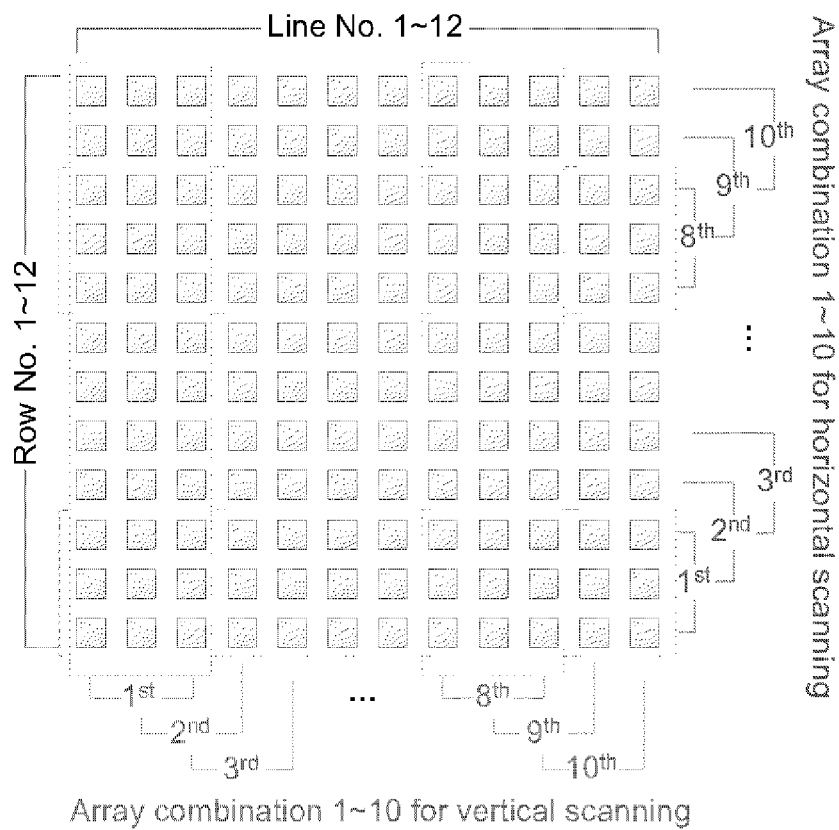

FIGS. 27A and 27B illustrate a scheme for activating the 2D phased array transducer elements. In particular, FIG. 27A shows that the overall device contains 144 individually addressable phased array elements (12 lines and 12 rows) in total. The scanning planes of the array can be in both horizontal and vertical directions by phased array beamforming. FIG. 27B shows the 12 lines/rows of transducers are composed of 10 array element combinations (in dashed boxes) for vertical/horizontal scanning. For example, the 1$^{st}$ horizontal scanning combination involves the 1$^{st}$, 2$^{nd}$ and 3$^{rd}$ rows of the array matrix. Each subsequent combination is composed of 3 adjacent rows of transducers sharing the same focal law to enhance the ultrasonic intensity and uniformity. During device operation, the 10 combinations of array elements can produce an ultrasonic beam that scans across the vertical or horizontal plane, enlarging the insonation area to cover the organs of interest.

Figure 28:
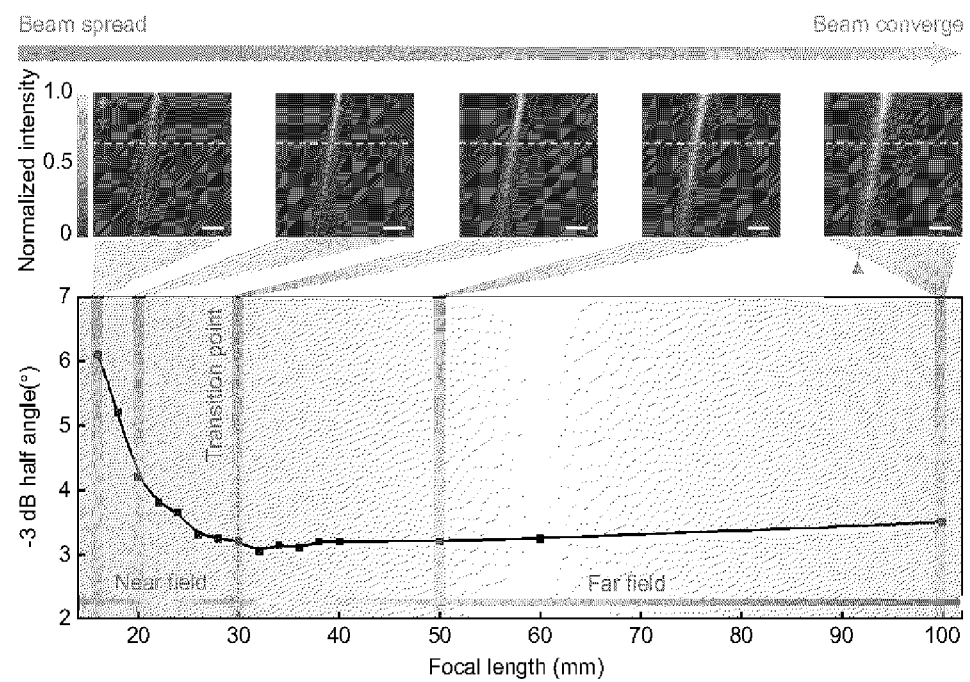
FIG. 28 shows variations of the beam directivity with the focal length.

FIG. 28 shows variations of the beam directivity with the focal length. In particular, as shown in FIG. 28 from left to right, the top 5 images are representative ultrasonic fields generated by the wearable monitoring device with a focal length of 16 mm, 20 mm, 30 mm, 50 mm, and 100 mm, respectively. The results show that longer focal lengths lead to higher beam directivity. The focal points are labeled with red triangles. Scale bars are 1 cm. The bottom chart characterizes the variation of beam directivity with the focal length from 16 mm to 100 mm. When the focal length increases from 16 mm to 30 mm, the directivity increases. Further increase in the focal length up to 100 mm does not affect the beam directivity significantly. All the acoustic fields data are mapped in the x-z plane using Acoustic Intensity Measurement System (Onda, Sunnyvale, CA).

Figure 29A:
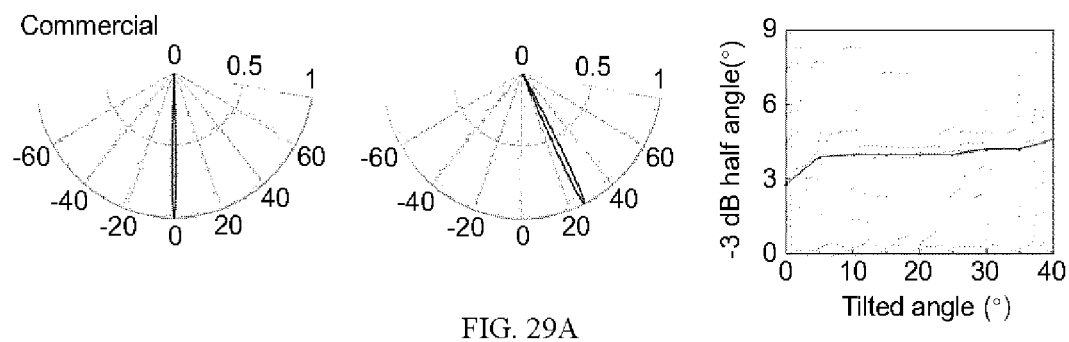
FIGS. 29A and 29B show a comparison of the beam directivity in the x-z plane between a commercial medical phased array and the wearable monitoring device.
Figure 29B:
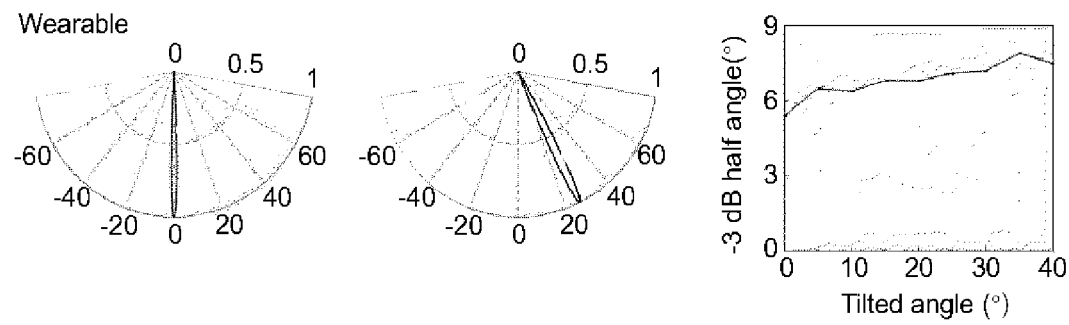

FIGS. 29A and 29B show a comparison of the beam directivity in the x-z plane between a commercial medical phased array and the wearable monitoring device. In particular, FIG. 29A shows beam patterns of a medical 2 MHz phased array (Verasonics P4-2v probe) at 0° (left panel) and 25° (middle panel), and a summary of the beam directivity at various incidence angles (from 0° to 40°) (right panel). FIG. 29B shows beam patterns of the wearable monitoring device on a curved surface (with a 4.2 cm radius of curvature) at 0° (left panel) and 25° (right panel), and summary of the beam directivity at various incidence angles (from 0° to 40°) (right panel).

FIGS. 30A-30D shows an enhancement of the orthogonal beam convergence in the x-y plane by increasing the number of rows of transducer elements in the phased array. In particular, FIG. 30A are schematic images of the phased array with 1, 3 and 5 rows, with ultrasonic beams focusing at the same point. The insets are illustrations of the beam cross-sections in the x-y focal plane, corresponding to mapping locations in FIG. 30B. FIG. 30B is normalized ultrasonic mapping results of beam intensity distributions in the x-y focal plane corresponding to the scenarios in FIG. 30A, showing better beam convergence by increasing the number of rows of the phased array. Scale bars are 3 mm. FIG. 30C is a comparison of the ultrasonic mappings of the three scenarios (from left to right: 1, 3, 5 rows, respectively), on the same intensity scale. Besides the enhancement in directivity, the beam intensity also increases with the number of rows. Scale bars are 2 mm. FIG. 30D is the beam width (red) and intensity (black) of the phased array with 1, 3, and 5 rows. More rows of the phased array lead to both higher beam directivity and intensity. All the acoustic fields data in FIGS. 30B and 30C are mapped in Acoustic Intensity Measurement System (Onda, Sunnyvale, CA).

Figure 31A:
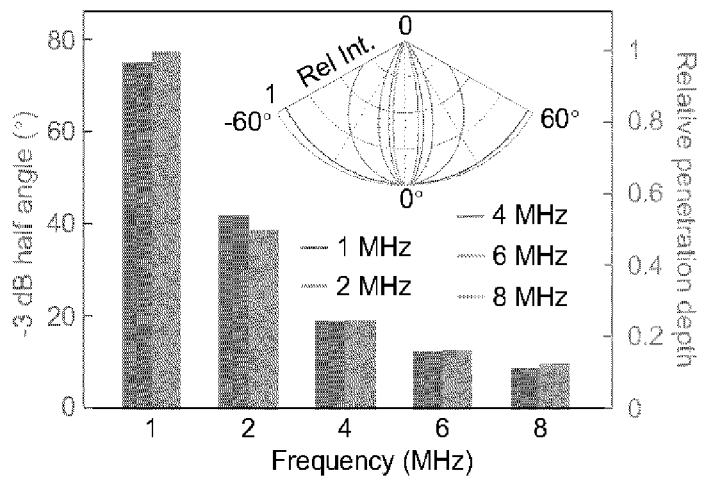
FIGS. 31A, 31B and 31C illustrate the process of tuning the ultrasonic performance of a single transducer in terms of the center frequency and the number of excitation pulses.
Figure 31B:
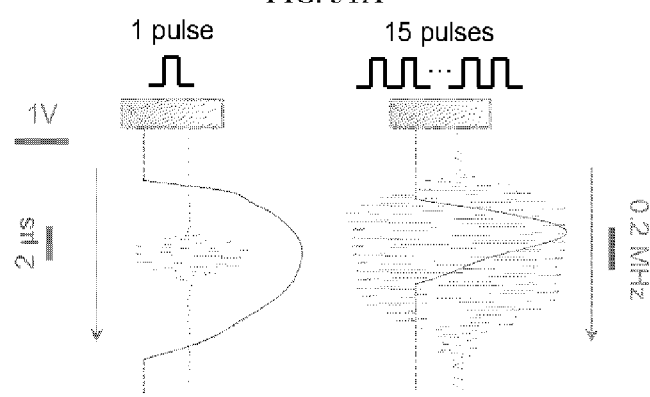
Figure 31C:
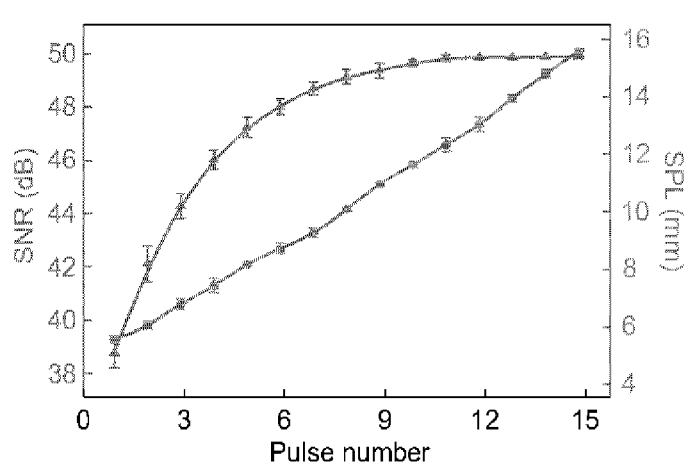

FIGS. 31A-31C illustrates the process of tuning the ultrasonic performance of a single transducer in terms of the center frequency and the number of excitation pulses. The tunable properties of single transducer include beam directivity, penetration, bandwidth of the receiving signal, SNR, and spatial pulse length (SPL). FIG. 31A is a simulated −3 dB half-angle and penetration depth of the beam produced by a single transducer at frequencies from 1 to 8 MHz. The beam has high directivities at high frequencies, and vice versa; the beam has long penetration depths at low frequencies, and vice versa. Inset is the simulated beam pattern at different frequencies, with the largest beam spreading at low frequencies. The data are derived from Field II, MATLAB (MathWorks, Natick, MA). FIG. 31B is a radiofrequency and corresponding fast Fourier transform (FFT) signals of a single pulse (left) and multi-pulse (right) excitation. The longer pulse duration and smaller bandwidth of the multi-pulse excitation. enhance the sensitivity of the phased array probe to Doppler frequency shifts. FIG. 31C is an experimental characterization of the SNR and SPL of a single transducer with different numbers of excitation pulses, showing enhancement in both the SNR and SPL with multi-pulse excitation. The signal is reflected from an aluminum block that is 2 cm away from the transducer.

Figure 32A:
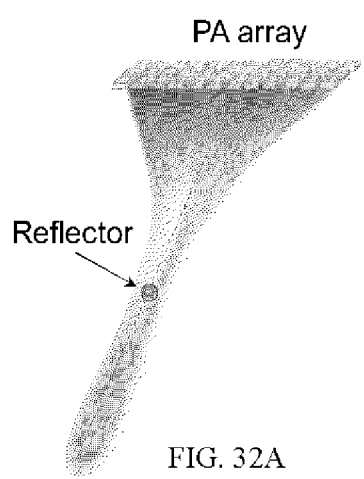
FIGS. 32A, 32B and 32C illustrate that the SNR of the phased array can be enhanced using multi-pulse excitation.
Figure 32B:
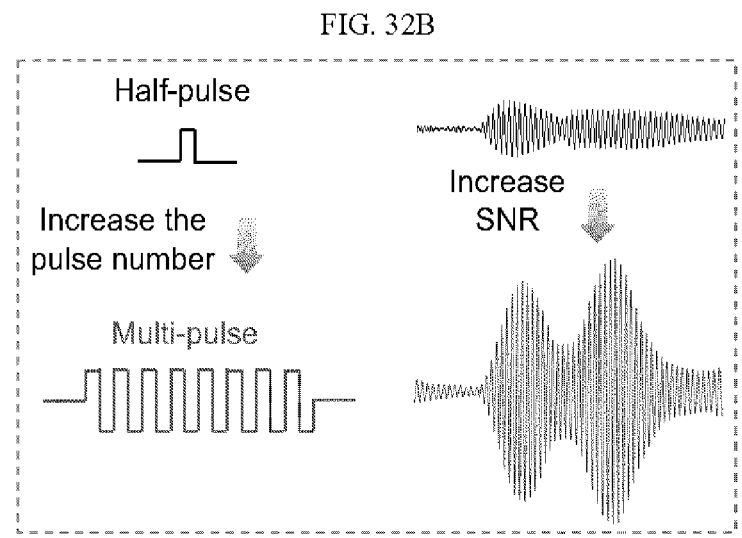
Figure 32C:
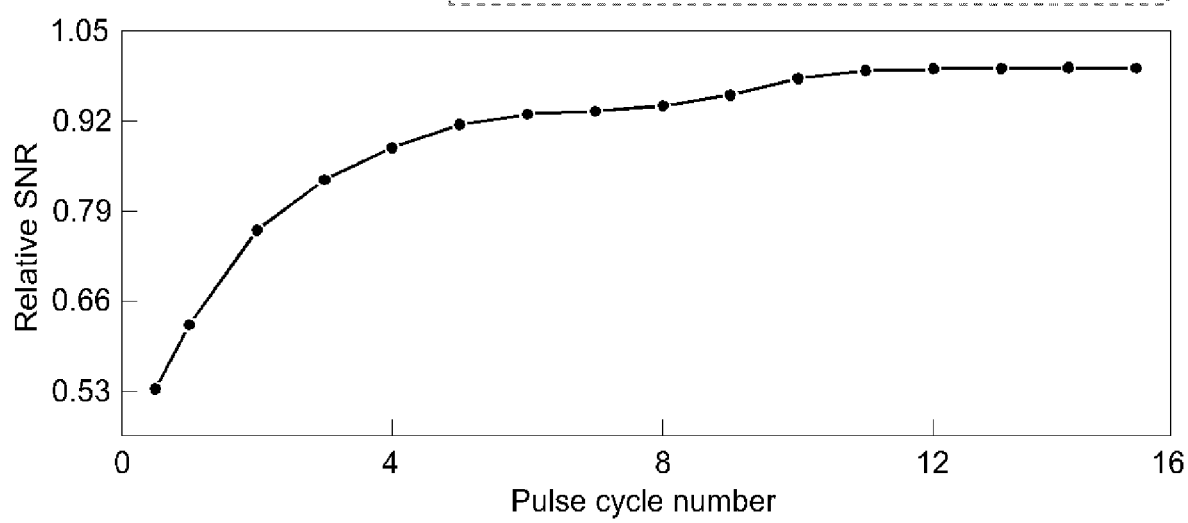

FIGS. 32A-32C illustrate that the SNR of the phased array can be enhanced using multi-pulse excitation. In particular, FIG. 32A is a schematic image of the phased array with a 1 mm in diameter reflector placed in the path of the focused beam, simulating a sensing scenario in clinical applications. FIG. 32B is a schematic illustration of the half-pulse and multi-pulse excitation signals. The corresponding received signals are on the right, showing the enhanced SNR with multi-pulse excitation. FIG. 32C shows the SNR (under 10 cm depth in the tissue) as a function of the number of excitation pulses, showing that the SNR increases with the number of pulses for exciting the phased array elements.

Figure 33A:
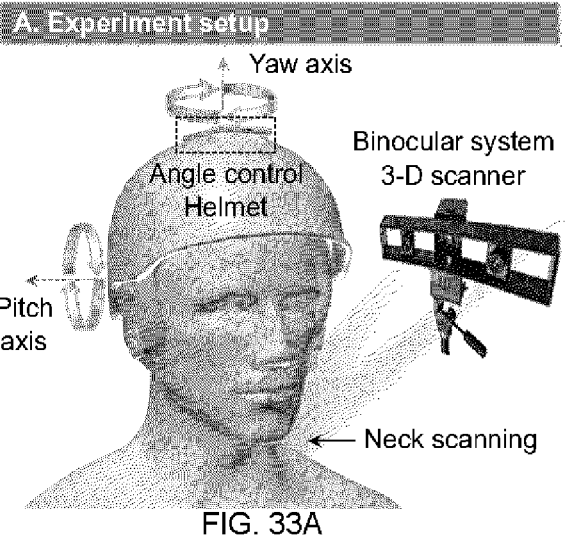
Figure 33B:
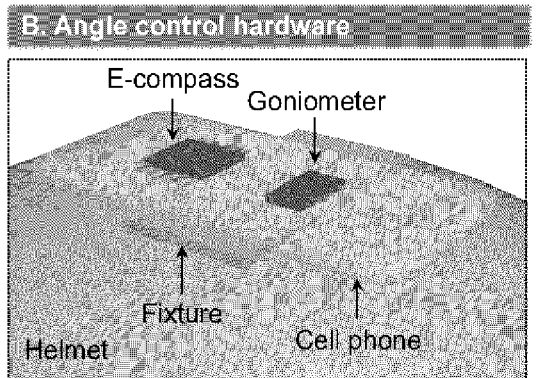
Figure 33C:
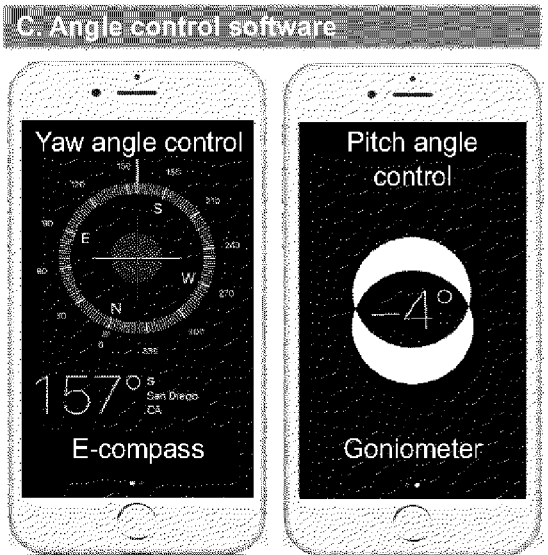
Figure 33C:
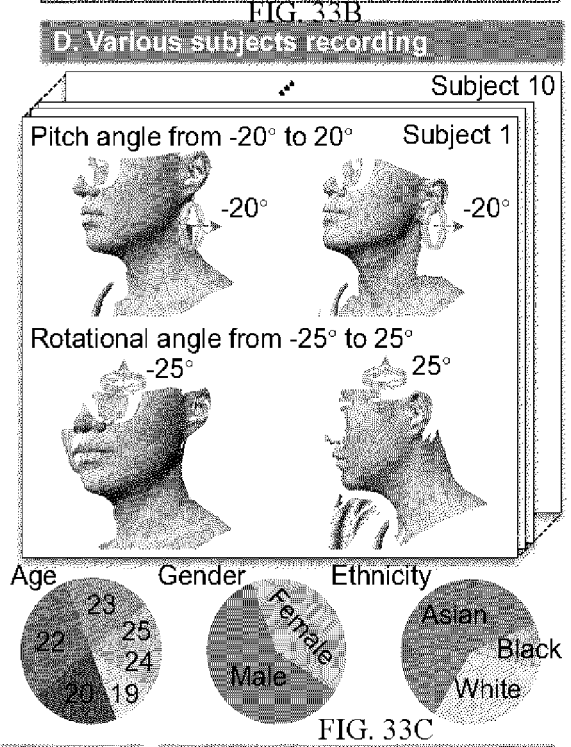
Figure 33E:
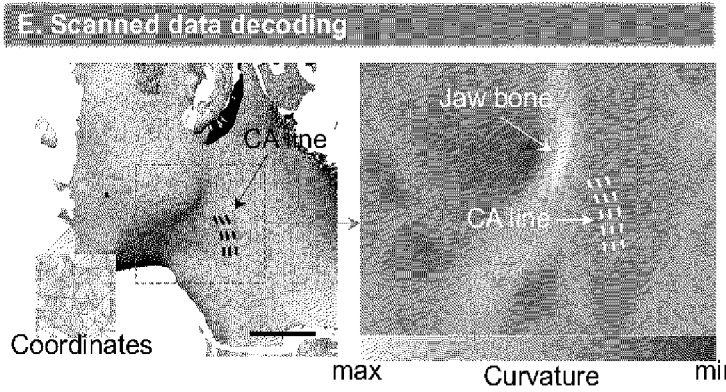
Figure 33F:
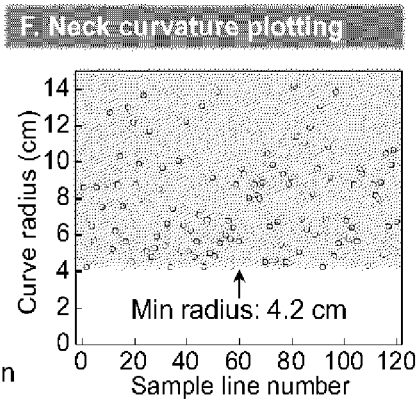

FIGS. 33A-33F characterize the skin curvature on the human neck in typical postures. In particular, FIG. 33A is a schematic setup for scanning the skin curvature. The posture is characterized by a helmet equipped with kinematic sensors. The posture is characterized by two axes of rotation, i.e., pitch and yaw. The skin surface in each posture is scanned by a 3D scanner (HDI Advances, LMI Technologies, Vancouver, Canada) to determine its maximum curvature. FIG. 33B shows detailed information about the hardware for posture characterization. A cell phone with a built-in E-compass and a goniometer are fixed on the helmet for sensing and characterization of the neck posture. FIG. 33C is a pitch and yaw angle reading software interface in the cell phone. FIG. 33D shows the designated postures for the skin posture measurements (top) and the demographic information of the 10 test subjects (bottom). The measured pitch angle ranges from −20° to 20°; the measured yaw angle ranges from −25° to 25°. FIG. 33E is the detailed process for analyzing the scanned data. The left panel shows the raw digital model recreated by the 3D scanning, with the position of the carotid artery (CA) marked. The zoomed-in image at the lower-left corner shows an example of the skin profile information extracted from the raw model on a small area of the skin, which is used for local skin curvature calculations. The right panel shows the calculated curvature distribution in the region near the CA. FIG. 33F shows skin curvature distribution near the CA, showing the minimum radius of curvature of all subjects is about 4.2 cm, which indicates the required deformation tolerance of the wearable monitoring device.

FIGS. 34A-34E show detailed skin curvature calculation protocols.

FIGS. 34A-34E show detailed skin curvature calculation protocols. In particular, FIG. 34A shows a raw digital model from the skin curvature scanning. The 3D mesh digital model is created by a 3D scanner (HDI Advances, LMI Technologies, Vancouver, Canada). FIG. 34B shows five datum planes parallel to the CA line, with a pitch of 1 cm, are drawn to intersect the 3D model, generating five intersection curves. FIG. 34C shows five datum planes are drawn to intersect at the normal to the surface of the 3D model at a selected point near the CA, with an angle increment of 10°, generating five intersection curves. The goal is to ensure adjacent planes in the rotating direction can be processed near the actual CA line. FIG. 34D shows a zoomed-in image of the intersection curves near the CA (area in the dashed lines in FIG. 34B). FIG. 34E is a zoomed-in image of the intersection curves near the CA (area in the dashed box in FIG. 34C)). The intersection curves are used to identify the maximum curvature of the human neck skin in a specific body posture. The cross on each curve marks the point of maximum curvature along that curve. We pick the maximum curvature of all intersection curves in the typical human postures to represent the maximum curvature near the CA.

Figure 35A:
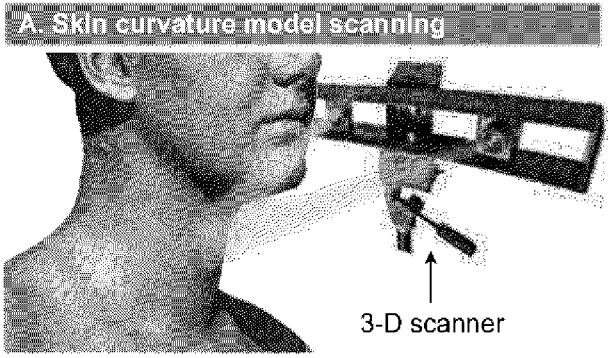
FIGS. 35A, 35B, 35C, 35D, 35E, 35F and 35G illustrate the performance of the wearable monitoring device in the x-z plane at the CA depth on a phantom replicated from the human neck.
Figure 35B:
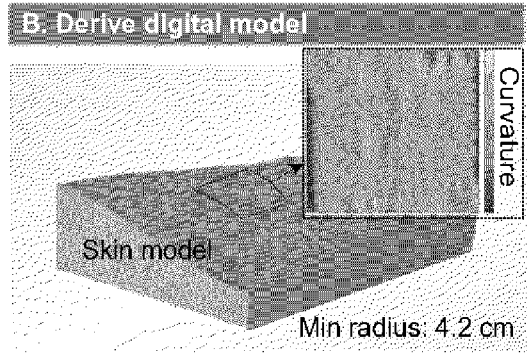
Figure 35C:
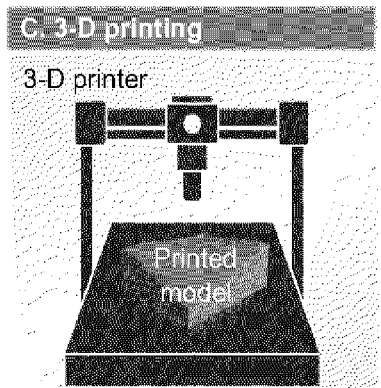
Figure 35D:
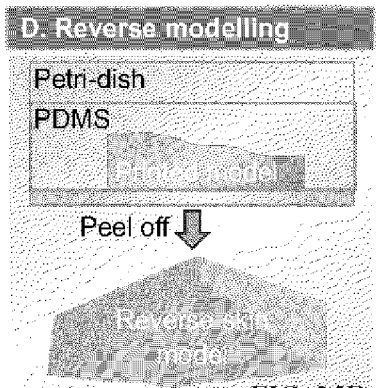
Figure 35E:
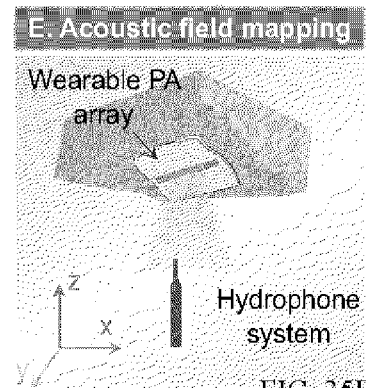
Figure 35F:
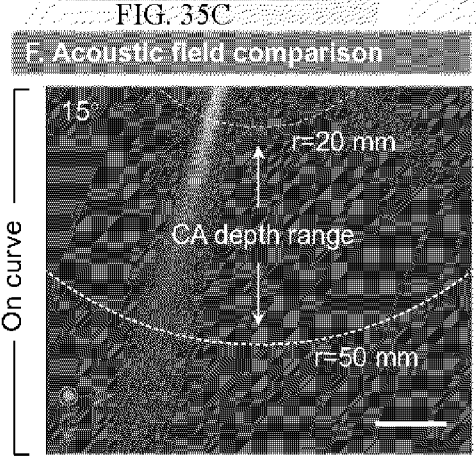
Figure 35G:
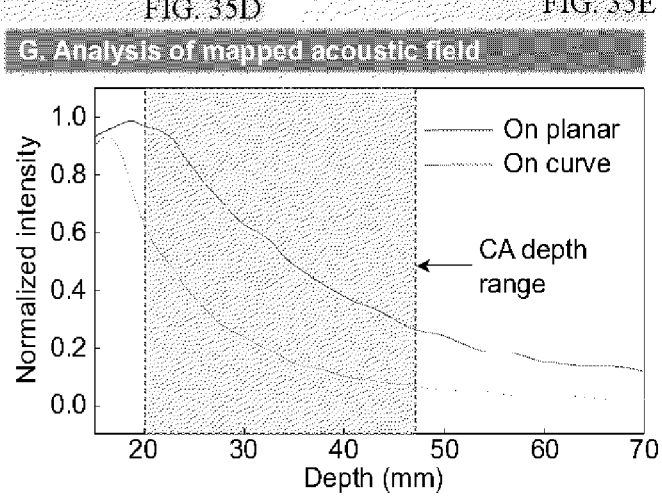

FIGS. 35A-35G illustrate the performance of the wearable monitoring device in the x-z plane at the CA depth on a phantom replicated from the human neck. A 3D digital model from 3D scans were first created from the human neck. A polydimethylsiloxane (PDMS) phantom was then cast from a 3D printed mold and used for subsequent probe testing. FIG. 35A is a schematic setup for scanning the skin curvature on the human neck. FIG. 35B is a 3D digital model created from the scan. FIG. 35C is a schematic setup for the phantom creation with 3D printing. FIG. 35D is a cast setup using the 3D printed model as the mold to cure the PDMS phantom. FIG. 35E is a mapped ultrasonic field of the wearable monitoring device on the PDMS reverse mold. The depth range of the CA is marked by the dashed lines. FIG. 35F is a mapped ultrasonic field of the wearable monitoring device on a curvilinear surface (top panel) and a flat surface (bottom panel). The depth range of the CA is marked by the dashed lines. The mapping intensity results share the same scale bar. FIG. 35G is a beam intensity (top panel) and directivity (bottom panel) analysis of the wearable monitoring device at different depths. The performance of the wearable monitoring device is comparable on the two surfaces. The shaded area in the top panel represents the depth range of the CA.

Figure 36A:
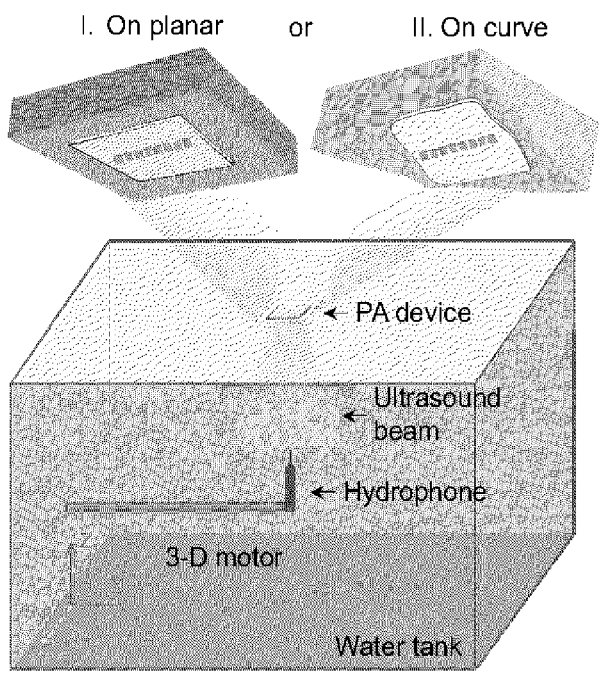
FIGS. 36A, 36B, 36C, and 36D illustrate the performance of the wearable monitoring device at different incidence angles in the x-z plane on the phantom replicated from the human neck.
Figure 36C:
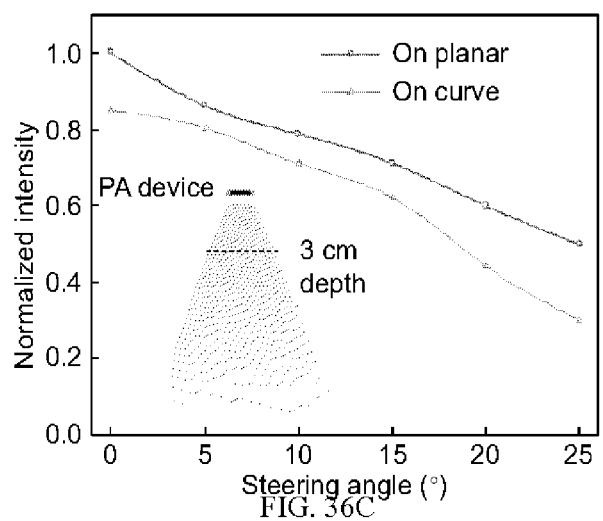
Figure 36D:
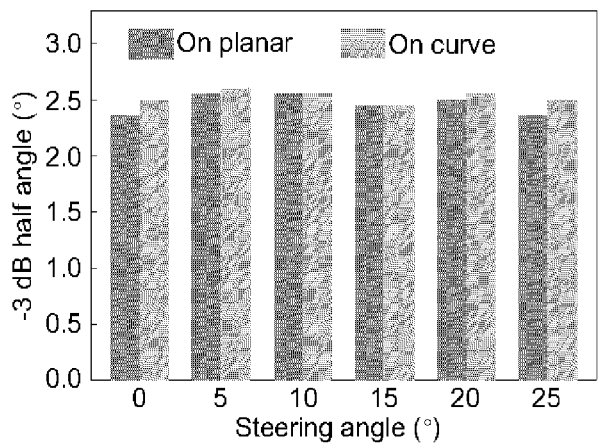
Figure 36B:
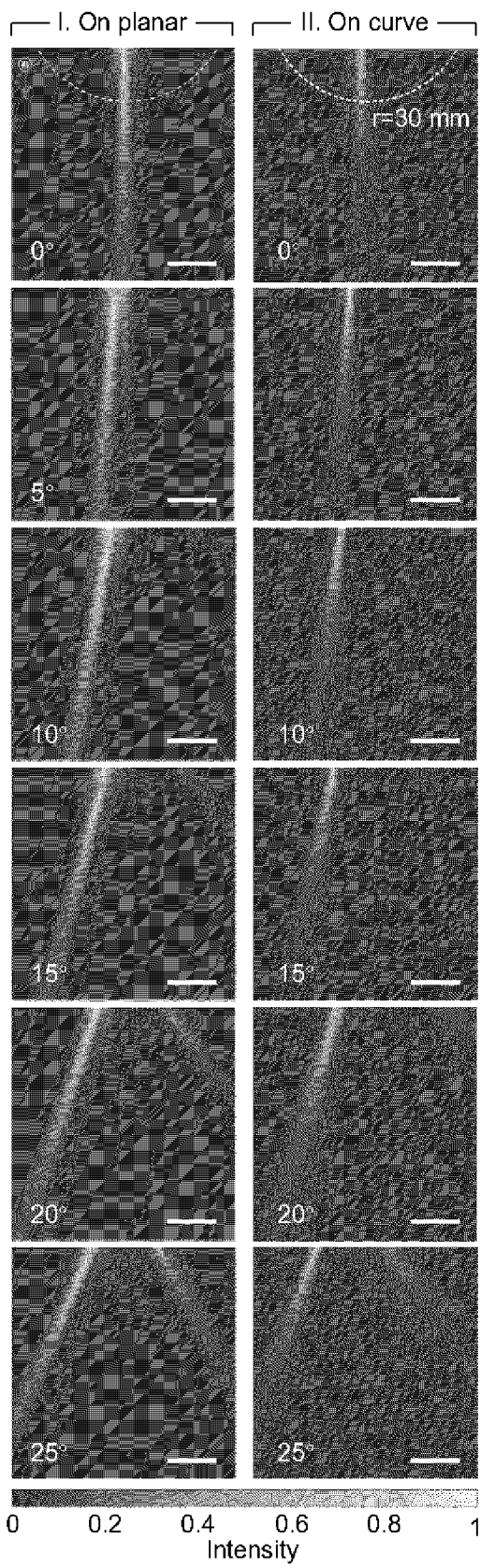

FIGS. 36A-36D illustrate the performance of the wearable monitoring device at different incidence angles in the x-z plane on the phantom replicated from the human neck. In particular, FIG. 36A shows a schematic setup of the characterization. Ultrasonic field mapping is carried out with the wearable monitoring device on a flat (top left) or a curvilinear (top right) surface. The characterization system is composed of a water tank and a 3D motor system with a hydrophone on its tip. FIG. 36B is a mapped ultrasonic field with the wearable monitoring device on a flat (left) and a curvilinear (right) surface with an incidence angle range of 0°-25°. Scale bars are 2 cm. FIG. 36C is a normalized beam intensity of the wearable monitoring device at a typical CA depth (~3 cm) with different incidence angles. The inset illustrates the depth at which the intensity measurements are taken. FIG. 36D is a beam directivity of the wearable monitoring device at a typical CA depth (~3 cm) with different incidence angles. The beam directivity of the wearable monitoring device is comparable on the two surfaces with all incidence angles in the range tested.

Figure 37A:
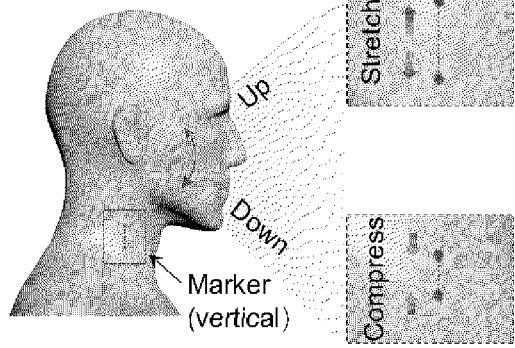
FIGS. 37A, 37B, 37C, 37D, 37E, 37F and 37G illustrate the performance of the wearable monitoring device under tensile/compressive strain.
Figure 37B:
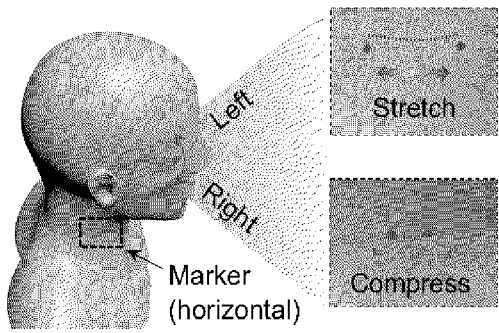
Figure 37E:
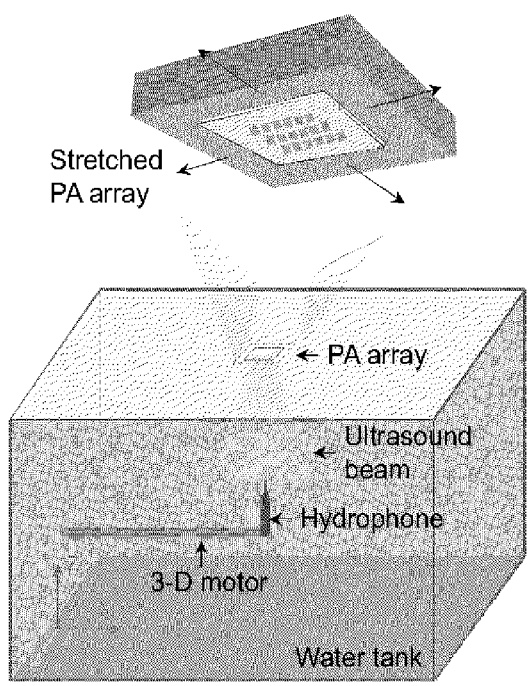
Figure 37C:
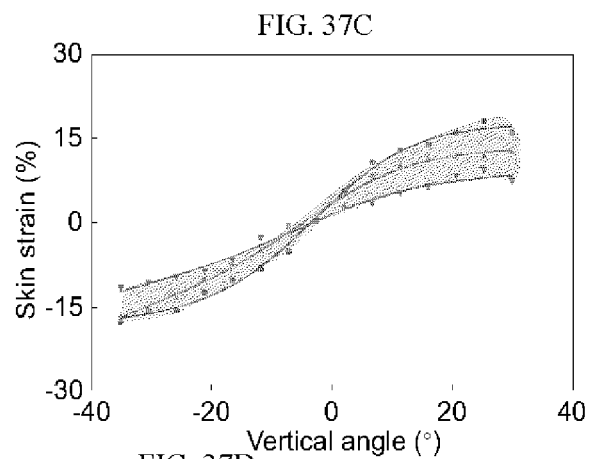
Figure 37D:
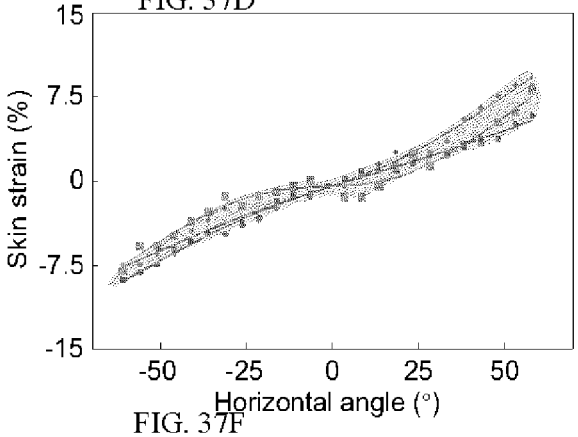
Figure 37F:
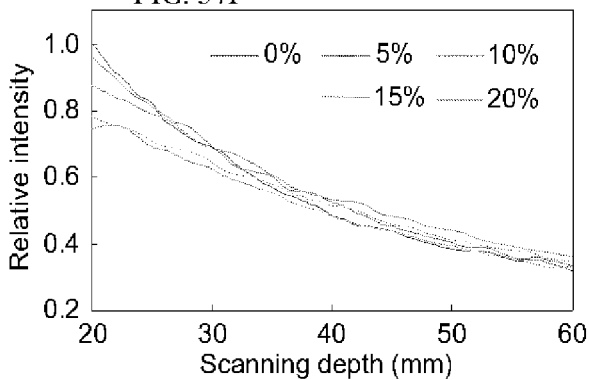
Figure 37G:
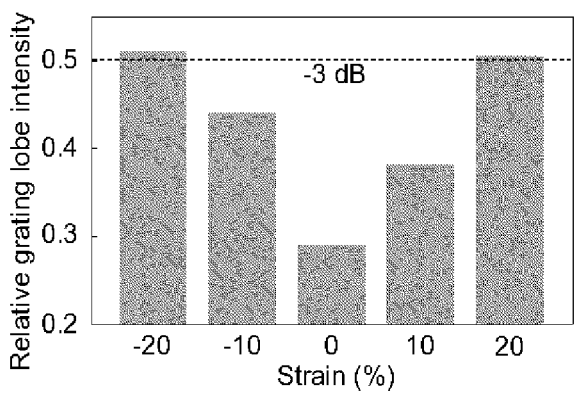

FIGS. 37A-37G illustrate the performance of the wearable monitoring device under tensile/compressive strain. In particular, FIG. 37A shows a schematic experiment setup for strain characterization of the human neck skin during head flexion/extension. A pair of markers are applied to the human neck near the CA region in the vertical direction. The distance between the two markers will increase/decrease when the subject lowers/lifts the head. FIG. 37B shows a schematic experiment setup for strain characterization of the human neck skin during head rotation. A pair of markers are applied to the human neck near the CA region in the vertical direction. The distance between the two markers will increase/decrease when the subject turns the head left/right. FIG. 37C shows the strain of the human neck skin as a function of the pitch (flexion/extension) angle. The data is measured by a 3D scanner (HDI Advances, LMI Technologies, Vancouver, Canada). FIG. 37D shows the strain of the neck skin as a function of the yaw (rotation) angle. The negative sign means the strain is compressive. Note that the skin will not be under compressive strain but will form wrinkles to adapt to the compression. The data is measured by a 3D scanner (HDI Advances, LMI Technologies, Vancouver, Canada). FIG. 37E shows a schematic experiment setup for characterization of the performance of the wearable monitoring device under biaxial tensile strain applied with a mechanical stretcher. The mapping system is illustrated in the bottom panel. FIG. 37F shows the beam intensity of the wearable monitoring device under 0%-20% tensile strain. The strain does not have a significant impact on the intensity of the main beam. The data are mapped in Acoustic Intensity Measurement System (Onda, Sunnyvale, CA). FIG. 37G shows a relative grating lobe intensity of the wearable monitoring device under −20%-20% strain. (The data in the tensile strain is measured in the experiment, the data in the compressive strain regime is derived from the simulation in Field II, MATLAB (MathWorks, Natick, MA)) The −3 dB threshold is labeled in the figure above which the grating lobe starts to influence the main beam in biomedical applications. The result shows the working range of the device is around 20% of tensile strain.

Figure 38A:
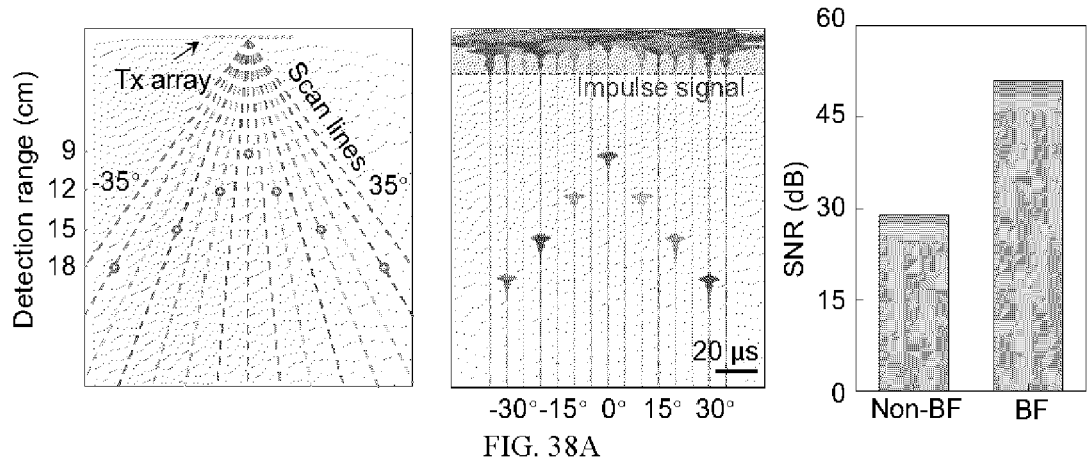
FIGS. 38A, 38B, 38C and 38D illustrate the large sensing range of the wearable monitoring device in x-z plane as enabled by phased array receive beamforming.
Figure 38B:
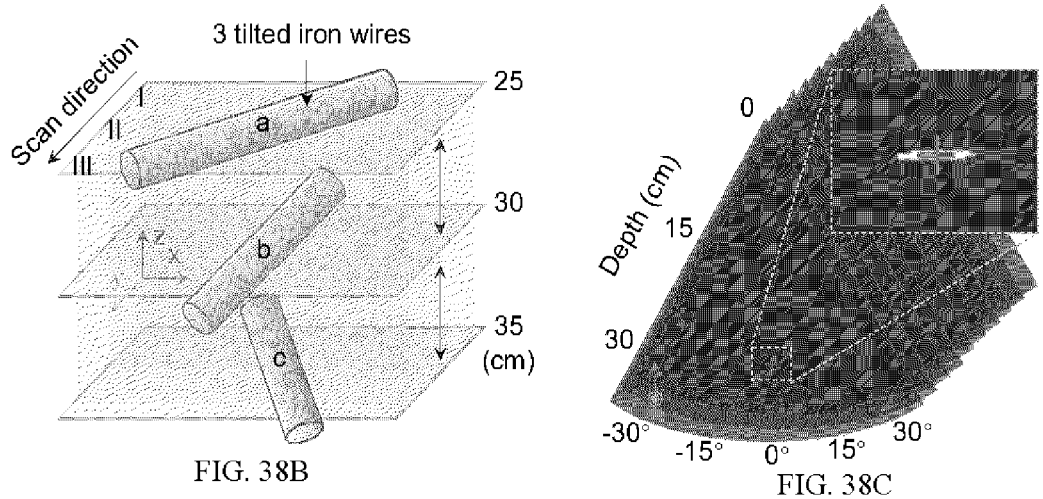
Figure 38C:
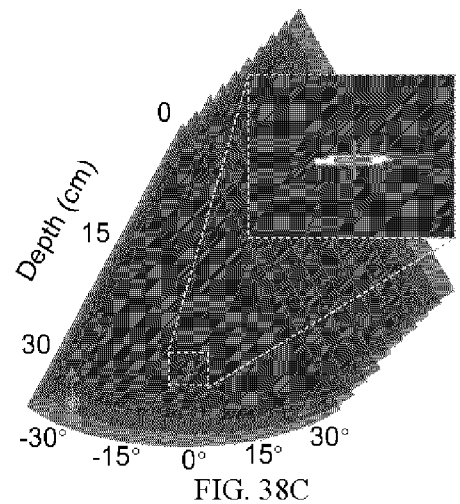
Figure 38D:
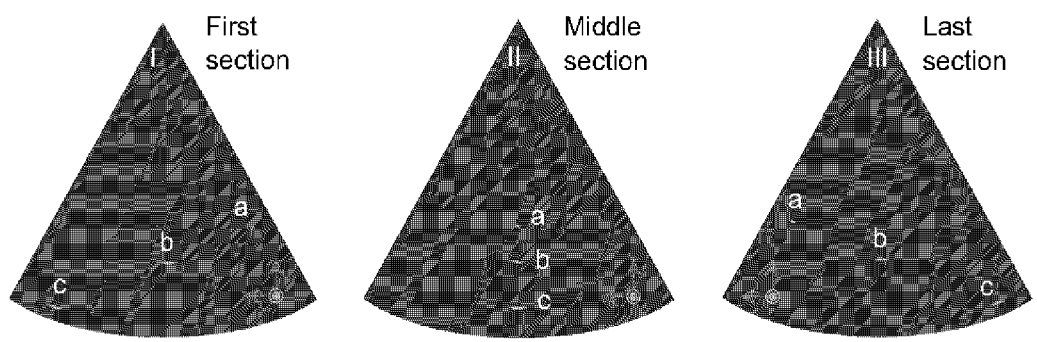

FIGS. 38A-38D illustrate the large sensing range of the wearable monitoring device in x-z plane as enabled by phased array receive beamforming. In particular, FIG. 38A shows the designed experimental setup at 10~20 cm depth in water (the left panel). Seven reflectors (iron wires, marked by the circles) are arranged at a depth of 9, 12, 15, and 18 cm, respectively, with the angle between the vertical direction and the beamline to hit the wire being 0°, 10°, 20°, and 30°, respectively. To detect those targets, 15 beamlines are created at an incidence angle of −35° to 35°, with a 5° increment. The received signals from the corresponding beamlines are in the middle panel. Pulse signals (in the pink shaded area) are due to the ringing effect of the transducer. The pulse signals will not be used to track objects. The SNR is enhanced and reaches 51 dB after implementing phased array receive beamforming, as the right panel. The high-quality signals from the wearable monitoring device demonstrate its potential for central organ sensing. FIG. 38B is a 3D imaging of three reflectors (iron wires) at a depth of 25 cm (wire a), 30 cm (wire b), and 35 cm (wire c), in different orientations (−30° to 30° in the x-y plane). FIG. 38C shows ten consecutive cross-sectional images along the y-axis of the 3D image generated with the wearable monitoring device in the sensing scenario in FIG. 38B. The 3D scans were conducted by adopting the strategy as illustrated in FIGS. 27A and 27B. The positions of the reflectors are labeled by the red cross. The inset shows the zoomed-in image of a reflector. FIG. 38D shows three representative cross-sections I, II, and III from FIG. 38C with the same scale as FIG. 36C. The images are processed using the binarization method (with 5 V signal threshold). The gain is 100 dB.

Figures 39A, 39B, 39C:
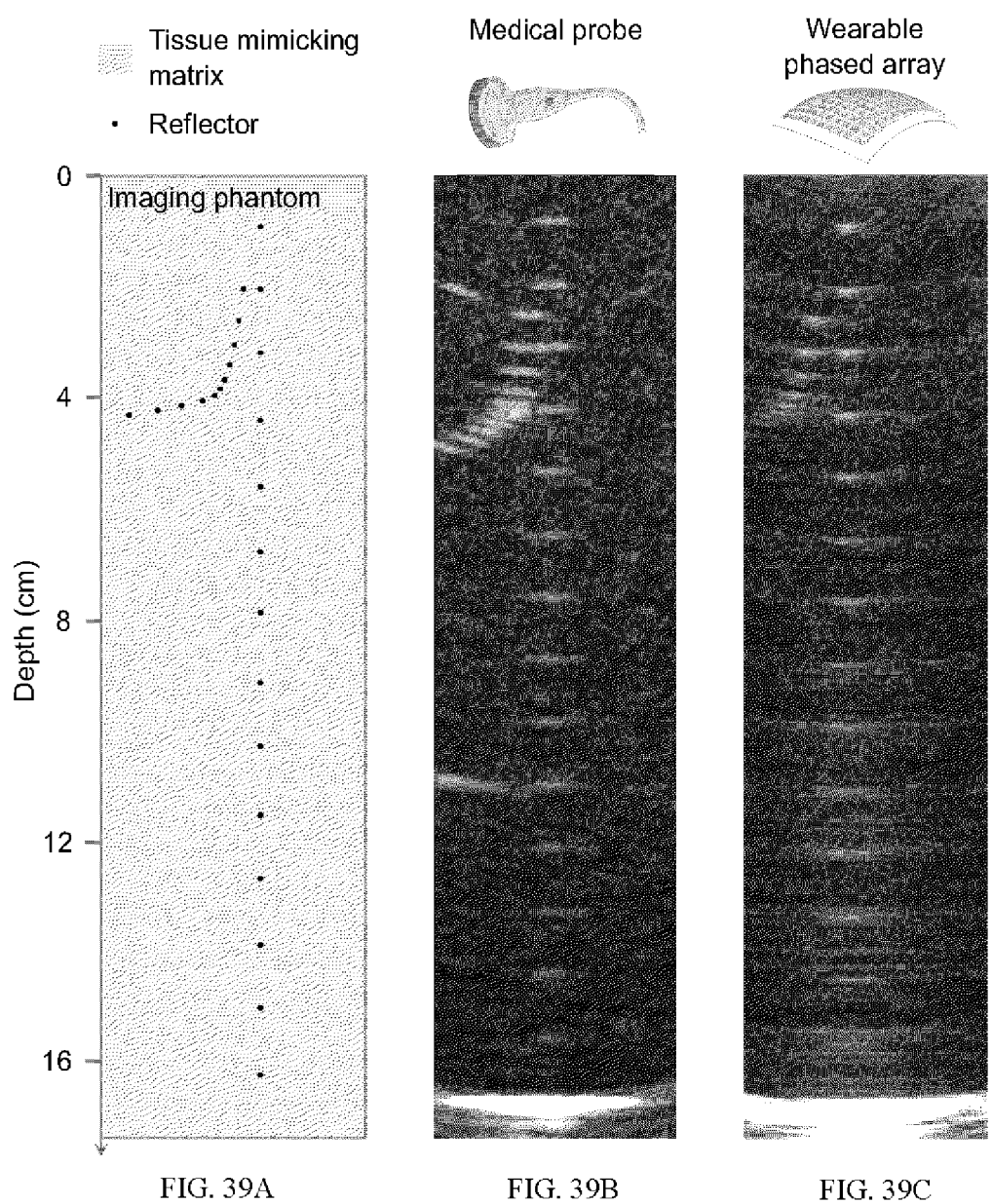
FIGS. 39A, 39B and 39C compare the detection capabilities between the wearable monitoring device and a commercial probe on a tissue-mimicking phantom.

FIGS. 39A-39C compare the detection capabilities between the wearable monitoring device and a commercial probe on a tissue-mimicking phantom. In particular, FIG. 39A shows a tissue-mimicking phantom with reflectors distributed at 0-17 cm depth. FIG. 39B shows the imaging result of a commercial medical ultrasonic probe (Verasonics, P4-2v probe). FIG. 39C is the imaging result of the wearable monitoring device, showing a detection quality comparable to the medical probe.

Figure 40A:
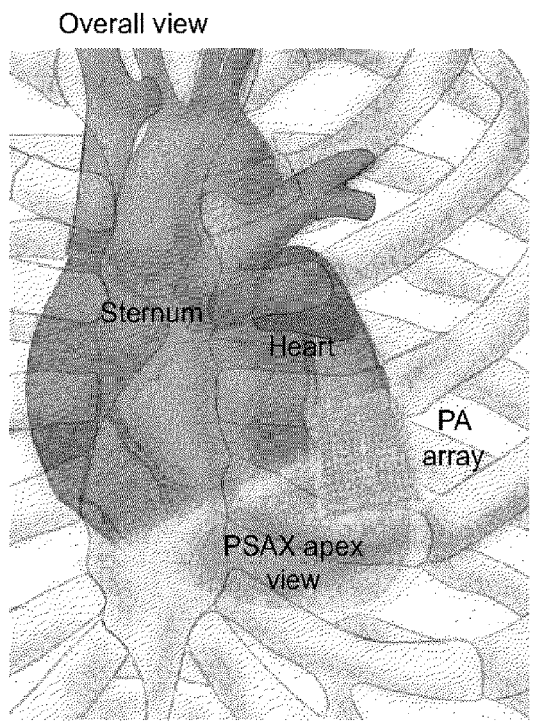
FIGS. 40A and 40B show the anatomy of the human chest during tissue Doppler measurements of cardiac muscles.
Figure 40B:
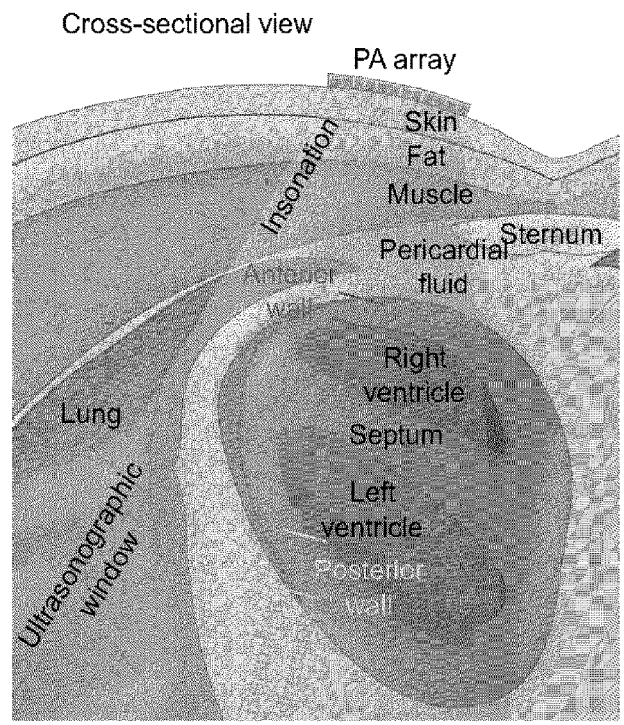

FIGS. 40A and 40B show the anatomy of the human chest during tissue Doppler measurements of cardiac muscles. In particular, FIG. 40A shows the position of the device on the chest relative to the bones and the heart. FIG. 40B shows the cross-sectional structure of the parasternal short axis (PSAX) view, showing the relative position and orientation of the patch, the insonation area, and nearby tissue structures. The beamline penetrates various tissue layers including the skin, fat, muscle, pericardial fluid, right ventricle anterior wall, right ventricle, septum, left ventricle, and left ventricle posterior wall.

FIGS. 41A and 41B show raw RF signals of the tissue Doppler in the time domain and the corresponding human anatomy. In particular, FIG. 41A shows the raw RF signals of the tissue Doppler in one cardiac cycle. Note that the y-axis is time. The x-axis is converted to depth by multiplying the ultrasound speed by the time-of-flight of ultrasound pulses in the human tissue. As a proof of concept, we neglect the non-uniformity of the ultrasound speed in the human body. From the pattern we can clearly observe the reflection peaks from the anterior wall of the right ventricle (RV) in the blue dashed box and the posterior wall of the left ventricle (LV) in the orange dashed box. The position of the reflection peaks shift during the cardiac cycle. The RV anterior wall peak shifts to the left from 0 to 0.6 s, corresponding to right ventricular diastole, and shifts to the right from 0.6 to 0.8 s, corresponding to right ventricular systole. Meanwhile, the peak shifts to the right from 0 to 0.6 s, corresponding to left ventricular diastole, and shifts to the left from 0.6 to 0.8 s, corresponding to left ventricular systole. The peak shifting clearly indicates the relaxation and contraction of the cardiac chambers. FIG. 41B shows the cross-sectional structure of the PSAX view corresponding to the signal peaks in FIG. 41A.

Figure 42:
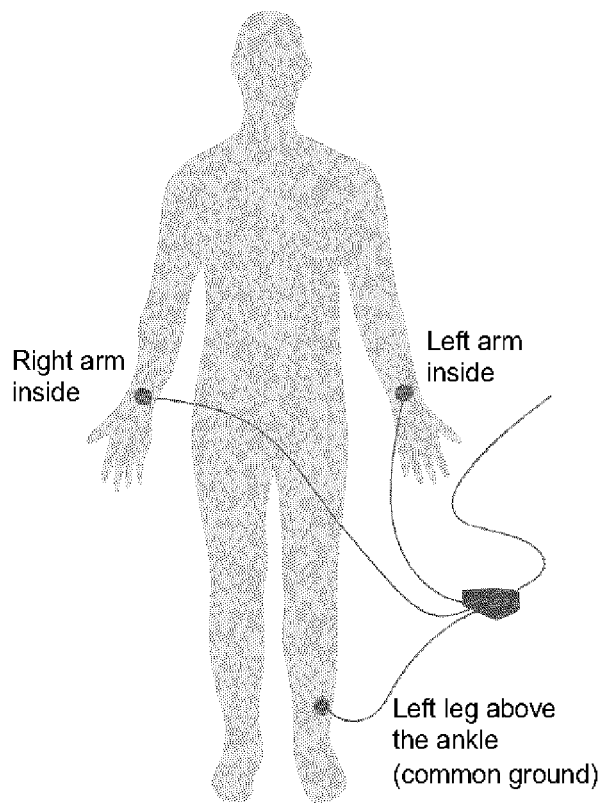
FIG. 42 is a schematic illustration of the electrode placement for ECG measurements.

FIG. 42 is a schematic illustration of the electrode placement for ECG measurements. In particular, FIG. 42 shows three electrodes placed at different locations on limbs, including one on each of the inner lower arms, and one on the left leg above the ankle for the common ground.

Figure 43A:
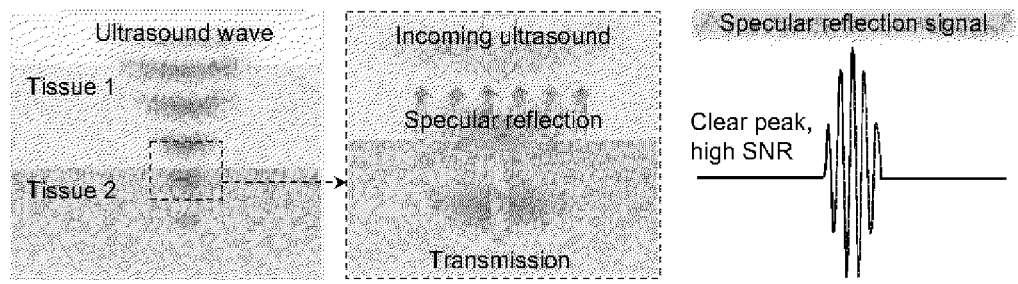
FIGS. 43A and 43B show the distinction between specular reflection and scattering, two major forms of interaction between ultrasound and tissues.
Figure 43B:
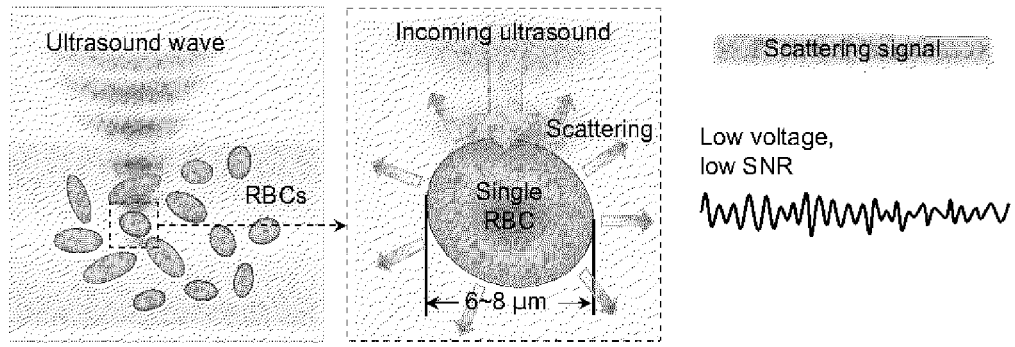

FIGS. 43A and 43B show the distinction between specular reflection and scattering, two major forms of interaction between ultrasound and tissues. In particular, FIG. 43A illustrates that a specular reflection happens when ultrasound meets an interface between two tissues with different ultrasonic properties, i.e., acoustic impedance (the left panel). The zoomed-in image in the middle panel shows more details of the specular reflection. Because the interface is much larger in scale compared to the ultrasound wavelength, a large portion of the ultrasonic energy will be bounced back. Specifically, the reflection/transmission ratio depends on the acoustic impedance difference between tissues 1 and 2. The specular reflection usually has a clear peak with a relatively high SNR (the right panel). FIG. 43B illustrates that scattering happens when ultrasound waves meet tissues or cells whose scales are much smaller than the ultrasound wavelength, such as red blood cells (RBCs, 6-8 µm in size, the left panel). The zoomed-in image in the middle panel gives more details of scattering. The incoming ultrasound wave will be dispersed by the microscopic tissues or cells in all directions. Therefore, the received reflection signal (along a specific direction) has relatively low SNR, compared to specular reflection. To receive scattering signals requires relatively high-intensity ultrasound compared to detecting specular reflections.

Figure 44A:
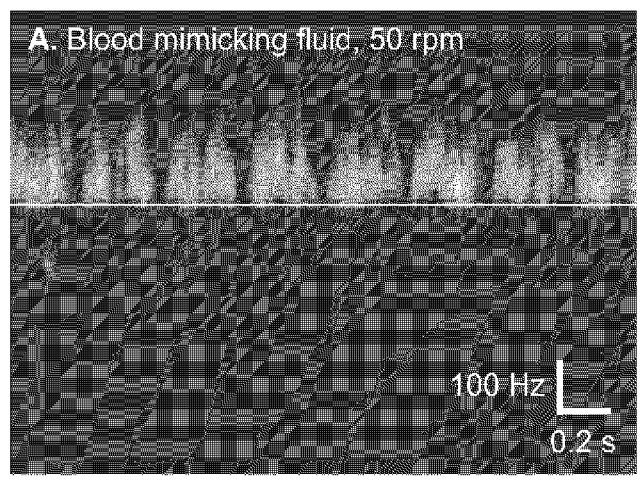
FIGS. 44A and 44B show the scattering spectra with and without scattering particles in water.
Figure 44B:
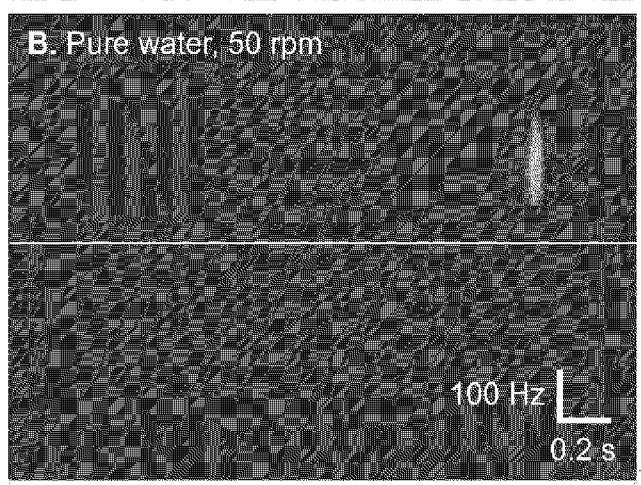

FIGS. 44A and 44B show scattering spectra with and without scattering particles in water. The experiment is performed with a peristaltic pump with scattering particles (shown in FIG. 44A) and without scattering particles (in FIG. 44B). The results show that there is only a detectable Doppler shift when the fluid contains scattering particles (5 µm in size, at a concentration of 1.82%). Pure water cannot introduce any Doppler shift in the ultrasound frequency in this study.

Figure 45A:
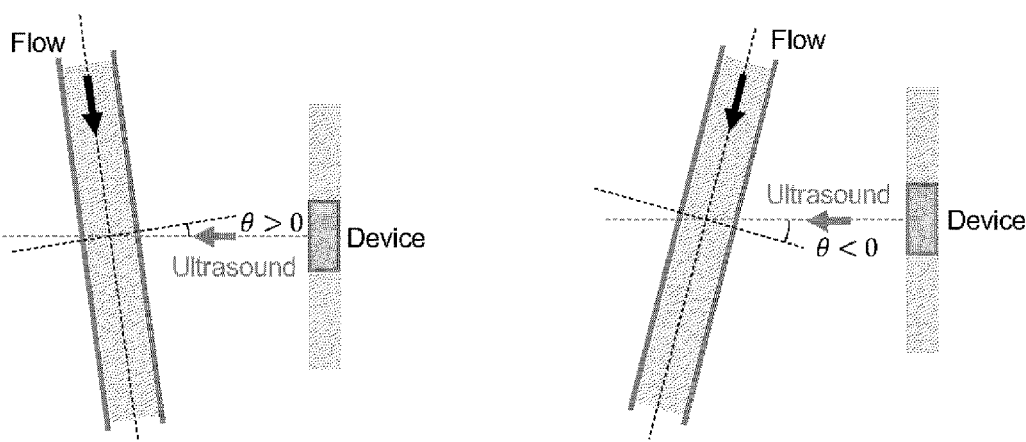
FIGS. 45A and 45B show two key components for estimating the flow speed, including the Doppler shift and the Doppler angle.
Figure 45A:
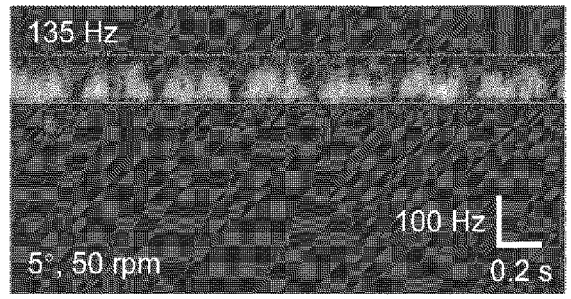
Figure 45B:
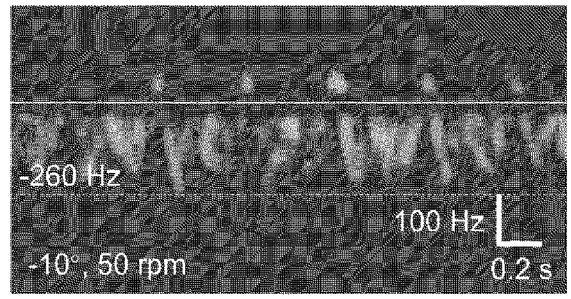

FIGS. 45A and 45B show two key components for estimating the flow speed, including the Doppler shift and the Doppler angle. While measuring the same fluidic flow, the Doppler shift and the Doppler angle are two interdependent parameters that need to be measured to calculate the flow speed. FIG. 45A shows fluid flowing towards the ultrasound wave can introduce a positive Doppler shift, the corresponding spectrum signal appears in the bottom panel. FIG. 45B shows fluid flowing in the same direction as the ultrasound wave (with a smaller absolute angle than that in FIG. 45A)) can introduce a greater, but negative Doppler shift, as the corresponding spectrum signal in the bottom panel.

Figure 46:
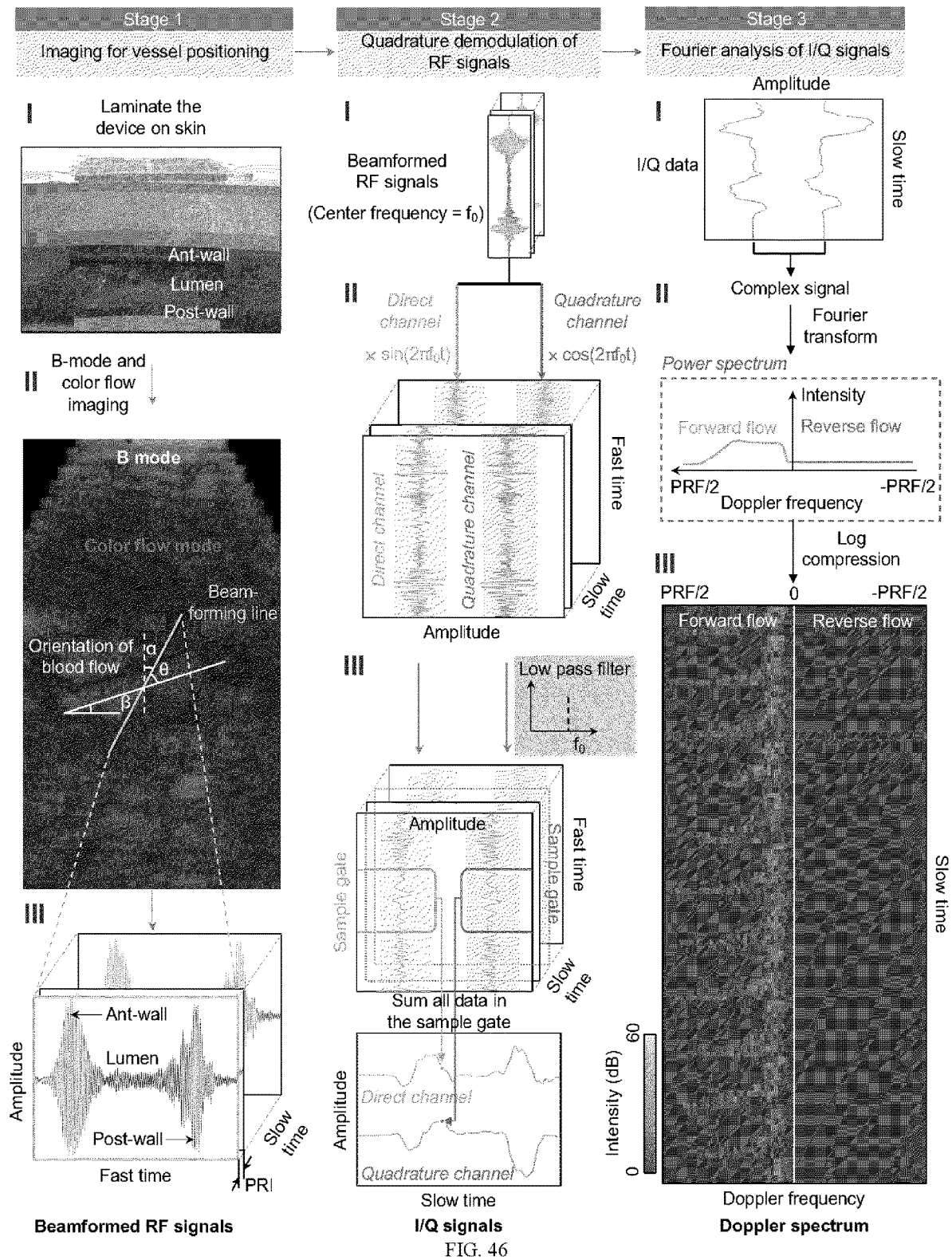
FIG. 46 shows the process of blood flow measurements using the wearable monitoring device.

FIG. 46 shows the process of blood flow measurements using the wearable monitoring device. The entire process is divided into three stages. Stage 1: Imaging for vessel positioning. The blood vessel contains three parts, including the anterior wall, the lumen area, and the posterior wall (as step I). The device will perform combined B mode and color flow imaging (step II), which reveal the directional and spatial information of the vascular flow. The Doppler angle of FIGS. 17D and 17E can be calculated as follows. According to measurements from the CFI image at a beam incidence angle ($\alpha$) of 20° (see Materials and Methods), the carotid artery and the jugular vein in FIGS. 17D and 17E have an inclination angle ($\beta$) of 12° and 16°, corresponding to a Doppler angle ($\theta$) of 58° and 54°, respectively, which are within an acceptable range. A beamforming line with an appropriate Doppler angle will then be defined to read out the Doppler information from the RF signals of this line (step III). In a single frame of the RF signals, the horizontal axis represents the time-of-flight, labeled as "Fast time". The vertical axis represents the signal amplitude. From the RF signals, we can clearly tell the signals from the anterior wall, lumen area, and posterior wall. The third axis, labeled as "Slow time", represents the time of multiple ultrasound generations. The time interval between two adjacent frames is the pulse repetition interval (PRI). These series of frames of the RF signals will be recorded as the raw data for further processing and analysis. Stage 2: Quadrature demodulation of RF signals. After acquisition of the RF signals (step I), quadrature demodulation will be performed to extract the fluidic flow information of both the forward and the reverse directions. In step II, each frame of the RF signals will be multiplied by $\sin(2^\pi f_0 t)$ and $\cos(2^\pi f_0 t)$, respectively, forming two channels of signals, labeled as "Direct channel" and "Quadrature channel". $f_0$ represents the center frequency of the ultrasonic signals. Then, in step III, the resulted signals will pass through a low-pass filter with a cutoff frequency equal to $f_0$. And then, a sampling gate will be applied to only collect the Doppler shift from the lumen area. All data in this sampling gate will be summed up resulting in a single point in the I/Q (in-phase and quadrature) data, which is in the slow time domain. Stage 3: Fourier analysis of I/Q signals. This step translates the previous I/Q data to flow spectra. Two channels of real I/Q signals (step I) will be used to compose a new complex signal. In step II, by conducting an FFT of this composed signal, the intensity distribution of both scatters contributing to the forward flow and the reverse flow can be differentiated in the Doppler spectrum. The orange curve has a positive Doppler shift (on the left side of 0 Hz); the blue curve is the opposite. Then, in step III, we encode the amplitude information into brightness by log compression. By linking all single brightness mode pixels, the flow spectrum containing forward and backward fluidic flow information can be reconstructed. Under normal blood flow conditions at a regular velocity, the spectrum represents mixed Doppler frequencies existing in a particular vessel during a finite time span. Specifically, in the vessel lumen, particularly under laminar flow conditions, blood flow has a velocity gradient across the cross-section of the vessel, wherein the center has the greatest velocity and the region close to the vascular wall has the least. The gradient in the flow velocities in the vessel lumen generates different scattering intensities.

Figure 47A:
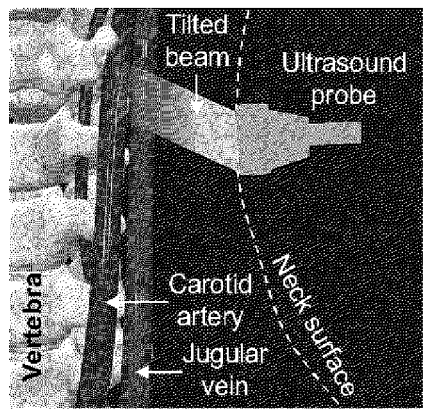
FIGS. 47A, 47B, 47C and 47D show Doppler angle dependence of the blood flow velocity measurements.
Figure 47B:
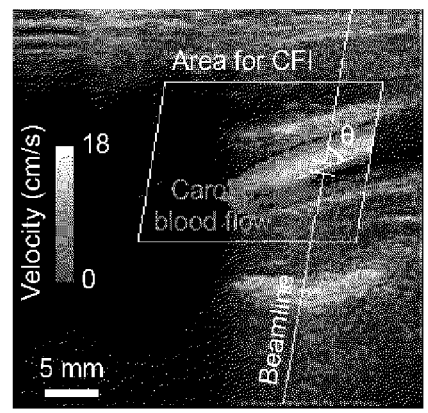
Figure 47C:
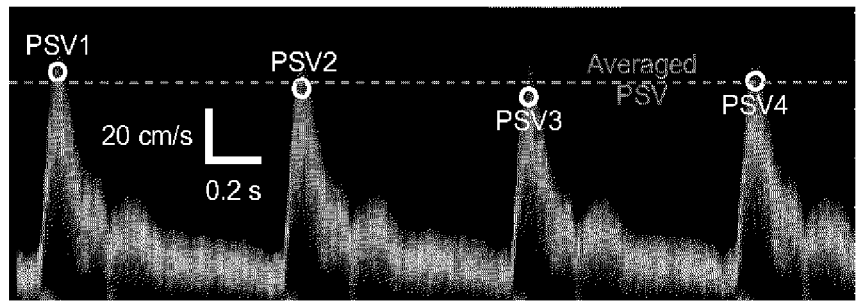
Figure 47D:
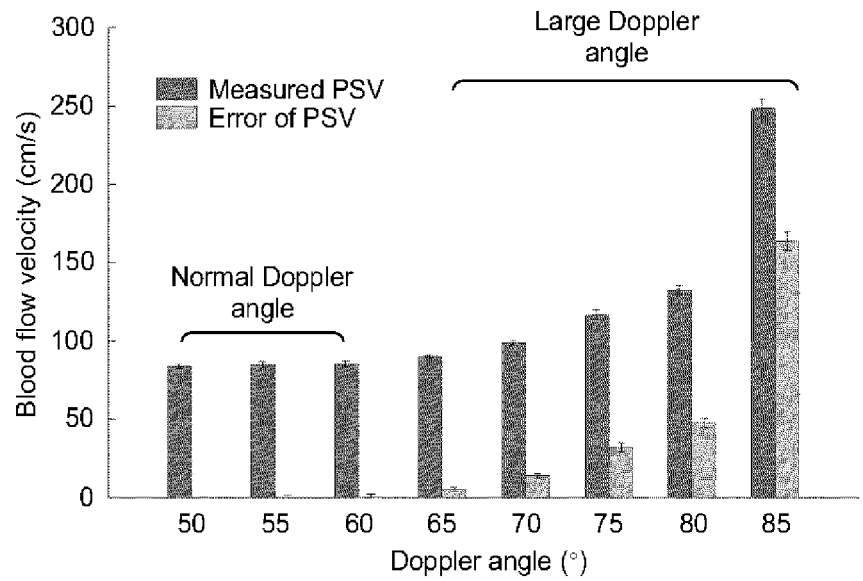

FIGS. 47A-47D show doppler angle dependence of the blood flow velocity measurements. In particular, FIG. 47A is an illustration of a tilted ultrasonic beam for blood flow measurements. FIG. 47B shows an integrated B-mode and color flow imaging for measuring the Doppler angle ($\theta$) between the CA and the ultrasound beam, which is essential for blood flow velocity calculation. FIG. 47C shows measured blood flow spectra. Four peaks systolic velocity (PSV)

readings and the average PSV are labeled. FIG. 47D shows measured PSV and errors on the same subject with different Doppler angles (50°~85°). The measured PSV is significantly overestimated when the Doppler angle exceeds 60°. According to the translational equation between the Doppler shift and flow speed, the larger θ is, the closer cos θ is to zero, and the larger the measurement error will be.

Figure 48A:
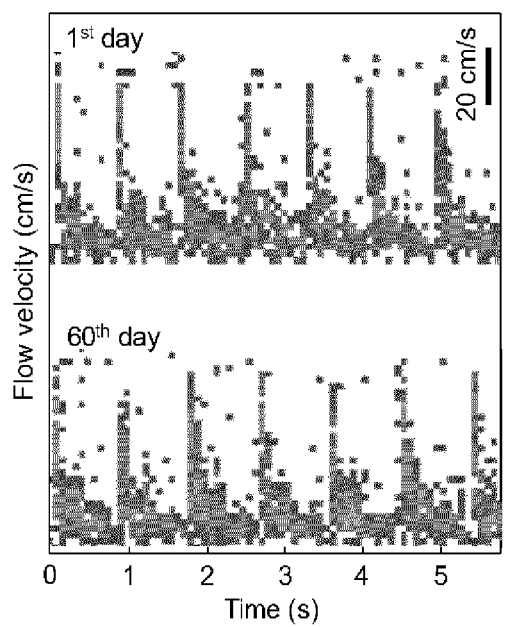
FIGS. 48A and 48B illustrate the lifetime of the wearable monitoring device.
Figure 48B:
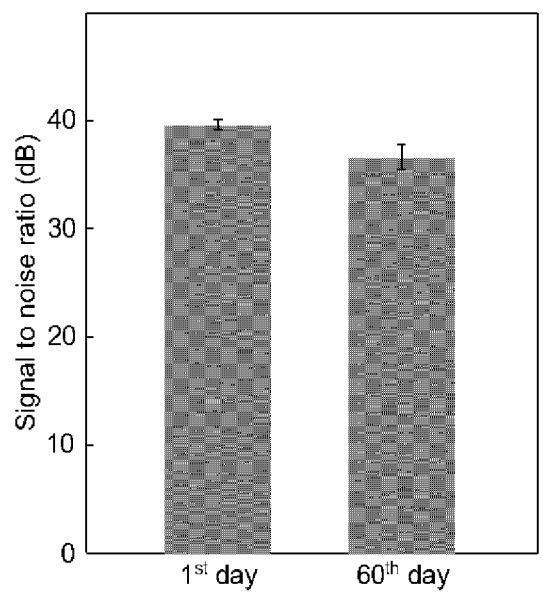

FIGS. 48A and 48B illustrate the lifetime of the wearable monitoring device. In particular, FIG. 48A shows measurements of CBF of a subject on the 1$^{st}$ day right after device fabrication (top) and on the 60$^{th}$ day (bottom) using the same device. Both tests can achieve reliable and similar results. FIG. 48B shows the SNR of the same device, measured underwater at a depth of 30 cm on the 1$^{st}$ day and 60$^{th}$ day, showing a 2.5 dB drop after long-term testing, probably due to the wear of the substrate, potential depolarization of the transducer material, or the degradation of the PZT-based transducer material induced by moisture. The device usage between the 1$^{st}$ and 60$^{th}$ day is ~3-4 times per week.

Although the subject matter has been described in language specific to structural features and/or methodological acts, it is to be understood that the subject matter defined in the appended claims is not necessarily limited to the specific features or acts described above.

The invention claimed is:

1. A method for monitoring a patient using an ultrasonic probe, comprising:
attaching a conformable two-dimensional piezoelectric transducer array having a plurality of phased array piezoelectric transducer elements on an epidermal surface of a patient so that the conformable two-dimensional piezoelectric transducer array conforms to a shape of the epidermal surface wherein the phased array piezoelectric transducer elements have a pitch about equal to one ultrasound wavelength at which the plurality of phased array piezoelectric transducer elements operate operating the plurality of phased array piezoelectric transducer elements as a phased array to transmit a focused ultrasonic beam so that the focused ultrasonic beam penetrates to a depth of at least 4 cm for continuous hemodynamic monitoring of central organs and at least 6 cm for cardiac activity monitoring;
receiving ultrasound waves from the patient using the plurality of phased array piezoelectric transducer elements; and
displaying an indication of the received ultrasound waves.

2. The method of claim 1, wherein the specified location is a vessel and the displaying includes displaying an indication of vascular blood flow in the vessel.

3. The method of claim 2, wherein the vessel is the carotid artery of the patient.

4. The method of claim 1, wherein the specified location is a central organ of the patient.

5. The method of claim 4, wherein the monitoring is performed to conduct blood flow spectrum recording.

6. The method of claim 1, wherein the operating is performed automatically without user intervention to steer the focused ultrasonic beam to the specified location without changing a physical position of the phased array piezoelectric transducer elements.

7. The method of claim 1, wherein the phased array piezoelectric transducer elements are individually controllable, and the operating is performed to control activation of the phased array transducer elements using a time-delay profile.

8. The method of claim 1, wherein the receiving is performed to monitor lower extremity vascular perfusion.

9. The method of claim 1, wherein the conformable two-dimensional piezoelectric transducer array is flexible and stretchable to establish contact with a nonplanar epidermal surface of the patient.

10. The method of claim 1, wherein transmitting the focused ultrasonic beam includes steering the focused ultrasonic beam to a specified spatial location below the epidermal surface by programming a time delay of each of the phased array piezoelectric transducer elements based on calculations of a physical distance between a focal point and each of the piezoelectric transducer elements.

11. The method of claim 1, wherein the operating further comprises determining a distribution and relative position of the phased array piezoelectric transducer elements on the surface of the patient with an optical fiber or 3D camera to map a location of each of the piezoelectric transducer elements using optical frequency domain reflectometry.

12. The method of claim 1, further comprising using phased array receive beamforming to reconstruct an echo signal from the received ultrasound waves.

13. The method of claim 1 wherein the monitoring is performed to conduct Doppler imaging.

14. A conformable piezoelectric transducer array, comprising:
a silicone elastomer substrate and a silicone elastomer superstrate;
a plurality of phased array piezoelectric transducer elements disposed between the silicone elastomer substrate and the silicone elastomer superstrate, wherein the phased array piezoelectric transducer elements have a pitch about equal to one ultrasound wavelength at which the plurality of phased array piezoelectric transducer elements operate;
a first electrical interconnect layer electrically interconnecting a first surface of the phased array transducer elements adjacent to the silicone elastomer substrate;
a second electrical interconnect layer electrically interconnecting a second surface of the phased array transducer elements adjacent to the superstrate; and
a controller configured to operate the plurality of phased array piezoelectric transducer elements as a phased array to transmit a focused ultrasonic beam so that the focused ultrasonic beam penetrates to a depth of at least 4 cm for continuous hemodynamic monitoring of central organs and at least 6 cm for cardiac activity monitoring.

15. The conformable piezoelectric transducer array of claim 14, wherein the controller is further configured to operate automatically without user intervention to steer the focused ultrasonic beam to the specified location without changing a physical position of the piezoelectric transducer elements.

16. The conformable piezoelectric transducer array of claim 14, wherein the piezoelectric transducer elements are individually controllable and the controller is further configured to control activation of the piezoelectric transducer elements using a time-delay profile.

17. The conformable piezoelectric transducer array of claim 14, wherein the controller is further configured to provide a time-delay profile for each of the phased array piezoelectric transducer elements to increase a penetration depth of the focused ultrasonic beam and to enable phased array beamforming to reconstruct an echo signal by taking into account signals received from all the phased array piezoelectric transducer elements to thereby increase the signal-to-noise ratio.

* * * * *

UNITED STATES PATENT AND TRADEMARK OFFICE
CERTIFICATE OF CORRECTION

| | | |
|---|---|---|
| PATENT NO. | : 12,402,855 B2 | Page 1 of 1 |
| APPLICATION NO. | : 17/604616 | |
| DATED | : September 2, 2025 | |
| INVENTOR(S) | : Sheng Xu et al. | |

It is certified that error appears in the above-identified patent and that said Letters Patent is hereby corrected as shown below:

In the Specification

Please add the following government funding statement at Column 1, Line 5 following the title:
Government Funding
This invention was made with government support under HL119893 awarded by the National Institutes of Health. The government has certain rights in the invention.

Signed and Sealed this
Second Day of December, 2025

John A. Squires
*Director of the United States Patent and Trademark Office*